US008574584B2

(12) United States Patent
Storkus et al.

(10) Patent No.: US 8,574,584 B2
(45) Date of Patent: *Nov. 5, 2013

(54) EPHA2 T CELL EPITOPES AND USES THEREFOR

(75) Inventors: Walter J. Storkus, Glenshaw, PA (US); Michael S. Klnch, Laytonsville, MD (US)

(73) Assignee: University of Pittsburgh —of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/355,343

(22) Filed: Jan. 20, 2012

(65) Prior Publication Data

US 2012/0201840 A1      Aug. 9, 2012

Related U.S. Application Data

(60) Division of application No. 11/977,179, filed on Oct. 22, 2007, now Pat. No. 8,114,407, which is a continuation of application No. 11/233,796, filed on Sep. 23, 2005, now Pat. No. 7,297,337, which is a continuation of application No. 10/897,711, filed on Jul. 22, 2004, now abandoned.

(60) Provisional application No. 60/491,046, filed on Jul. 30, 2003.

(51) Int. Cl.
*A61K 39/00* (2006.01)
*A61K 38/00* (2006.01)
*C12N 15/09* (2006.01)

(52) U.S. Cl.
USPC ..... 424/185.1; 435/69.3; 514/21.6; 514/21.3; 530/324

(58) Field of Classification Search
None
See application file for complete search history.

(56) References Cited

U.S. PATENT DOCUMENTS

| | | | |
|---|---|---|---|
| 5,837,448 | A | 11/1998 | Lemke et al. |
| 5,981,245 | A | 11/1999 | Fox et al. |
| 7,297,337 | B2 | 11/2007 | Storkus et al. |
| 7,612,162 | B2 | 11/2009 | Okada et al. |
| 8,114,407 | B2 | 2/2012 | Storkus et al. |
| 2005/0048550 | A1 | 3/2005 | Storkus et al. |
| 2006/0034856 | A1 | 2/2006 | Kosmatopoulos et al. |
| 2010/0008940 | A1 | 1/2010 | Okada et al. |

FOREIGN PATENT DOCUMENTS

| | | |
|---|---|---|
| WO | WO/02/48336 | 6/2002 |
| WO | WO/02/066605 | 8/2002 |
| WO | WO/03/014303 | 2/2003 |
| WO | WO/03/091383 | 11/2003 |

OTHER PUBLICATIONS

U.S. Appl. No. 10/897,711, filed Jul. 22, 2004 (Abandoned) (Mar. 3, 2005).
U.S. Appl. No. 10/897,711, Dec. 21, 2005 Notice of Abandonment.
U.S. Appl. No. 10/897,711, Mar. 24, 2005 Non-Final Office Action.
U.S. Appl. No. 11/233,796, Jun. 19, 2012 Certificate of Correction.
U.S. Appl. No. 11/233,796, Sep. 25, 2007 Issue Fee payment and Amendment after Notice of Allowance.
U.S. Appl. No. 11/233,796, Jun. 26, 2007 Notice of Allowance.
U.S. Appl. No. 11/233,796, Apr. 13, 2007 Amendment and Request for Continued Examination (RCE).
U.S. Appl. No. 11/233,796, Feb. 21, 2007 Final Office Action.
U.S. Appl. No. 11/233,796, Nov. 20, 2006 Response to Non-Final Office Action.
U.S. Appl. No. 11/233,796, May 18, 2006 Non-Final Office Action.
U.S. Appl. No. 11/977,179, Jan. 10, 2012 Issue Fee payment.
U.S. Appl. No. 11/977,179, Oct. 11, 2011 Notice of Allowance.
U.S. Appl. No. 11/977,179, Apr. 22, 2011 Request for Continued Examination (RCE).
U.S. Appl. No. 11/977,179, Jan. 24, 2011 Notice of Allowance.
U.S. Appl. No. 11/977,179, Oct. 28, 2010 Response to Non-Final Office Action.
U.S. Appl. No. 11/977,179, Jun. 28, 2010 Non-Final Office Action.
Andersen, et al., "Poor correspondence between predicted and experimental binding of peptides to class I MHC molecules", *Tissue Antigens*, 55(6):519-31 (2000).
Brusic, et al., "Prediction of promiscuous peptides that bind HLA class I molecules", *Immunol. cell Biol.*, 80(3):280-5 (2002).
Carles-Kinch, et al., "Antibody targeting of the EphA2 tyrosine kinase inhibits malignant cell behavior", *Cancer Research*, 62(10):2840-7 (2002).
Chen, et al., The Journal of Immunology 157:3783-90 (1996).
De Groot, et al., "From genome to vaccine: In silico predictions, ex vivo verification", *Vaccine*, 19(31):4385-95 (2001).
Ebner, et al., "Identification of multiple T cell epitopes on Bet v I, the major birch pollen allergen, using specific T cell clones and overlapping peptides", *J. Immunol.*, 150(3):1047-54 (1993).
Geneseq Accession No. ABP66625, Human breast specific protein SEQ ID No. 127, Dec. 6, 2002.
Geneseq Accession No. ABJ04211, Kinase-associated signal transduction modulating peptide 44, Oct. 24, 2002.
Hatano, et al., "EphA2 as a glioma-associated antigen: a novel target for glioma vaccines", *Neoplasia*, 7(8):717-22 (2005).
Hatano, et al., "Vaccination with EphA2-derived T cell-epitopes promotes immunity against both EphA2-expressing and EphA2-negative tumors", *J. Trans. Med.*, 2:40 (2004).
Herrem, et al., "Expression of EphA2 is prognostic of disease-free interval and overall survival in surgically treated patients with renal cell carcinoma", *Clin. Cancer Res.*, 11:226-31 (2005).

(Continued)

*Primary Examiner* — Marsha Tsay
(74) *Attorney, Agent, or Firm* — Baker Botts, L.L.P.

(57) ABSTRACT

EphA2 T-cell epitope are provided herein. The epitopes include peptides corresponding to specific fragments of human EphA2 protein containing one or more T-cell epitopes, and conservative derivatives thereof. The EphA2 T-cell epitopes are useful in an assay, such as an ELISPOT assay, that may be used to determine and/or quantify a patient's immune responsiveness to EphA2. The epitopes also are useful in methods of modulating a patient's immune reactivity to EphA2, which has substantial utility as a treatment for cancers that overexpress EphA2, such as renal cell carcinoma (RCC). The EphA2 epitopes also can be used to vaccinate a patient against EphA2, by in vivo or ex vivo methods.

10 Claims, 32 Drawing Sheets

(56) References Cited

OTHER PUBLICATIONS

Herrem, et al., "CD8+ and CD4+ T cell-mediated immunity against novel EphA2-derived epitopes in patients with renal cell carcinoma", 90th *Anniversary Annual Meeting of the American Associate of Immunologists*, Denver, CO, Meeting Abstract No. 162-27, p. c333, May 6-10, 2003.
Honeyman, et al., "Neural network-based prediction of candidate T-cell epitopes", *Nat. Biotechnol.*, 16(10):966-9 (1998).
Koolpe, et al., "An ephrin mimetic peptide that selectively targets the EphA2 receptor", *J. Biol. chem.*, 277(49):46974-9 (2002).
Kuttler, et al., "An algorithm for the prediction of proteasomal cleavages", *J. Mol. Biol.*, 417-29 (2000).
Lindberg, et al., "cDNA cloning and characterization of eck, an epithelial cell receptor protein-tyrosine kinase in the *eph/elk* family of protein kinases", *Molecular and cellular Biology*, 10(12):6316-24 (1990).
Nussbaum, et al., PAProC: A prediction algorithm for proteasomal cleavages available on the www.Immunogenet., 53(2):87-94 (2001).
Sant' Angelo, et al., Immunity 4:367-76 (1996).
Schirle, et al., "Combining computer algorithms with experimental approaches permits the rapid and accurate identification of T cell epitopes from defined antigens", *J. Immunol. Methods*, 257(1-2):1-16 (2001).
Sergel, et al., "A single amino acid change in the Newcastle disease virus fusion protein alters the requirement for HN protein in fusion", *J. Virol.*, 74(11):5101-7 (2000).
Singh, et al., "ProPed: Prediction of HLA-DR binding sites", *Bioinformatics*, 17(12):1236-7 (2001).
Sloan-Lancaster, et al., Nature 363:156-9 (1993).
Southwood, et al., "Several common HLA-DR types share largely overlapping peptide binding repertoires", *J. Immunol.*, 160(7):3363-73 (1998).
Tatsumi, et al., "Disease stage variation in CD4+ and CD8+ T-cell reactivity to the receptor tyrosine kinase EphA2 in patients with renal cell carcinoma", *Cancer Res.*, 63(15):4481-9 (2004).
Tatsumi, et al., "Disease-associated bias in T helper type 1 (Th1)/th2 CD4+ T cell responses against MAGE-6 in HLA-DRB1*0401+ patients with renal cell carcinoma or melanoma",*J. Exp. Med.*, 196(5):619-28 (2002).
UniProt Accession No. BCD037166, Ephrin Receptor EphA2, Abstract, p. 1/1, Oct. 1, 2002.
UniProt Accession No. Q8N3Z2, Ephrin Receptor EphA2, Oct. 1, 2002.
Walker-Daniels, et al., "c-Cbl-dependent EphA2 protein degradation is induced by ligand binding", *Mol. Cancer Res.*, 1(1):79-87 (2002).
Walker-Daniels, et al., "Overexpression of the EphA2 tyrosine kinase in prostate cancer", *The Prostate*, 41(4):275-80 (1999).
Wesa, et al., "Enhancement in specific CD8+ T cell recognition of EphA2+ tumors in vitro and in vivo after treatment with ligand agonists", *J. Immunol.*, 181:7721-7 (2008).
Zabell, et al., "Expression and purification of the intact cytoplasmic domain of the human ephrin receptor A2 tyrosine kinase in *Escherichia coli*", *Protein Expr. Purif.*, 47(1):210-6 (2006).
Zhong, et al., "Genome-wide characterization of a viral cytotoxic T lymphocyte epitope repertoire", *J. Biol. Chem.*, 278(46):45135-44 (2003).
Partial European Search Report, EP-1995256-A1, dated Jan. 9, 2008.
Genbank NCBI protein Accession No. P29317, 1990.
Canadian Office Action for Canadian Patent Application No. 2,533,789, dated May 3, 2012. (corresponding to U.S. Appl. No. 13/355,343).

```
  1 MELQAARACF ALLWGCALAA AAAAQGKEVV LLDFAAAGGE LGWLTHPYGK GWDLMQNIMN
 61 DMPIYMYSVC NVMSGDQDNW LRTNWVYRGE AERIFIELKF TVRDCNSFPG GASSCKETFN
121 LYYAESDLDY GTNFQKRLFT KIDTIAPDEI TVSSDFEARH VKLNVEERSV GPLTRKGFYL
181 AFQDIGACVA LLSVRVYYKK CPELLQGLAH FPETIAGSDA PSLATVAGTC VDHAVVPPGG
241 EEPRMHCAVD GEWLVPIGQC LCQAGYEKVE DACQACSPGF FKFEASESPC LECPEHTLPS
301 PEGATSCECE EGFFRAPQDP ASMPCTRPPS APHYLTAVGM GAKVELRWTP PQDSGGREDI
361 VYSVTCEQCW PESGECGPCE ASVRYSEPPH GLTRTSVTVS DLEPHMNYTF TVEARNGVSG
421 LVTSRSFRTA SVSINQTEPP KVRLEGRSTT SLSVSWSIPP PQQSRVWKYE VTYRKKGDSN
481 SYNVRRTEGF SVTLDDLAPD TTYLVQVQAL TQEGQGAGSK VHEFQTLSPE GSGNLAVIGG
541 VAVGVVLLLV LAGVGFFIHR RRKNQRARQS PEDVYFSKSE QLKPLKTYVD PHTYEDPNQA
601 VLKFTTEIHP SCVTRQKVIG AGEFGEVYKG MLKTSSGKKE VPVAIKTLKA GYTEKQRVDF
661 LGEAGIMGQF SHHNIIRLEG VISKYKPMMI ITEYMENGAL DKFLREKDGE FSVLQLVGML
721 RGIAAGMKYL ANMNYVHRDL AARNILVNSN LVCKVSDFGL SRVLEDDPEA TYTTSGGKIP
781 IRWTAPEAIS YRKFTSASDV WSFGIVMWEV MTYGERPYWE LSNHEVMKAI NDGFRLPTPM
841 DCPSAIYQLM MQCWQQERAR RPKFADIVSI LDKLIRAPDS LKTLADFDPR VSIRLPSTSG
901 SEGVPFRTVS EWLESIKMQQ YTEHFMAAGY TAIEKVVQMT NDDIKRIGVR LPGHQKRIAY
961 SLLGLKDQVN TVGIPI
```

Fig. 1

```
   1 GGCACGAGGA GGGGCAGAAG TTGCGCGCAG GCCGGCGGGC GGGAGCGGAC ACCGAGGCCG
  61 GCGTGCAGGC GTGCGGGTGT GCGGGAGCCG GGCTCGGGGG GATCGGACCG AGAGCGAGAA
 121 GCGCGGCATG GAGCTCCAGG CAGCCCGCGC CTGCTTCGCC CTGCTGTGGG GCTGTGCGCT
 181 GGCCGCGGCC GCGGCGGCGC AGGGCAAGGA AGTGGTACTG CTGGACTTTG CTGCAGCTGG
 241 AGGGGAGCTC GGCTGGCTCA CACACCCGTA TGGCAAAGGG TGGGACCTGA TGCAGAACAT
 301 CATGAATGAC ATGCCGATCT ACATGTACTC CGTGTGCAAC GTGATGTCTG GCGACCAGGA
 361 CAACTGGCTC CGCACCAACT GGGTGTACCG AGGAGAGGCT GAGCGTATCT TCATTGAGCT
 421 CAAGTTTACT GTACGTGACT GCAACAGCTT CCCTGGTGGC GCCAGCTCCT GCAAGGAGAC
 481 TTTCAACCTC TACTATGCCG AGTCGGACCT GGACTACGGC ACCAACTTCC AGAAGCGCCT
 541 GTTCACCAAG ATTGACACCA TTGCGCCCGA TGAGATCACC GTCAGCAGCG ACTTCGAGGC
 601 ACGCCACGTG AAGCTGAACG TGGAGGAGCG CTCCGTGGGG CCGCTCACCC GCAAAGGCTT
 661 CTACCTGGCC TTCCAGGATA TCGGTGCCTG TGTGGCGCTG CTCTCCGTCC GTGTCTACTA
 721 CAAGAAGTGC CCCGAGCTGC TGCAGGGCCT GGCCCACTTC CCTGAGACCA TCGCCGGCTC
 781 TGATGCACCT TCCCTGGCCA CTGTGGCCGG CACCTGTGTG GACCATGCCG TGGTGCCACC
 841 GGGGGGTGAA GAGCCCCGTA TGCACTGTGC AGTGGATGGC GAGTGGCTGG TGCCCATTGG
 901 GCAGTGCCTG TGCCAGGCAG GCTACGAGAA GGTGGAGGAT GCCTGCCAGG CCTGCTCGCC
 961 TGGATTTTTT AAGTTTGAGG CATCTGAGAG CCCCTGCTTG GAGTGCCCTG AGCACACGCT
1021 GCCATCCCCT GAGGGTGCCA CCTCCTGCGA GTGTGAGGAA GGCTTCTTCC GGGCACCTCA
1081 GGACCCAGCG TCGATGCCTT GCACACGACC CCCCTCCGCC CCACACTACC TCACAGCCGT
1141 GGGCATGGGT GCCAAGGTGG AGCTGCGCTG GACGCCCCCT CAGGACAGCG GGGCCGCGA
1201 GGACATTGTC TACAGCGTCA CCTGCGAACA GTGCTGGCCC GAGTCTGGGG AATGCGGGCC
1261 GTGTGAGGCC AGTGTGCGCT ACTCGGAGCC TCCTCACGGA CTGACCCGCA CCAGTGTGAC
1321 AGTGAGCGAC CTGGAGCCCC ACATGAACTA CACCTTCACC GTGGAGGCCC GCAATGGCGT
1381 CTCAGGCCTG GTAACCAGCC GCAGCTTCCG TACTGCCAGT GTCAGCATCA ACCAGACAGA
1441 GCCCCCCAAG GTGAGGCTGG AGGGCCGCAG CACCACCTCG CTTAGCGTCT CCTGGAGCAT
1501 CCCCCCGCCG CAGCAGAGCC GAGTGTGGAA GTACGAGGTC ACTTACCGCA AGAAGGGAGA
1561 CTCCAACAGC TACAATGTGC GCCGCACCGA GGGTTTCTCC GTGACCCTGG ACGACCTGGC
1621 CCCAGACACC ACCTACCTGG TCCAGGTGCA GGCACTGACG CAGGAGGGCC AGGGGGCCGG
1681 CAGCAAGGTG CACGAATTCC AGACGCTGTC CCCGGAGGGA TCTGGCAACT TGGCGGTGAT
1741 TGGCGGCGTG GCTGTCGGTG TGGTCCTGCT TCTGGTGCTG GCAGGAGTTG GCTTCTTTAT
1801 CCACCGCAGG AGGAAGAACC AGCGTGCCCG CCAGTCCCCG GAGGACGTTT ACTTCTCCAA
1861 GTCAGAACAA CTGAAGCCCC TGAAGACATA CGTGGACCCC CACACATATG AGGACCCCAA
1921 CCAGGCTGTG TTGAAGTTCA CTACCGAGAT CCATCCATCC TGTGTCACTC GGCAGAAGGT
1981 GATCGGAGCA GGAGAGTTTG GGGAGGTGTA CAAGGGCATG CTGAAGACAT CCTCGGGGAA
2041 GAAGGAGGTG CCGGTGGCCA TCAAGACGCT GAAAGCCGGC TACACAGAGA AGCAGCGAGT
2101 GGACTTCCTC GGCGAGGCCG GCATCATGGG CCAGTTCAGC CACCACAACA TCATCCGCCT
2161 AGAGGGCGTC ATCTCCAAAT ACAAGCCCAT GATGATCATC ACTGAGTACA TGGAGAATGG
2221 GGCCCTGGAC AAGTTCCTTC GGGAGAAGGA TGGCGAGTTC AGCGTGCTGC AGCTGGTGGG
2281 CATGCTGCGG GGCATCGCAG CTGGCATGAA GTACCTGGCC AACATGAACT ATGTGCACCG
2341 TGACCTGGCT GCCCGCAACA TCCTCGTCAA CAGCAACCTG GTCTGCAAGG TGTCTGACTT
```

FIG. 2A

```
2401 TGGCCTGTCC CGCGTGCTGG AGGACGACCC CGAGGCCACC TACACCACCA GTGGCGGCAA
2461 GATCCCCATC CGCTGGACCG CCCCGGAGGC CATTTCCTAC CGGAAGTTCA CCTCTGCCAG
2521 CGACGTGTGG AGCTTTGGCA TTGTCATGTG GGAGGTGATG ACCTATGGCG AGCGGCCCTA
2581 CTGGGAGTTG TCCAACCACG AGGTGATGAA AGCCATCAAT GATGGCTTCC GGCTCCCCAC
2641 ACCCATGGAC TGCCCCTCCG CCATCTACCA GCTCATGATG CAGTGCTGGC AGCAGGAGCG
2701 TGCCCGCCGC CCCAAGTTCG CTGACATCGT CAGCATCCTG GACAAGCTCA TTCGTGCCCC
2761 TGACTCCCTC AAGACCCTGG CTGACTTTGA CCCCGCGTG TCTATCCGGC TCCCCAGCAC
2821 GAGCGGCTCG GAGGGGGTGC CCTTCCGCAC GGTGTCCGAG TGGCTGGAGT CCATCAAGAT
2881 GCAGCAGTAT ACGGAGCACT TCATGGCGGC CGGCTACACT GCCATCGAGA AGGTGGTGCA
2941 GATGACCAAC GACGACATCA AGAGGATTGG GGTGCGGCTG CCCGGCCACC AGAAGCGCAT
3001 CGCCTACAGC CTGCTGGGAC TCAAGGACCA GGTGAACACT GTGGGGATCC CCATCTGAGC
3061 CTCGACAGGG CCTGGAGCCC CATCGGCCAA GAATACTTGA AGAAACAGAG TGGCCTCCCT
3121 GCTGTGCCAT GCTGGGCCAC TGGGGACTTT ATTTATTTCT AGTTCTTTCC TCCCCCTGCA
3181 ACTTCCGCTG AGGGGTCTCG GATGACACCC TGGCCTGAAC TGAGGAGATG ACCAGGGATG
3241 CTGGGCTGGG CCCTCTTTCC CTGCGAGACG CACACAGCTG AGCACTTAGC AGGCACCGCC
3301 ACGTCCCAGC ATCCCTGGAG CAGGAGCCCC GCCACAGCCT TCGGACAGAC ATATAGGATA
3361 TTCCCAAGCC GACCTTCCCT CCGCCTTCTC CCACATGAGG CCATCTCAGG AGATGGAGGG
3421 CTTGGCCCAG CGCCAAGTAA ACAGGGTACC TCAAGCCCCA TTTCCTCACA CTAAGAGGGC
3481 AGACTGTGAA CTTGACTGGG TGAGACCCAA AGCGGTCCCT GTCCCTCTAG TGCCTTCTTT
3541 AGACCCTCGG GCCCCATCCT CATCCCTGAC TGGCCAAACC CTTGCTTTCC TGGGCCTTTG
3601 CAAGATGCTT GGTTGTGTTG AGGTTTTTAA ATATATATTT TGTACTTTGT GGAGAAAATG
3661 TGTGTGTGTG GCAGGGGCCC CCGCCAGGGC TGGGGACAGA GGGTGTCAAA CATTCGTGAG
3721 CTGGGGACTC AGGGACCGGT GCTGCAGGAG TGTCCTGCCC ATGCCCAGT CGGCCCCATC
3781 TCTCATCCTT TTGGATAAGT TTCTATTCTG TCAGTGTTAA AGATTTTGTT TTGTTGGACA
3841 TTTTTTTCGA ATCTTAATTT ATTATTTTTT TTATATTTAT TGTTAGAAAA TGACTTATTT
3901 CTGCTCTGGA ATAAAGTTGC AGATGATTCA AAAAAAAAAA AAAA
```

FIG. 2B

| | | | | | |
|---|---|---|---|---|---|
| DRβ1*010101 | DRβ1*010102 | DRβ1*010201 | DRβ1*010202 | DRβ1*0103 | DRβ1*0104 |
| DRβ1*0105 | DRβ1*0106 | DRβ1*0107 | DRβ1*0108 | DRβ1*0109 | DRβ1*0110 |
| DRβ1*030101 | DRβ1*030102 | DRβ1*030201 | DRβ1*030202 | DRβ1*0303 | DRβ1*0304 |
| DRβ1*030501 | DRβ1*030502 | DRβ1*0306 | DRβ1*0307 | DRβ1*0308 | DRβ1*0309 |
| DRβ1*0310 | DRβ1*0311 | DRβ1*0312 | DRβ1*0313 | DRβ1*0314 | DRβ1*0315 |
| DRβ1*0316 | DRβ1*0317 | DRβ1*0318 | DRβ1*0319 | DRβ1*0320 | DRβ1*0321 |
| DRβ1*0322 | DRβ1*0323 | DRβ1*0324 | DRβ1*0325 | DRβ1*040101 | DRβ1*040102 |
| DRβ1*0402 | DRβ1*040301 | DRβ1*040302 | DRβ1*0404 | DRβ1*040501 | DRβ1*040502 |
| DRβ1*040503 | DRβ1*040504 | DRβ1*0406 | DRβ1*040701 | DRβ1*040702 | DRβ1*040703 |
| DRβ1*0408 | DRβ1*0409 | DRβ1*0410 | DRβ1*0411 | DRβ1*0412 | DRβ1*0413 |
| DRβ1*0414 | DRβ1*0415 | DRβ1*0416 | DRβ1*0417 | DRβ1*0418 | DRβ1*0419 |
| DRβ1*0420 | DRβ1*0421 | DRβ1*0422 | DRβ1*0423 | DRβ1*0424 | DRβ1*0425 |
| DRβ1*0426 | DRβ1*0427 | DRβ1*0428 | DRβ1*0429 | DRβ1*0430 | DRβ1*0431 |
| DRβ1*0432 | DRβ1*0433 | DRβ1*0434 | DRβ1*0435 | DRβ1*0436 | DRβ1*0437 |
| DRβ1*0438 | DRβ1*0439 | DRβ1*0440 | DRβ1*0441 | DRβ1*0442 | DRβ1*0443 |
| DRβ1*0444 | DRβ1*0445 | DRβ1*070101 | DRβ1*070102 | DRβ1*0703 | DRβ1*0704 |
| DRβ1*0705 | DRβ1*0706 | DRβ1*0707 | DRβ1*080101 | DRβ1*080102 | DRβ1*080201 |
| DRβ1*080202 | DRβ1*080203 | DRβ1*080302 | DRβ1*080401 | DRβ1*080402 | DRβ1*080403 |
| DRβ1*080404 | DRβ1*0805 | DRβ1*0806 | DRβ1*0807 | DRβ1*0808 | DRβ1*0809 |
| DRβ1*0810 | DRβ1*0811 | DRβ1*0812 | DRβ1*0813 | DRβ1*0814 | DRβ1*0815 |
| DRβ1*0816 | DRβ1*0817 | DRβ1*0818 | DRβ1*0819 | DRβ1*0820 | DRβ1*0821 |
| DRβ1*0822 | DRβ1*0823 | DRβ1*0824 | DRβ1*090102 | DRβ1*0902 | DRβ1*100101 |
| DRβ1*100102 | DRβ1*110101 | DRβ1*110102 | DRβ1*110103 | DRβ1*110104 | DRβ1*1102 |
| DRβ1*1103 | DRβ1*110401 | DRβ1*110402 | DRβ1*1105 | DRβ1*110601 | DRβ1*110602 |
| DRβ1*1107 | DRβ1*110801 | DRβ1*110802 | DRβ1*1109 | DRβ1*1110 | DRβ1*1111 |
| DRβ1*111201 | DRβ1*111202 | DRβ1*1113 | DRβ1*1114 | DRβ1*1115 | DRβ1*1116 |
| DRβ1*1117 | DRβ1*1118 | DRβ1*1119 | DRβ1*1120 | DRβ1*1121 | DRβ1*1122 |
| DRβ1*1123 | DRβ1*1124 | DRβ1*1125 | DRβ1*1126 | DRβ1*112701 | DRβ1*112702 |
| DRβ1*1128 | DRβ1*1129 | DRβ1*1130 | DRβ1*1131 | DRβ1*1132 | DRβ1*1133 |
| DRβ1*1134 | DRβ1*1135 | DRβ1*1136 | DRβ1*1137 | DRβ1*1138 | DRβ1*1139 |
| DRβ1*1140 | DRβ1*1141 | DRβ1*1142 | DRβ1*1143 | DRβ1*120101 | DRβ1*120102 |
| DRβ1*120201 | DRβ1*120202 | DRβ1*120302 | DRβ1*1204 | DRβ1*1205 | DRβ1*1206 |
| DRβ1*1207 | DRβ1*1208 | DRβ1*130101 | DRβ1*130102 | DRβ1*130103 | DRβ1*130201 |
| DRβ1*130202 | DRβ1*130301 | DRβ1*130302 | DRβ1*1304 | DRβ1*1305 | DRβ1*1306 |
| DRβ1*130701 | DRβ1*130702 | DRβ1*1308 | DRβ1*1309 | DRβ1*1310 | DRβ1*1311 |
| DRβ1*1312 | DRβ1*1313 | DRβ1*131401 | DRβ1*131402 | DRβ1*1315 | DRβ1*1316 |
| DRβ1*1317 | DRβ1*1318 | DRβ1*1319 | DRβ1*1320 | DRβ1*1321 | DRβ1*1322 |
| DRβ1*1323 | DRβ1*1324 | DRβ1*1325 | DRβ1*1326 | DRβ1*1327 | DRβ1*1328 |
| DRβ1*1329 | DRβ1*1330 | DRβ1*1331 | DRβ1*1332 | DRβ1*1333 | DRβ1*1334 |
| DRβ1*1335 | DRβ1*1336 | DRβ1*1337 | DRβ1*1338 | DRβ1*1339 | DRβ1*1340 |
| DRβ1*1341 | DRβ1*1342 | DRβ1*1343 | DRβ1*1344 | DRβ1*1345 | DRβ1*1346 |
| DRβ1*1347 | DRβ1*1348 | DRβ1*1349 | DRβ1*1350 | DRβ1*1351 | DRβ1*1352 |
| DRβ1*1353 | DRβ1*1354 | DRβ1*1355 | DRβ1*140101 | DRβ1*140102 | DRβ1*1402 |
| DRβ1*1403 | DRβ1*1404 | DRβ1*140501 | DRβ1*140502 | DRβ1*1406 | DRβ1*140701 |
| DRβ1*140702 | DRβ1*1408 | DRβ1*1409 | DRβ1*1410 | DRβ1*1411 | DRβ1*1412 |
| DRβ1*1413 | DRβ1*1414 | DRβ1*1415 | DRβ1*1416 | DRβ1*1417 | DRβ1*1418 |
| DRβ1*1419 | DRβ1*1420 | DRβ1*1421 | DRβ1*1422 | DRβ1*1423 | DRβ1*1424 |
| DRβ1*1425 | DRβ1*1426 | DRβ1*1427 | DRβ1*1428 | DRβ1*1429 | DRβ1*1430 |
| DRβ1*1431 | DRβ1*1432 | DRβ1*1433 | DRβ1*1434 | DRβ1*1435 | DRβ1*1436 |
| DRβ1*1437 | DRβ1*1438 | DRβ1*1439 | DRβ1*1440 | DRβ1*1441 | DRβ1*1442 |
| DRβ1*1443 | DRβ1*1444 | DRβ1*1445 | DRβ1*1446 | DRβ1*150101 | DRβ1*150102 |
| DRβ1*150103 | DRβ1*150104 | DRβ1*150201 | DRβ1*150202 | DRβ1*150203 | DRβ1*1503 |

FIG. 3A

| | | | | | |
|---|---|---|---|---|---|
| DRβ1*1504 | DRβ1*1505 | DRβ1*1506 | DRβ1*1507 | DRβ1*1508 | DRβ1*1509 |
| DRβ1*1510 | DRβ1*1511 | DRβ1*1512 | DRβ1*1513 | DRβ1*160101 | DRβ1*160102 |
| DRβ1*160201 | DRβ1*160202 | DRβ1*1603 | DRβ1*1604 | DRβ1*1605 | DRβ1*1607 |
| DRβ1*1608 | DRβ2*0101 | DRβ3*010101 | DRβ3*01010201 | | DRβ3*01010202 |
| DRβ3*010103 | DRβ3*010104 | DRβ3*0102 | DRβ3*0103 | DRβ3*0104 | DRβ3*0105 |
| DRβ3*0106 | DRβ3*0107 | DRβ3*0108 | DRβ3*0109 | DRβ3*0110 | DRβ3*0201 |
| DRβ3*020201 | DRβ3*020202 | DRβ3*020203 | DRβ3*020204 | DRβ3*0203 | DRβ3*0204 |
| DRβ3*0205 | DRβ3*0206 | DRβ3*0207 | DRβ3*0208 | DRβ3*0209 | DRβ3*0210 |
| DRβ3*0211 | DRβ3*0212 | DRβ3*0213 | DRβ3*0214 | DRβ3*0215 | DRβ3*0216 |
| DRβ3*0217 | DRβ3*030101 | DRβ3*030102 | DRβ3*0302 | DRβ3*0303 | DRβ4*010101 |
| DRβ4*0102 | DRβ4*01030101 | | DRβ4*01030102N | | DRβ4*010302 |
| DRβ4*010303 | DRβ4*010304 | DRβ4*0104 | DRβ4*0105 | DRβ4*0106 | DRβ4*0201N |
| DRβ4*0301N | DRβ5*010101 | DRβ5*010102 | DRβ5*0102 | DRβ5*0103 | DRβ5*0104 |
| DRβ5*0105 | DRβ5*0106 | DRβ5*0107 | DRβ5*0108N | DRβ5*0109 | DRβ5*0110N |
| DRβ5*0111 | DRβ5*0112 | DRβ5*0202 | DRβ5*0203 | DRβ5*0204 | DRβ5*0205 |
| DRβ6*0101 | DRβ6*0201 | DRβ6*0202 | DRβ7*010101 | DRβ7*010102 | DRβ8*0101 |
| DRβ9*0101 | | | | | |

FIG. 3B

| | | | | | | |
|---|---|---|---|---|---|---|
| A*010101 | A*010102 | A*0102 | A*0103 | A*0104N | A*0106 | A*0107 |
| A*0108 | A*0109 | A*020101 | A*020102 | A*020103 | A*020104 | A*020105 |
| A*020106 | A*020107 | A*020108 | A*020109 | A*0202 | A*0203 | A*0204 |
| A*0205 | A*0206 | A*0207 | A*0208 | A*0209 | A*0210 | A*0211 |
| A*0212 | A*0213 | A*0214 | A*0215N | A*0216 | A*021701 | A*021702 |
| A*0218 | A*0219 | A*022001 | A*022002 | A*0221 | A*0222 | A*0224 |
| A*0225 | A*0226 | A*0227 | A*0228 | A*0229 | A*0230 | A*0231 |
| A*0232N | A*0233 | A*0234 | A*0235 | A*0236 | A*0237 | A*0238 |
| A*0239 | A*0240 | A*0241 | A*0242 | A*0243N | A*0244 | A*0245 |
| A*0246 | A*0247 | A*0248 | A*0249 | A*0250 | A*0251 | A*0252 |
| A*0253N | A*0254 | A*0255 | A*0256 | A*0257 | A*0258 | A*0259 |
| A*0260 | A*0261 | A*0262 | A*03010101 | A*03010102N | A*030102 | A*030103 |
| A*0302 | A*0303N | A*0304 | A*0305 | A*0306 | A*0307 | A*0308 |
| A*0309 | A*0310 | A*0311N | A*110101 | A*110102 | A*1102 | A*1103 |
| A*1104 | A*1105 | A*1106 | A*1107 | A*1108 | A*1109 | A*1110 |
| A*1111 | A*1112 | A*1113 | A*1114 | A*2301 | A*2302 | A*2303 |
| A*2304 | A*2305 | A*2306 | A*2307N | A*2308N | A*2309 | |
| A*24020101 | A*24020102L | A*240202 | A*240203 | A*240204 | A*240301 | A*240302 |
| A*2404 | A*2405 | A*2406 | A*2407 | A*2408 | A*2409N | A*2410 |
| A*2411N | A*2413 | A*2414 | A*2415 | A*2417 | A*2418 | A*2419 |
| A*2420 | A*2421 | A*2422 | A*2423 | A*2424 | A*2425 | A*2426 |
| A*2427 | A*2428 | A*2429 | A*2430 | A*2431 | A*2432 | A*2433 |
| A*2434 | A*2435 | A*2436N | A*2437 | A*2438 | A*2501 | A*2502 |
| A*2503 | A*2504 | A*2601 | A*2602 | A*2603 | A*2604 | A*2605 |
| A*2606 | A*2607 | A*2608 | A*2609 | A*2610 | A*2611N | A*2612 |
| A*2613 | A*2614 | A*2615 | A*2616 | A*2617 | A*2618 | |
| A*29010101 | A*29010102N | A*290201 | A*290202 | A*2903 | A*2904 | A*2905 |
| A*2906 | A*2907 | A*2908N | A*2909 | A*3001 | A*3002 | A*3003 |
| A*3004 | A*3006 | A*3007 | A*3008 | A*3009 | A*3010 | A*3011 |
| A*3012 | A*310102 | A*3102 | A*3103 | A*3104 | A*3105 | A*3106 |
| A*3107 | A*3108 | A*3109 | A*3201 | A*3202 | A*3203 | A*3204 |
| A*3205 | A*3206 | A*3207 | A*3301 | A*3303 | A*3304 | A*3305 |
| A*3306 | A*3307 | A*3401 | A*3402 | A*3403 | A*3404 | A*3405 |
| A*3601 | A*3602 | A*3603 | A*3604 | A*4301 | A*6601 | A*6602 |
| A*6603 | A*6604 | A*680101 | A*680102 | A*6802 | A*680301 | A*680302 |
| A*6804 | A*6805 | A*6806 | A*6807 | A*6808 | A*6809 | A*6810 |
| A*6811N | A*6812 | A*6813 | A*6814 | A*6815 | A*6816 | A*6817 |
| A*6818N | A*6819 | A*6820 | A*6821 | A*6822 | A*6823 | A*6824 |
| A*6901 | A*7401 | A*7402 | A*7403 | A*7404 | A*7405 | A*7406 |
| A*7407 | A*7408 | A*7409 | A*8001 | B*070201 | B*070202 | B*070203 |
| B*0703 | B*0704 | B*0705 | B*0706 | B*0707 | B*0708 | B*0709 |
| B*0710 | B*0711 | B*0712 | B*0713 | B*0714 | B*0715 | B*0716 |
| B*0717 | B*0718 | B*0719 | B*0720 | B*0721 | B*0722 | B*0723 |
| B*0724 | B*0725 | B*0726 | B*0727 | B*0728 | B*0729 | B*0730 |
| B*0731 | B*0801 | B*0802 | B*0803 | B*0804 | B*0805 | B*0806 |
| B*0807 | B*0808N | B*0809 | B*0810 | B*0811 | B*0812 | B*0813 |
| B*0814 | B*0815 | B*0816 | B*0817 | B*0818 | B*0819N | B*1301 |
| B*1302 | B*1303 | B*1304 | B*1306 | B*1307N | B*1308 | B*1309 |
| B*1310 | B*1311 | B*1401 | B*1402 | B*1403 | B*1404 | B*1405 |
| B*140601 | B*140602 | B*15010101 | B*15010102N | B*150102 | B*150103 | B*150104 |
| B*1502 | B*1503 | B*1504 | B*1505 | B*1506 | B*1507 | B*1508 |
| B*1509 | B*1510 | B*151101 | B*151102 | B*1512 | B*1513 | B*1514 |

FIG. 4A

| | | | | | | |
|---|---|---|---|---|---|---|
| B*1515 | B*1516 | B*15170101 | B*15170102 | B*1518 | B*1519 | B*1520 |
| B*1521 | B*1523 | B*1524 | B*1525 | B*1526N | B*1527 | B*1528 |
| B*1529 | B*1530 | B*1531 | B*1532 | B*1533 | B*1534 | B*1535 |
| B*1536 | B*1537 | B*1538 | B*1539 | B*1540 | B*1542 | B*1543 |
| B*1544 | B*1545 | B*1546 | B*1547 | B*1548 | B*1549 | B*1550 |
| B*1551 | B*1552 | B*1553 | B*1554 | B*1555 | B*1556 | B*1557 |
| B*1558 | B*1560 | B*1561 | B*1562 | B*1563 | B*1564 | B*1565 |
| B*1566 | B*1567 | B*1568 | B*1569 | B*1570 | B*1571 | B*1572 |
| B*1573 | B*1574 | B*1575 | B*1576 | B*180101 | B*180102 | B*1802 |
| B*1803 | B*1804 | B*1805 | B*1806 | B*1807 | B*1808 | B*1809 |
| B*1810 | B*1811 | B*1812 | B*1813 | B*1814 | B*1815 | B*1817N |
| B*1818 | B*2701 | B*2702 | B*2703 | B*2704 | B*270502 | B*270503 |
| B*270504 | B*270505 | B*270506 | B*2706 | B*2707 | B*2708 | B*2709 |
| B*2710 | B*2711 | B*2712 | B*2713 | B*2714 | B*2715 | B*2716 |
| B*2717 | B*2718 | B*2719 | B*2720 | B*2721 | B*2723 | B*2724 |
| B*2725 | B*350101 | B*350102 | B*3502 | B*3503 | B*3504 | B*3505 |
| B*3506 | B*3507 | B*3508 | B*350901 | B*350902 | B*3510 | B*3511 |
| B*3512 | B*3513 | B*3514 | B*3515 | B*3516 | B*3517 | B*3518 |
| B*3519 | B*3520 | B*3521 | B*3522 | B*3523 | B*3524 | B*3525 |
| B*3526 | B*3527 | B*3528 | B*3529 | B*3530 | B*3531 | B*3532 |
| B*3533 | B*3534 | B*3535 | B*3536 | B*3537 | B*3538 | B*3539 |
| B*3540N | B*3541 | B*3542 | B*3543 | B*3544 | B*3545 | B*3701 |
| B*3702 | B*3703N | B*3704 | B*3705 | B*3801 | B*380201 | B*380202 |
| B*3803 | B*3804 | B*3805 | B*3806 | B*3807 | B*3808 | B*3809 |
| B*390101 | B*390103 | B*390104 | B*390201 | B*390202 | B*3903 | B*3904 |
| B*3905 | B*390601 | B*390602 | B*3907 | B*3908 | B*3909 | B*3910 |
| B*3911 | B*3912 | B*3913 | B*3914 | B*3915 | B*3916 | B*3917 |
| B*3918 | B*3919 | B*3920 | B*3922 | B*3923 | B*3924 | B*3925N |
| B*3926 | B*3927 | B*400101 | B*400102 | B*400103 | B*4002 | B*4003 |
| B*4004 | B*4005 | B*40060101 | B*40060102 | B*4007 | B*4008 | B*4009 |
| B*4010 | B*4011 | B*4012 | B*4013 | B*401401 | B*401402 | B*4015 |
| B*4016 | B*4018 | B*4019 | B*4020 | B*4021 | B*4022N | B*4023 |
| B*4024 | B*4025 | B*4026 | B*4027 | B*4028 | B*4029 | B*4030 |
| B*4031 | B*4032 | B*4033 | B*4034 | B*4035 | B*4036 | B*4037 |
| B*4038 | B*4039 | B*4040 | B*4042 | B*4043 | B*4044 | B*4045 |
| B*4101 | B*4102 | B*4103 | B*4104 | B*4105 | B*4106 | B*4201 |
| B*4202 | B*4204 | B*4205 | B*44020101 | B*440201025 | B*440202 | B*440203 |
| B*440301 | B*440302 | B*4404 | B*4405 | B*4406 | B*4407 | B*4408 |
| B*4409 | B*4410 | B*4411 | B*4412 | B*4413 | B*4414 | B*4415 |
| B*4416 | B*4417 | B*4418 | B*4419N | B*4420 | B*4421 | B*4422 |
| B*4423N | B*4424 | B*4425 | B*4426 | B*4427 | B*4428 | B*4429 |
| B*4430 | B*4431 | B*4432 | B*4433 | B*4434 | B*4435 | B*4501 |
| B*4502 | B*4503 | B*4504 | B*4505 | B*4506 | B*4601 | B*4602 |
| B*47010101 | B*47010102 | B*4702 | B*4703 | B*4704 | B*4801 | B*4802 |
| B*4803 | B*4804 | B*4805 | B*4806 | B*4807 | B*4901 | B*4902 |
| B*4903 | B*5001 | B*5002 | B*5004 | B*510101 | B*510102 | B*510103 |
| B*510104 | B*510105 | B*510201 | B*510202 | B*5103 | B*5104 | B*5105 |
| B*5106 | B*5107 | B*5108 | B*5109 | B*5110 | B*5111N | B*5112 |
| B*511301 | B*511302 | B*5114 | B*5115 | B*5116 | B*5117 | B*5118 |
| B*5119 | B*5120 | B*5121 | B*5122 | B*5123 | B*5124 | B*5126 |
| B*5127N | B*5128 | B*5129 | B*5130 | B*5131 | B*5132 | B*5133 |
| B*5134 | B*520101 | B*520102 | B*520103 | B*520104 | B*5202 | B*5203 |

FIG. 4B

| | | | | | | |
|---|---|---|---|---|---|---|
| B*5204 | B*5205 | B*5301 | B*5302 | B*5303 | B*5304 | B*5305 |
| B*5306 | B*5307 | B*5308 | B*5309 | B*5401 | B*5402 | B*5501 |
| B*5502 | B*5503 | B*5504 | B*5505 | B*5507 | B*5508 | B*5509 |
| B*5510 | B*5511 | B*5512 | B*5513 | B*5601 | B*5602 | B*5603 |
| B*5604 | B*560501 | B*560502 | B*5606 | B*5607 | B*5608 | B*5609 |
| B*5610 | B*5611 | B*570101 | B*570102 | B*5702 | B*570301 | B*570302 |
| B*5704 | B*5705 | B*5706 | B*5707 | B*5708 | B*5709 | B*5801 |
| B*5802 | B*5804 | B*5805 | B*5806 | B*5807 | B*5808 | B*5901 |
| B*670101 | B*670102 | B*6702 | B*7301 | B*7801 | B*780201 | B*780202 |
| B*7803 | B*7804 | B*7805 | B*8101 | B*8201 | B*8202 | B*8301 |

FIG. 4C

HLA-A1

| Rank | Sequence Reference | Subsequence Residue Listing | Score |
|---|---|---|---|
| 1 | SEQ ID NO:2, residues 783-791 | WTAPEAISY | 62.500 |
| 2 | SEQ ID NO:2, residues 578-586 | KSEQLKPLK | 54.000 |
| 3 | SEQ ID NO:2, residues 436-444 | QTEPPKVRL | 45.000 |
| 4 | SEQ ID NO:2, residues 694-702 | YMENGALDK | 45.000 |
| 5 | SEQ ID NO:2, residues 677-685 | RLEGVISKY | 45.000 |
| 6 | SEQ ID NO:2, residues 909-917 | VSEWLESIK | 27.000 |
| 7 | SEQ ID NO:2, residues 570-578 | SPEDVYFSK | 22.500 |
| 8 | SEQ ID NO:2, residues 385-393 | YSEPPHGLT | 13.500 |
| 9 | SEQ ID NO:2, residues 59-67 | MNDMPIYMY | 12.500 |
| 10 | SEQ ID NO:2, residues 115-123 | CKETFNLYY | 11.250 |
| 11 | SEQ ID NO:2, residues 621-629 | AGEFGEVYK | 9.000 |
| 12 | SEQ ID NO:2, residues 785-793 | APEAISYRK | 9.000 |
| 13 | SEQ ID NO:2, residues 95-103 | FIELKFTVR | 9.000 |
| 14 | SEQ ID NO:2, residues 401-409 | DLEPHMNYT | 9.000 |
| 15 | SEQ ID NO:2, residues 306-314 | SCECEEGFF | 9.000 |
| 16 | SEQ ID NO:2, residues 900-908 | GSEGVPFRT | 6.750 |
| 17 | SEQ ID NO:2, residues 285-293 | ASESPCLEC | 6.750 |
| 18 | SEQ ID NO:2, residues 275-283 | ACSPGFFKF | 5.000 |
| 19 | SEQ ID NO:2, residues 308-316 | ECEEGFFRA | 4.500 |
| 20 | SEQ ID NO:2, residues 921-929 | YTEHFMAAG | 4.500 |

Fig. 5

HLA-A3

| Rank | Sequence Reference | Subsequence Residue Listing | Score |
|---|---|---|---|
| 1 | SEQ ID NO:2, residues 191-199 | LLSVRVYYK | 180.000 |
| 2 | SEQ ID NO:2, residues 630-638 | GMLKTSSGK | 90.000 |
| 3 | SEQ ID NO:2, residues 260-268 | CLCQAGYEK | 60.000 |
| 4 | SEQ ID NO:2, residues 694-702 | YMENGALDK | 40.000 |
| 5 | SEQ ID NO:2, residues 339-347 | GMGAKVELR | 36.000 |
| 6 | SEQ ID NO:2, residues 647-655 | TLKAGYTEK | 20.000 |
| 7 | SEQ ID NO:2, residues 917-925 | KMQQYTEHF | 18.000 |
| 8 | SEQ ID NO:2, residues 420-428 | GLVTSRSFR | 18.000 |
| 9 | SEQ ID NO:2, residues 677-685 | RLEGVISKY | 13.500 |
| 10 | SEQ ID NO:2, residues 850-858 | MMQCWQQER | 12.000 |
| 11 | SEQ ID NO:2, residues 713-721 | VLQLVGMLR | 12.000 |
| 12 | SEQ ID NO:2, residues 948-956 | GVRLPGHQK | 9.000 |
| 13 | SEQ ID NO:2, residues 699-707 | ALDKFLREK | 9.000 |
| 14 | SEQ ID NO:2, residues 750-758 | NLVCKVSDF | 9.000 |
| 15 | SEQ ID NO:2, residues 190-198 | ALLSVRVYY | 9.000 |
| 16 | SEQ ID NO:2, residues 938-946 | QMTNDDIKR | 8.000 |
| 17 | SEQ ID NO:2, residues 754-762 | KVSDFGLSR | 7.200 |
| 18 | SEQ ID NO:2, residues 820-828 | ELSNHEVMK | 6.000 |
| 19 | SEQ ID NO:2, residues 465-473 | RVWKYEVTY | 6.000 |
| 20 | SEQ ID NO:2, residues 631-639 | MLKTSSGKK | 6.000 |

Fig. 6

HLA-B7

| Rank | Sequence Reference | Subsequence Residue Listing | Score |
|---|---|---|---|
| 1 | SEQ ID NO:2, residues 5-13 | AARACFALL | 360.000 |
| 2 | SEQ ID NO:2, residues 413-421 | EARNGVSGL | 120.000 |
| 3 | SEQ ID NO:2, residues 327-335 | RPPSAPHYL | 80.000 |
| 4 | SEQ ID NO:2, residues 46-54 | HPYGKGWDL | 80.000 |
| 5 | SEQ ID NO:2, residues 36-44 | AAGGELGWL | 36.000 |
| 6 | SEQ ID NO:2, residues 23-31 | AAQGKEVVL | 36.000 |
| 7 | SEQ ID NO:2, residues 838-846 | TPMDCPSAI | 24.000 |
| 8 | SEQ ID NO:2, residues 842-850 | CPSAIYQLM | 20.000 |
| 9 | SEQ ID NO:2, residues 640-648 | EVPVAIKTL | 20.000 |
| 10 | SEQ ID NO:2, residues 540-548 | GVAVGVVLL | 20.000 |
| 11 | SEQ ID NO:2, residues 712-720 | SVLQLVGML | 20.000 |
| 12 | SEQ ID NO:2, residues 541-549 | VAVGVVLLL | 12.000 |
| 13 | SEQ ID NO:2, residues 828-836 | KAINDGFRL | 12.000 |
| 14 | SEQ ID NO:2, residues 876-884 | RAPDSLKTL | 12.000 |
| 15 | SEQ ID NO:2, residues 10-18 | FALLWGCAL | 12.000 |
| 16 | SEQ ID NO:2, residues 24-32 | AQGKEVVLL | 12.000 |
| 17 | SEQ ID NO:2, residues 4-12 | QAARACFAL | 12.000 |
| 18 | SEQ ID NO:2, residues 338-346 | VGMGAKVEL | 12.000 |
| 19 | SEQ ID NO:2, residues 215-223 | IAGSDAPSL | 12.000 |
| 20 | SEQ ID NO:2, residues 719-727 | MLRGIAAGM | 10.000 |

Fig. 7

HLA-B44

| Rank | Sequence Reference | Subsequence Residue Listing | Score |
|---|---|---|---|
| 1 | SEQ ID NO:2, residues 148-156 | DEITVSSDF | 900.000 |
| 2 | SEQ ID NO:2, residues 913-921 | LESIKMQQY | 270.000 |
| 3 | SEQ ID NO:2, residues 695-703 | MENGALDKF | 202.500 |
| 4 | SEQ ID NO:2, residues 922-930 | TEHFMAAGY | 180.000 |
| 5 | SEQ ID NO:2, residues 495-503 | DDLAPDTTY | 135.000 |
| 6 | SEQ ID NO:2, residues 764-772 | LEDDPEATY | 120.000 |
| 7 | SEQ ID NO:2, residues 662-670 | GEAGIMGQF | 120.000 |
| 8 | SEQ ID NO:2, residues 856-864 | QERARRPKF | 60.000 |
| 9 | SEQ ID NO:2, residues 400-408 | SDLEPHMNY | 60.000 |
| 10 | SEQ ID NO:2, residues 639-647 | KEVPVAIKT | 54.000 |
| 11 | SEQ ID NO:2, residues 402-410 | LEPHMNYTF | 40.000 |
| 12 | SEQ ID NO:2, residues 721-729 | RGIAAGMKY | 33.750 |
| 13 | SEQ ID NO:2, residues 126-134 | SDLDYGTNF | 30.000 |
| 14 | SEQ ID NO:2, residues 596-604 | DPNQAVLKF | 20.250 |
| 15 | SEQ ID NO:2, residues 606-614 | TEIHPSCVT | 20.000 |
| 16 | SEQ ID NO:2, residues 1-9 | MELQAARAC | 18.000 |
| 17 | SEQ ID NO:2, residues 189-197 | VALLSVRVY | 18.000 |
| 18 | SEQ ID NO:2, residues 783-791 | WTAPEAISY | 18.000 |
| 19 | SEQ ID NO:2, residues 786-794 | PEAISYRKF | 18.000 |
| 20 | SEQ ID NO:2, residues 579-587 | SEQLKPLKT | 18.000 |

Fig. 8

| DRB_0101 | Threshold for 3% with score: 0.14 | Highest Score Achievable by any peptide: 6 |
|---|---|---|

| Rank | Sequence Reference | Subsequence Residue Listing | Score | % of Highest Score |
|---|---|---|---|---|
| 1 | SEQ ID NO:1, residues 10-18 | FALLWGCAL | 2.1000 | 35.00 |
| 2 | SEQ ID NO:1, residues 717-725 | VGMLRGIAA | 2.1000 | 35.00 |
| 3 | SEQ ID NO:1, residues 675-683 | IIRLEGVIS | 1.8000 | 30.00 |
| 4 | SEQ ID NO:1, residues 548-556 | LLVLAGVGF | 1.4000 | 23.33 |
| 5 | SEQ ID NO:1, residues 545-553 | VVLLLVLAG | 1.4000 | 23.33 |
| 6 | SEQ ID NO:1, residues 65-73 | YMYSVCNVM | 1.3800 | 23.00 |
| 7 | SEQ ID NO:1, residues 484-492 | VRRTEGFSV | 1.2000 | 20.00 |
| 8 | SEQ ID NO:1, residues 834-842 | FRLPTPMDC | 1.1900 | 19.83 |
| 9 | SEQ ID NO:1, residues 524-532 | FQTLSPEGS | 1.0000 | 16.67 |
| 10 | SEQ ID NO:1, residues 29-37 | VVLLDFAAA | 0.9000 | 15.00 |
| 11 | SEQ ID NO:1, residues 334-342 | YLTAVGMGA | 0.7900 | 13.17 |
| 12 | SEQ ID NO:1, residues 535-543 | LAVIGGVAV | 0.7000 | 11.67 |
| 13 | SEQ ID NO:1, residues 536-544 | VIGGVAVGV | 0.6000 | 10.00 |
| 14 | SEQ ID NO:1, residues 14-22 | WGCALAAAA | 0.5000 | 8.33 |
| 15 | SEQ ID NO:1, residues 182-190 | FQDIGACVA | 0.4000 | 6.67 |
| 16 | SEQ ID NO:1, residues 280-288 | FFKFEASES | 0.3800 | 6.33 |
| 17 | SEQ ID NO:1, residues 383-391 | VRYSEPPHG | 0.3700 | 6.17 |
| 18 | SEQ ID NO:1, residues 660-668 | FLGEAGIMG | 0.3000 | 5.00 |
| 19 | SEQ ID NO:1, residues 2-10 | MELQAARAC | 0.2900 | 4.83 |
| 20 | SEQ ID NO:1, residues 546-554 | VLLLVLAGV | 0.2000 | 3.33 |

Fig. 9

| ALLELE: DRB1_0301 | Threshold for 3% with score: 2.96 | Highest Score Achievable by any peptide: 9.5 | | |
|---|---|---|---|---|
| Rank | Subsequence Residue Listing | Sequence Reference | Score | % of Highest Score |
| 1 | SEQ ID NO:1, residues 58-66 | IMNDMPIYM | 5.9000 | 62.11 |
| 2 | SEQ ID NO:1, residues 383-391 | VRYSEPPHG | 5.3000 | 55.79 |
| 3 | SEQ ID NO:1, residues 549-557 | LVLAGVGFF | 5.3000 | 55.79 |
| 4 | SEQ ID NO:1, residues 805-813 | IVMWEVMTY | 5.1000 | 53.68 |
| 5 | SEQ ID NO:1, residues 545-553 | VVLLLVLAG | 4.9000 | 51.58 |
| 6 | SEQ ID NO:1, residues 30-38 | VLLDFAAAG | 4.7000 | 49.47 |
| 7 | SEQ ID NO:1, residues 145-153 | IAPDEITVS | 4.3000 | 45.26 |
| 8 | SEQ ID NO:1, residues 360-368 | IVYSVTCEQ | 4.2000 | 44.21 |
| 9 | SEQ ID NO:1, residues 893-901 | IRLPSTSGS | 4.1700 | 43.89 |
| 10 | SEQ ID NO:1, residues 81-89 | LRTNWVYRG | 3.9500 | 41.58 |
| 11 | SEQ ID NO:1, residues 338-346 | VGMGAKVEL | 3.8600 | 40.63 |
| 12 | SEQ ID NO:1, residues 497-505 | LAPDTTYLV | 3.6500 | 38.42 |
| 13 | SEQ ID NO:1, residues 676-684 | IRLEGVISK | 3.6000 | 37.89 |
| 14 | SEQ ID NO:1, residues 746-754 | LVNSNLVCK | 3.5000 | 36.84 |
| 15 | SEQ ID NO:1, residues 94-102 | IFIELKFTV | 3.4000 | 35.79 |
| 16 | SEQ ID NO:1, residues 716-724 | LVGMLRGIA | 3.4000 | 35.79 |
| 17 | SEQ ID NO:1, residues 681-689 | VISKYKPMM | 3.4000 | 35.79 |
| 18 | SEQ ID NO:1, residues 719-727 | MLRGIAAGM | 3.3000 | 34.74 |
| 19 | SEQ ID NO:1, residues 736-744 | VHRDLAARN | 3.2000 | 33.68 |
| 20 | SEQ ID NO:1, residues 868-876 | VSILDKLIR | 3.2000 | 33.68 |

Fig. 10

| ALLELE: DRB1_0401 | Threshold for 3% with score: 1.48 | Highest Score Achievable by any peptide: 8.6 | | |
|---|---|---|---|---|
| Rank | Subsequence Residue Listing | Sequence Reference | Score | % of Highest Score |
| 1 | SEQ ID NO:1, residues 360-368 | IVYSVTCEQ | 5.1000 | 59.30 |
| 2 | SEQ ID NO:1, residues 676-684 | IRLEGVISK | 4.3800 | 50.93 |
| 3 | SEQ ID NO:1, residues 467-475 | WKYEVTYRK | 3.8000 | 44.19 |
| 4 | SEQ ID NO:1, residues 545-553 | VVLLLVLAG | 3.5000 | 40.70 |
| 5 | SEQ ID NO:1, residues 745-753 | ILVNSNLVC | 3.4000 | 39.53 |
| 6 | SEQ ID NO:1, residues 281-289 | FKFEASESP | 3.3000 | 38.37 |
| 7 | SEQ ID NO:1, residues 406-414 | MNYTFTVEA | 3.2800 | 38.14 |
| 8 | SEQ ID NO:1, residues 893-901 | IRLPSTSGS | 3.0000 | 34.88 |
| 9 | SEQ ID NO:1, residues 524-532 | FQTLSPEGS | 2.9000 | 33.72 |
| 10 | SEQ ID NO:1, residues 65-73 | YMYSVCNVM | 2.9000 | 33.72 |
| 11 | SEQ ID NO:1, residues 727-735 | MKYLANMNY | 2.8000 | 32.56 |
| 12 | SEQ ID NO:1, residues 936-944 | VVQMTNDDI | 2.7000 | 31.40 |
| 13 | SEQ ID NO:1, residues 346-354 | LRWTPPQDS | 2.6000 | 30.23 |
| 14 | SEQ ID NO:1, residues 834-842 | FRLPTPMDC | 2.4000 | 27.91 |
| 15 | SEQ ID NO:1, residues 758-766 | FGLSRVLED | 2.2000 | 25.58 |
| 16 | SEQ ID NO:1, residues 608-616 | IHPSCVTRQ | 2.2000 | 25.58 |
| 17 | SEQ ID NO:1, residues 418-426 | VSGLVTSRS | 2.1000 | 24.42 |
| 18 | SEQ ID NO:1, residues 847-855 | YQLMMQCWQ | 2.1000 | 24.42 |
| 19 | SEQ ID NO:1, residues 729-737 | YLANMNYVH | 2.0800 | 24.19 |
| 20 | SEQ ID NO:1, residues 805-813 | IVMWEVMTY | 2.0000 | 23.26 |

Fig. 11

| ALLELE: DRB1_0701 | Threshold for 3% with score: 4.1 | Highest Score Achievable by any peptide: 11.6 | | |
|---|---|---|---|---|
| Rank | Subsequence Residue Listing | Sequence Reference | Score | % of Highest Score |
| 1 | SEQ ID NO:1, residues 574-582 | VYFSKSEQL | 7.1000 | 61.21 |
| 2 | SEQ ID NO:1, residues 484-492 | VRRTEGFSV | 6.8000 | 58.62 |
| 3 | SEQ ID NO:1, residues 65-73 | YMYSVCNVM | 6.8000 | 58.62 |
| 4 | SEQ ID NO:1, residues 781-789 | IRWTAPEAI | 6.4000 | 55.17 |
| 5 | SEQ ID NO:1, residues 421-429 | LVTSRSFRT | 5.7000 | 49.14 |
| 6 | SEQ ID NO:1, residues 543-551 | VGVVLLLVL | 5.6000 | 48.28 |
| 7 | SEQ ID NO:1, residues 283-291 | FEASESPCL | 5.4000 | 46.55 |
| 8 | SEQ ID NO:1, residues 670-679 | FSHHNIIRL | 5.3000 | 45.69 |
| 9 | SEQ ID NO:1, residues 803-811 | FGIVMWEVM | 4.9000 | 42.24 |
| 10 | SEQ ID NO:1, residues 819-827 | WELSNHEVM | 4.7000 | 40.52 |
| 11 | SEQ ID NO:1, residues 925-933 | FMAAGYTAI | 4.4000 | 37.93 |
| 12 | SEQ ID NO:1, residues 805-813 | IVMWEVMTY | 4.4000 | 37.93 |
| 13 | SEQ ID NO:1, residues 549-557 | LVLAGVGFF | 4.3000 | 37.07 |
| 14 | SEQ ID NO:1, residues 887-895 | FDPRVSIRL | 4.3000 | 37.07 |
| 15 | SEQ ID NO:1, residues 253-261 | WLVPIGQCL | 4.2000 | 36.21 |
| 16 | SEQ ID NO:1, residues 541-549 | VAVGVVLLL | 4.1000 | 35.34 |
| 17 | SEQ ID NO:1, residues 758-766 | FGLSRVLED | 4.1000 | 35.34 |
| 18 | SEQ ID NO:1, residues 215-223 | IAGSDAPSL | 3.9000 | 33.62 |
| 19 | SEQ ID NO:1, residues 86-94 | VYRGEAERI | 3.8000 | 32.76 |
| 20 | SEQ ID NO:1, residues 550-558 | VLAGVGFFI | 3.8000 | 32.76 |

Fig. 12

| ALLELE: DRB1_0801 | Threshold for 3% with score: 1.8 | Highest Score Achievable by any peptide: 8.6 | | |
|---|---|---|---|---|
| Rank | Subsequence Residue Listing | Sequence Reference | Score | % of Highest Score |
| 1 | SEQ ID NO:1, residues 557-565 | FIHRRRKNQ | 5.1000 | 59.30 |
| 2 | SEQ ID NO:1, residues 847-855 | YQLMMQCWQ | 4.6000 | 53.49 |
| 3 | SEQ ID NO:1, residues 779-787 | IPIRWTAPE | 4.4000 | 51.16 |
| 4 | SEQ ID NO:1, residues 64-72 | IYMYSVCNV | 4.3000 | 50.00 |
| 5 | SEQ ID NO:1, residues 545-553 | VVLLLVLAG | 4.0000 | 46.51 |
| 6 | SEQ ID NO:1, residues 685-693 | YKPMMIITE | 4.0000 | 46.51 |
| 7 | SEQ ID NO:1, residues 735-743 | YVHRDLAAR | 3.8000 | 44.19 |
| 8 | SEQ ID NO:1, residues 471-479 | VTYRKKGDS | 3.6000 | 41.86 |
| 9 | SEQ ID NO:1, residues 947-955 | IGVRLPGHQ | 3.6000 | 41.86 |
| 10 | SEQ ID NO:1, residues 791-799 | YRKFTSASD | 3.6000 | 41.86 |
| 11 | SEQ ID NO:1, residues 194-202 | VRVYYKKCP | 3.5000 | 40.70 |
| 12 | SEQ ID NO:1, residues 805-813 | IVMWEVMTY | 3.5000 | 40.70 |
| 13 | SEQ ID NO:1, residues 681-689 | VISKYKPMM | 3.4000 | 39.53 |
| 14 | SEQ ID NO:1, residues 156-164 | FEARHVKLN | 3.4000 | 39.53 |
| 15 | SEQ ID NO:1, residues 344-352 | VELRWTPPQ | 3.3000 | 38.37 |
| 16 | SEQ ID NO:1, residues 716-724 | LVGMLRGIA | 3.2000 | 37.21 |
| 17 | SEQ ID NO:1, residues 96-104 | IELKFTVRD | 3.1000 | 36.05 |
| 18 | SEQ ID NO:1, residues 360-368 | IVYSVTCEQ | 3.0000 | 34.88 |
| 19 | SEQ ID NO:1, residues 85-93 | WVYRGEAER | 2.8000 | 32.56 |
| 20 | SEQ ID NO:1, residues 549-557 | LVLAGVGFF | 2.7000 | 31.40 |

Fig. 13

| ALLELE: DRB1_1101 | Threshold for 3% with score: 1.1 | Highest Score Achievable by any peptide: 8.3 | | |
|---|---|---|---|---|
| Rank | Subsequence Residue Listing | Sequence Reference | Score | % of Highest Score |
| 1 | SEQ ID NO:1, residues 545-553 | VVLLLVLAG | 4.9000 | 59.04 |
| 2 | SEQ ID NO:1, residues 805-813 | IVMWEVMTY | 3.9000 | 46.99 |
| 3 | SEQ ID NO:1, residues 504-512 | LVQVQALTQ | 3.5000 | 42.17 |
| 4 | SEQ ID NO:1, residues 847-855 | YQLMMQCWQ | 3.4000 | 40.96 |
| 5 | SEQ ID NO:1, residues 834-842 | FRLPTPMDC | 3.3000 | 39.76 |
| 6 | SEQ ID NO:1, residues 868-876 | VSILDKLIR | 3.1000 | 37.35 |
| 7 | SEQ ID NO:1, residues 628-636 | YKGMLKTSS | 3.0000 | 36.14 |
| 8 | SEQ ID NO:1, residues 716-724 | LVGMLRGIA | 2.9000 | 34.94 |
| 9 | SEQ ID NO:1, residues 360-368 | IVYSVTCEQ | 2.5000 | 30.12 |
| 10 | SEQ ID NO:1, residues 960-968 | YSLLGLKDQ | 2.3000 | 27.71 |
| 11 | SEQ ID NO:1, residues 524-532 | FQTLSPEGS | 2.2000 | 26.51 |
| 12 | SEQ ID NO:1, residues 685-693 | YKPMMIITE | 2.2000 | 26.51 |
| 13 | SEQ ID NO:1, residues 676-684 | IRLEGVISK | 2.2000 | 26.51 |
| 14 | SEQ ID NO:1, residues 912-920 | WLESIKMQQ | 2.2000 | 26.51 |
| 15 | SEQ ID NO:1, residues 930-938 | YTAIEKVVQ | 2.1000 | 25.30 |
| 16 | SEQ ID NO:1, residues 717-725 | VGMLRGIAA | 2.1000 | 25.30 |
| 17 | SEQ ID NO:1, residues 254-262 | LVPIGQCLC | 2.0000 | 24.10 |
| 18 | SEQ ID NO:1, residues 557-565 | FIHRRRKNQ | 1.9000 | 22.89 |
| 19 | SEQ ID NO:1, residues 549-557 | LVLAGVGFF | 1.9000 | 22.89 |
| 20 | SEQ ID NO:1, residues 29-37 | VVLLDFAAA | 1.8000 | 21.69 |

Fig. 14

| ALLELE: DRB1_1301 | Threshold for 3% with score: 2.6 | Highest Score Achievable by any peptide: 8.8 | | |
|---|---|---|---|---|
| Rank | Subsequence Residue Listing | Sequence Reference | Score | % of Highest Score |
| 1 | SEQ ID NO:1, residues 805-813 | IVMWEVMTY | 5.7000 | 64.77 |
| 2 | SEQ ID NO:1, residues 545-553 | VVLLLVLAG | 5.5000 | 62.50 |
| 3 | SEQ ID NO:1, residues 556-564 | FFIHRRRKN | 4.4000 | 50.00 |
| 4 | SEQ ID NO:1, residues 64-72 | IYMYSVCNV | 4.2000 | 47.73 |
| 5 | SEQ ID NO:1, residues 189-197 | VALLSVRVY | 4.1000 | 46.59 |
| 6 | SEQ ID NO:1, residues 194-202 | VRVYYKKCP | 4.1000 | 46.59 |
| 7 | SEQ ID NO:1, residues 681-689 | VISKYKPMM | 4.0000 | 45.45 |
| 8 | SEQ ID NO:1, residues 868-876 | VSILDKLIR | 3.8000 | 43.18 |
| 9 | SEQ ID NO:1, residues 81-89 | LRTNWVYRG | 3.7000 | 42.05 |
| 10 | SEQ ID NO:1, residues 549-557 | LVLAGVGFF | 3.7000 | 42.05 |
| 11 | SEQ ID NO:1, residues 951-959 | LPGHQKRIA | 3.7000 | 42.05 |
| 12 | SEQ ID NO:1, residues 554-562 | VGFFIHRRR | 3.7000 | 42.05 |
| 13 | SEQ ID NO:1, residues 558-566 | IHRRRKNQR | 3.6000 | 40.91 |
| 14 | SEQ ID NO:1, residues 94-102 | IFIELKFTV | 3.4000 | 38.64 |
| 15 | SEQ ID NO:1, residues 944-952 | IKRIGVRLP | 3.3000 | 37.50 |
| 16 | SEQ ID NO:1, residues 170-178 | VGPLTRKGF | 3.1000 | 35.23 |
| 17 | SEQ ID NO:1, residues 643-651 | VAIKTLKAG | 2.9000 | 32.95 |
| 18 | SEQ ID NO:1, residues 2-10 | MELQAARAC | 2.9000 | 32.95 |
| 19 | SEQ ID NO:1, residues 821-830 | LSNHEVMKA | 2.9000 | 32.95 |
| 20 | SEQ ID NO:1, residues 360-368 | IVYSVTCEQ | 2.9000 | 32.95 |

Fig. 15

| ALLELE: DRB1_1501 | Threshold for 3% with score: 3.25 | Highest Score Achievable by any peptide: 9.8 |
|---|---|---|

| Rank | Subsequence Residue Listing | Sequence Reference | Score | % of Highest Score |
|---|---|---|---|---|
| 1 | SEQ ID NO:1, residues 484-492 | VRRTEGFSV | 4.8000 | 48.98 |
| 2 | SEQ ID NO:1, residues 64-72 | IYMYSVCNV | 4.8000 | 48.98 |
| 3 | SEQ ID NO:1, residues 717-725 | VGMLRGIAA | 4.4000 | 44.90 |
| 4 | SEQ ID NO:1, residues 682-690 | ISKYKPMMI | 4.4000 | 44.90 |
| 5 | SEQ ID NO:1, residues 545-553 | VVLLLVLAG | 4.4000 | 44.90 |
| 6 | SEQ ID NO:1, residues 805-813 | IVMWEVMTY | 4.4000 | 44.90 |
| 7 | SEQ ID NO:1, residues 716-724 | LVGMLRGIA | 4.3000 | 43.88 |
| 8 | SEQ ID NO:1, residues 875-883 | IRAPDSLKT | 4.2000 | 42.86 |
| 9 | SEQ ID NO:1, residues 62-70 | MPIYMYSVC | 4.2000 | 42.86 |
| 10 | SEQ ID NO:1, residues 745-753 | ILVNSNLVC | 3.9000 | 39.80 |
| 11 | SEQ ID NO:1, residues 727-735 | MKYLANMNY | 3.9000 | 39.80 |
| 12 | SEQ ID NO:1, residues 543-551 | VGVVLLLVL | 3.8000 | 38.78 |
| 13 | SEQ ID NO:1, residues 936-944 | VVQMTNDDI | 3.8000 | 38.78 |
| 14 | SEQ ID NO:1, residues 442-450 | VRLEGRSTT | 3.7000 | 37.76 |
| 15 | SEQ ID NO:1, residues 667-675 | MGQFSHHNI | 3.7000 | 37.76 |
| 16 | SEQ ID NO:1, residues 550-558 | VLAGVGFFI | 3.6000 | 36.73 |
| 17 | SEQ ID NO:1, residues 714-722 | LQLVGMLRG | 3.6000 | 36.73 |
| 18 | SEQ ID NO:1, residues 421-429 | LVTSRSFRT | 3.6000 | 36.73 |
| 19 | SEQ ID NO:1, residues 179-187 | YLAFQDIGA | 3.5000 | 35.71 |
| 20 | SEQ ID NO:1, residues 193-202 | VRVYYKKCP | 3.5000 | 35.71 |

Fig. 16

| ALLELE: DRB5_0101 | Threshold for 3% with score: 2.3 | Highest Score Achievable by any peptide: 9.8 | | |
|---|---|---|---|---|
| Rank | Subsequence Residue Listing | Sequence Reference | Score | % of Highest Score |
| 1 | SEQ ID NO:1, residues 720-728 | LRGIAAGMK | 6.0000 | 61.22 |
| 2 | SEQ ID NO:1, residues 808-816 | WEVMTYGER | 4.4000 | 44.90 |
| 3 | SEQ ID NO:1, residues 191-199 | LLSVRVYYK | 3.9000 | 39.80 |
| 4 | SEQ ID NO:1, residues 467-475 | WKYEVTYRK | 3.7000 | 37.76 |
| 5 | SEQ ID NO:1, residues 676-684 | IRLEGVISK | 3.5000 | 35.71 |
| 6 | SEQ ID NO:1, residues 504-512 | LVQVQALTQ | 3.5000 | 35.71 |
| 7 | SEQ ID NO:1, residues 678-686 | LEGVISKYK | 3.5000 | 35.71 |
| 8 | SEQ ID NO:1, residues 713-721 | VLQLVGMLR | 3.2000 | 32.65 |
| 9 | SEQ ID NO:1, residues 484-492 | VRRTEGFSV | 3.2000 | 32.65 |
| 10 | SEQ ID NO:1, residues 847-855 | YQLMMQCWQ | 3.2000 | 32.65 |
| 11 | SEQ ID NO:1, residues 346-354 | LRWTPPQDS | 3.1000 | 31.63 |
| 12 | SEQ ID NO:1, residues 631-639 | MLKTSSGKK | 3.1000 | 31.63 |
| 13 | SEQ ID NO:1, residues 547-555 | LLLVLAGVG | 3.1000 | 31.63 |
| 14 | SEQ ID NO:1, residues 867-875 | IVSILDKLI | 2.7000 | 27.55 |
| 15 | SEQ ID NO:1, residues 949-958 | VRLPGHQKR | 2.7000 | 27.55 |
| 16 | SEQ ID NO:1, residues 10-18 | FALLWGCAL | 2.6000 | 26.53 |
| 17 | SEQ ID NO:1, residues 549-557 | LVLAGVGFF | 2.6000 | 26.53 |
| 18 | SEQ ID NO:1, residues 628-636 | YKGMLKTSS | 2.5000 | 25.51 |
| 19 | SEQ ID NO:1, residues 827-835 | MKAINDGFR | 2.5000 | 25.51 |
| 20 | SEQ ID NO:1, residues 746-754 | LVNSNLVCK | 2.5000 | 25.51 |

Fig. 17

Evaluation of Patient Pre/Post Therapy:

SEQUENCE LISTING

```
<160> NUMBER OF SEQ ID NOS: 4

<210> SEQ ID NO 1
<211> LENGTH: 3935
<212> TYPE: DNA
<213> ORGANISM: Homo sapiens
<220> FEATURE:
<221> NAME/KEY: CDS
<222> LOCATION: (119)..(3049)

<400> SEQUENCE: 1 agggggcagaa gttgcgcgca ggccggcggg cgggagcgga caccgaggcc ggcgtgcagg        60
cgtgcgggtg tgcgggagcc gggctcgggg ggatcggacc gagagcgaga agcgcggc         118 atg gag ctc cag gca gcc cgc gcc tgc ttc gcc ctg ctg tgg ggc tgt         166
Met Glu Leu Gln Ala Ala Arg Ala Cys Phe Ala Leu Leu Trp Gly Cys
1               5                  10                  15
```

```
gcg ctg gcc gcg gcc gcg gcg gcg cag ggc aag gaa gtg gta ctg ctg     214
Ala Leu Ala Ala Ala Ala Ala Ala Gln Gly Lys Glu Val Val Leu Leu
             20                  25                  30 gac ttt gct gca gct gga ggg gag ctc ggc tgg ctc aca cac ccg tat     262
Asp Phe Ala Ala Ala Gly Gly Glu Leu Gly Trp Leu Thr His Pro Tyr
             35                  40                  45 ggc aaa ggg tgg gac ctg atg cag aac atc atg aat gac atg ccg atc     310
Gly Lys Gly Trp Asp Leu Met Gln Asn Ile Met Asn Asp Met Pro Ile
 50                  55                  60 tac atg tac tcc gtg tgc aac gtg atg tct ggc gac cag gac aac tgg     358
Tyr Met Tyr Ser Val Cys Asn Val Met Ser Gly Asp Gln Asp Asn Trp
 65                  70                  75                  80 ctc cgc acc aac tgg gtg tac cga gga gag gct gag cgt atc ttc att     406
Leu Arg Thr Asn Trp Val Tyr Arg Gly Glu Ala Glu Arg Ile Phe Ile
                 85                  90                  95 gag ctc aag ttt act gta cgt gac tgc aac agc ttc cct ggt ggc gcc     454
Glu Leu Lys Phe Thr Val Arg Asp Cys Asn Ser Phe Pro Gly Gly Ala
            100                 105                 110 agc tcc tgc aag gag act ttc aac ctc tac tat gcc gag tcg gac ctg     502
Ser Ser Cys Lys Glu Thr Phe Asn Leu Tyr Tyr Ala Glu Ser Asp Leu
            115                 120                 125 gac tac ggc acc aac ttc cag aag cgc ctg ttc acc aag att gac acc     550
Asp Tyr Gly Thr Asn Phe Gln Lys Arg Leu Phe Thr Lys Ile Asp Thr
        130                 135                 140 att gcg ccc gat gag atc acc gtc agc agc gac ttc gag gca cgc cac     598
Ile Ala Pro Asp Glu Ile Thr Val Ser Ser Asp Phe Glu Ala Arg His
145                 150                 155                 160 gtg aag ctg aac gtg gag gag cgc tcc gtg ggg ccg ctc acc cgc aaa     646
Val Lys Leu Asn Val Glu Glu Arg Ser Val Gly Pro Leu Thr Arg Lys
                165                 170                 175 ggc ttc tac ctg gcc ttc cag gat atc ggt gcc tgt gtg gcg ctg ctc     694
Gly Phe Tyr Leu Ala Phe Gln Asp Ile Gly Ala Cys Val Ala Leu Leu
            180                 185                 190 tcc gtc cgt gtc tac tac aag aag tgc ccc gag ctg ctg cag ggc ctg     742
Ser Val Arg Val Tyr Tyr Lys Lys Cys Pro Glu Leu Leu Gln Gly Leu
            195                 200                 205 gcc cac ttc cct gag acc atc gcc ggc tct gat gca cct tcc ctg gcc     790
Ala His Phe Pro Glu Thr Ile Ala Gly Ser Asp Ala Pro Ser Leu Ala
        210                 215                 220 act gtg gcc ggc acc tgt gtg gac cat gcc gtg gtg cca ccg ggg ggt     838
Thr Val Ala Gly Thr Cys Val Asp His Ala Val Val Pro Pro Gly Gly
225                 230                 235                 240 gaa gag ccc cgt atg cac tgt gca gtg gat ggc gag tgg ctg gtg ccc     886
Glu Glu Pro Arg Met His Cys Ala Val Asp Gly Glu Trp Leu Val Pro
                245                 250                 255 att ggg cag tgc ctg tgc cag gca ggc tac gag aag gtg gag gat gcc     934
Ile Gly Gln Cys Leu Cys Gln Ala Gly Tyr Glu Lys Val Glu Asp Ala
            260                 265                 270 tgc cag gcc tgc tcg cct gga ttt ttt aag ttt gag gca tct gag agc     982
Cys Gln Ala Cys Ser Pro Gly Phe Phe Lys Phe Glu Ala Ser Glu Ser
            275                 280                 285 ccc tgc ttg gag tgc cct gag cac acg ctg cca tcc cct gag ggt gcc    1030
Pro Cys Leu Glu Cys Pro Glu His Thr Leu Pro Ser Pro Glu Gly Ala
        290                 295                 300 acc tcc tgc gag tgt gag gaa ggc ttc ttc cgg gca cct cag gac cca    1078
Thr Ser Cys Glu Cys Glu Glu Gly Phe Phe Arg Ala Pro Gln Asp Pro
305                 310                 315                 320 gcg tcg atg cct tgc aca cga ccc ccc tcc gcc cca cac tac ctc aca    1126
Ala Ser Met Pro Cys Thr Arg Pro Pro Ser Ala Pro His Tyr Leu Thr
                325                 330                 335
```

```
gcc gtg ggc atg ggt gcc aag gtg gag ctg cgc tgg acg ccc cct cag    1174
Ala Val Gly Met Gly Ala Lys Val Glu Leu Arg Trp Thr Pro Pro Gln
            340                 345                 350 gac agc ggg ggc cgc gag gac att gtc tac agc gtc acc tgc gaa cag    1222
Asp Ser Gly Gly Arg Glu Asp Ile Val Tyr Ser Val Thr Cys Glu Gln
        355                 360                 365 tgc tgg ccc gag tct ggg gaa tgc ggg ccg tgt gag gcc agt gtg cgc    1270
Cys Trp Pro Glu Ser Gly Glu Cys Gly Pro Cys Glu Ala Ser Val Arg
    370                 375                 380 tac tcg gag cct cct cac gga ctg acc cgc acc agt gtg aca gtg agc    1318
Tyr Ser Glu Pro Pro His Gly Leu Thr Arg Thr Ser Val Thr Val Ser
385                 390                 395                 400 gac ctg gag ccc cac atg aac tac acc ttc acc gtg gag gcc cgc aat    1366
Asp Leu Glu Pro His Met Asn Tyr Thr Phe Thr Val Glu Ala Arg Asn
                405                 410                 415 ggc gtc tca ggc ctg gta acc agc cgc agc ttc cgt act gcc agt gtc    1414
Gly Val Ser Gly Leu Val Thr Ser Arg Ser Phe Arg Thr Ala Ser Val
            420                 425                 430 agc atc aac cag aca gag ccc ccc aag gtg agg ctg gag ggc cgc agc    1462
Ser Ile Asn Gln Thr Glu Pro Pro Lys Val Arg Leu Glu Gly Arg Ser
        435                 440                 445 acc acc tcg ctt agc gtc tcc tgg agc atc ccc ccg cag cag agc        1510
Thr Thr Ser Leu Ser Val Ser Trp Ser Ile Pro Pro Pro Gln Gln Ser
    450                 455                 460 cga gtg tgg aag tac gag gtc act tac cgc aag aag gga gac tcc aac    1558
Arg Val Trp Lys Tyr Glu Val Thr Tyr Arg Lys Lys Gly Asp Ser Asn
465                 470                 475                 480 agc tac aat gtg cgc cgc acc gag ggt ttc tcc gtg acc ctg gac gac    1606
Ser Tyr Asn Val Arg Arg Thr Glu Gly Phe Ser Val Thr Leu Asp Asp
                485                 490                 495 ctg gcc cca gac acc acc tac ctg gtc cag gtg cag gca ctg acg cag    1654
Leu Ala Pro Asp Thr Thr Tyr Leu Val Gln Val Gln Ala Leu Thr Gln
            500                 505                 510 gag ggc cag ggg gcc ggc agc aag gtg cac gaa ttc cag acg ctg tcc    1702
Glu Gly Gln Gly Ala Gly Ser Lys Val His Glu Phe Gln Thr Leu Ser
        515                 520                 525 ccg gag gga tct ggc aac ttg gcg gtg att ggc ggc gtg gct gtc ggt    1750
Pro Glu Gly Ser Gly Asn Leu Ala Val Ile Gly Gly Val Ala Val Gly
    530                 535                 540 gtg gtc ctg ctt ctg gtg ctg gca gga gtt ggc ttc ttt atc cac cgc    1798
Val Val Leu Leu Leu Val Leu Ala Gly Val Gly Phe Phe Ile His Arg
545                 550                 555                 560 agg agg aag aac cag cgt gcc cgc cag tcc ccg gag gac gtt tac ttc    1846
Arg Arg Lys Asn Gln Arg Ala Arg Gln Ser Pro Glu Asp Val Tyr Phe
                565                 570                 575 tcc aag tca gaa caa ctg aag ccc ctg aag aca tac gtg gac ccc cac    1894
Ser Lys Ser Glu Gln Leu Lys Pro Leu Lys Thr Tyr Val Asp Pro His
            580                 585                 590 aca tat gag gac ccc aac cag gct gtg ttg aag ttc act acc gag atc    1942
Thr Tyr Glu Asp Pro Asn Gln Ala Val Leu Lys Phe Thr Thr Glu Ile
        595                 600                 605 cat cca tcc tgt gtc act cgg cag aag gtg atc gga gca gga gag ttt    1990
His Pro Ser Cys Val Thr Arg Gln Lys Val Ile Gly Ala Gly Glu Phe
    610                 615                 620 ggg gag gtg tac aag ggc atg ctg aag aca tcc tcg ggg aag aag gag    2038
Gly Glu Val Tyr Lys Gly Met Leu Lys Thr Ser Ser Gly Lys Lys Glu
625                 630                 635                 640 gtg ccg gtg gcc atc aag acg ctg aaa gcc ggc tac aca gag aag cag    2086
Val Pro Val Ala Ile Lys Thr Leu Lys Ala Gly Tyr Thr Glu Lys Gln
                645                 650                 655
```

| | | |
|---|---|---|
| cga gtg gac ttc ctc ggc gag gcc ggc atc atg ggc cag ttc agc cac<br>Arg Val Asp Phe Leu Gly Glu Ala Gly Ile Met Gly Gln Phe Ser His<br>660                            665                            670 | | 2134 |
| cac aac atc atc cgc cta gag ggc gtc atc tcc aaa tac aag ccc atg<br>His Asn Ile Ile Arg Leu Glu Gly Val Ile Ser Lys Tyr Lys Pro Met<br>675                            680                            685 | | 2182 |
| atg atc atc act gag tac atg gag aat ggg gcc ctg gac aag ttc ctt<br>Met Ile Ile Thr Glu Tyr Met Glu Asn Gly Ala Leu Asp Lys Phe Leu<br>    690                          695                          700 | | 2230 |
| cgg gag aag gat ggc gag ttc agc gtg ctg cag ctg gtg ggc atg ctg<br>Arg Glu Lys Asp Gly Glu Phe Ser Val Leu Gln Leu Val Gly Met Leu<br>705                            710                            715                          720 | | 2278 |
| cgg ggc atc gca gct ggc atg aag tac ctg gcc aac atg aac tat gtg<br>Arg Gly Ile Ala Ala Gly Met Lys Tyr Leu Ala Asn Met Asn Tyr Val<br>                          725                            730                           735 | | 2326 |
| cac cgt gac ctg gct gcc cgc aac atc ctc gtc aac agc aac ctg gtc<br>His Arg Asp Leu Ala Ala Arg Asn Ile Leu Val Asn Ser Asn Leu Val<br>                 740                            745                           750 | | 2374 |
| tgc aag gtg tct gac ttt ggc ctg tcc cgc gtg ctg gag gac gac ccc<br>Cys Lys Val Ser Asp Phe Gly Leu Ser Arg Val Leu Glu Asp Asp Pro<br>755                            760                            765 | | 2422 |
| gag gcc acc tac acc acc agt ggc ggc aag atc ccc atc cgc tgg acc<br>Glu Ala Thr Tyr Thr Thr Ser Gly Gly Lys Ile Pro Ile Arg Trp Thr<br>770                            775                            780 | | 2470 |
| gcc ccg gag gcc att tcc tac cgg aag ttc acc tct gcc agc gac gtg<br>Ala Pro Glu Ala Ile Ser Tyr Arg Lys Phe Thr Ser Ala Ser Asp Val<br>785                            790                            795                          800 | | 2518 |
| tgg agc ttt ggc att gtc atg tgg gag gtg atg acc tat ggc gag cgg<br>Trp Ser Phe Gly Ile Val Met Trp Glu Val Met Thr Tyr Gly Glu Arg<br>                          805                            810                           815 | | 2566 |
| ccc tac tgg gag ttg tcc aac cac gag gtg atg aaa gcc atc aat gat<br>Pro Tyr Trp Glu Leu Ser Asn His Glu Val Met Lys Ala Ile Asn Asp<br>    820                          825                          830 | | 2614 |
| ggc ttc cgg ctc ccc aca ccc atg gac tgc ccc tcc gcc atc tac cag<br>Gly Phe Arg Leu Pro Thr Pro Met Asp Cys Pro Ser Ala Ile Tyr Gln<br>835                            840                            845 | | 2662 |
| ctc atg atg cag tgc tgg cag cag gag cgt gcc cgc cgc ccc aag ttc<br>Leu Met Met Gln Cys Trp Gln Gln Glu Arg Ala Arg Arg Pro Lys Phe<br>850                            855                            860 | | 2710 |
| gct gac atc gtc agc atc ctg gac aag ctc att cgt gcc cct gac tcc<br>Ala Asp Ile Val Ser Ile Leu Asp Lys Leu Ile Arg Ala Pro Asp Ser<br>865                            870                            875                          880 | | 2758 |
| ctc aag acc ctg gct gac ttt gac ccc cgc gtg tct atc cgg ctc ccc<br>Leu Lys Thr Leu Ala Asp Phe Asp Pro Arg Val Ser Ile Arg Leu Pro<br>                          885                            890                          895 | | 2806 |
| agc acg agc ggc tcg gag ggg gtg ccc ttc cgc acg gtg tcc gag tgg<br>Ser Thr Ser Gly Ser Glu Gly Val Pro Phe Arg Thr Val Ser Glu Trp<br>                 900                            905                           910 | | 2854 |
| ctg gag tcc atc aag atg cag cag tat acg gag cac ttc atg gcg gcc<br>Leu Glu Ser Ile Lys Met Gln Gln Tyr Thr Glu His Phe Met Ala Ala<br>                915                           920                           925 | | 2902 |
| ggc tac act gcc atc gag aag gtg gtg cag atg acc aac gac gac atc<br>Gly Tyr Thr Ala Ile Glu Lys Val Val Gln Met Thr Asn Asp Asp Ile<br>930                            935                            940 | | 2950 |
| aag agg att ggg gtg cgg ctg ccc ggc cac cag aag cgc atc gcc tac<br>Lys Arg Ile Gly Val Arg Leu Pro Gly His Gln Lys Arg Ile Ala Tyr<br>945                            950                            955                          960 | | 2998 |
| agc ctg ctg gga ctc aag gac cag gtg aac act gtg ggg atc ccc atc<br>Ser Leu Leu Gly Leu Lys Asp Gln Val Asn Thr Val Gly Ile Pro Ile<br>                 965                            970                           975 | | 3046 |

```
tga gcctcgacag ggcctggagc cccatcggcc aagaatactt gaagaaacag      3099
agtggcctcc ctgctgtgcc atgctgggcc actggggact ttatttattt ctagttcttt   3159 cctcccctg caacttccgc tgaggggtct cggatgacac cctggcctga actgaggaga   3219
tgaccaggga tgctgggctg ggccctcttt ccctgcgaga cgcacacagc tgagcactta   3279
gcaggcaccg ccacgtccca gcatccctgg agcaggagcc ccgccacagc cttcggacag   3339
acatatagga tattcccaag ccgaccttcc ctccgccttc tcccacatga ggccatctca   3399
ggagatggag ggcttggccc agcgccaagt aaacagggta cctcaagccc catttcctca   3459
cactaagagg gcagactgtg aacttgactg ggtgagaccc aaagcggtcc ctgtccctct   3519
agtgccttct ttagaccctc gggccccatc ctcatccctg actggccaaa cccttgcttt   3579
cctgggcctt tgcaagatgc ttggttgtgt tgaggttttt aaatatatat tttgtacttt   3639
gtggagaaaa tgtgtgtgtg tggcaggggg ccccgccagg gctggggaca gagggtgtca   3699
aacattcgtg agctggggac tcagggaccg gtgctgcagg agtgtcctgc ccatgcccca   3759
gtcggcccca tctctcatcc ttttggataa gtttctattc tgtcagtgtt aaagattttg   3819
ttttgttgga cattttttc gaatcttaat ttattatttt ttttatattt attgttagaa   3879
aatgacttat ttctgctctg gaataaagtt gcagatgatt caaaaaaaaa aaaaaa      3935
```

<210> SEQ ID NO 2
<211> LENGTH: 976
<212> TYPE: PRT
<213> ORGANISM: Homo sapiens

<400> SEQUENCE: 2

```
Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220
```

-continued

```
Thr Val Ala Gly Thr Cys Val Asp His Ala Val Pro Pro Gly Gly
225                 230                 235                 240

Glu Glu Pro Arg Met His Cys Ala Val Asp Gly Glu Trp Leu Val Pro
            245                 250                 255

Ile Gly Gln Cys Leu Cys Gln Ala Gly Tyr Glu Lys Val Glu Asp Ala
        260                 265                 270

Cys Gln Ala Cys Ser Pro Gly Phe Phe Lys Phe Glu Ala Ser Glu Ser
    275                 280                 285

Pro Cys Leu Glu Cys Pro Glu His Thr Leu Pro Ser Pro Glu Gly Ala
290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
            325                 330                 335

Ala Val Gly Met Gly Ala Lys Val Glu Leu Arg Trp Thr Pro Pro Gln
        340                 345                 350

Asp Ser Gly Gly Arg Glu Asp Ile Val Tyr Ser Val Thr Cys Glu Gln
    355                 360                 365

Cys Trp Pro Glu Ser Gly Glu Cys Gly Pro Cys Glu Ala Ser Val Arg
370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
            405                 410                 415

Gly Val Ser Gly Leu Val Thr Ser Arg Ser Phe Arg Thr Ala Ser Val
        420                 425                 430

Ser Ile Asn Gln Thr Glu Pro Pro Lys Val Arg Leu Glu Gly Arg Ser
    435                 440                 445

Thr Thr Ser Leu Ser Val Ser Trp Ser Ile Pro Pro Pro Gln Gln Ser
450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
            485                 490                 495

Leu Ala Pro Asp Thr Thr Tyr Leu Val Gln Val Gln Ala Leu Thr Gln
        500                 505                 510

Glu Gly Gln Gly Ala Gly Ser Lys Val His Glu Phe Gln Thr Leu Ser
    515                 520                 525

Pro Glu Gly Ser Gly Asn Leu Ala Val Ile Gly Gly Val Ala Val Gly
530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
            565                 570                 575

Ser Lys Ser Glu Gln Leu Lys Pro Leu Lys Thr Tyr Val Asp Pro His
        580                 585                 590

Thr Tyr Glu Asp Pro Asn Gln Ala Val Leu Lys Phe Thr Thr Glu Ile
    595                 600                 605

His Pro Ser Cys Val Thr Arg Gln Lys Val Ile Gly Ala Gly Glu Phe
610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
```

```
                    645                 650                 655
Arg Val Asp Phe Leu Gly Glu Ala Gly Ile Met Gly Gln Phe Ser His
                660                 665                 670

His Asn Ile Ile Arg Leu Glu Gly Val Ile Ser Lys Tyr Lys Pro Met
            675                 680                 685

Met Ile Ile Thr Glu Tyr Met Glu Asn Gly Ala Leu Asp Lys Phe Leu
        690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
        915                 920                 925

Gly Tyr Thr Ala Ile Glu Lys Val Val Gln Met Thr Asn Asp Asp Ile
    930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 3
<211> LENGTH: 9
<212> TYPE: PRT
<213> ORGANISM: Human immunodeficiency virus type 1

<400> SEQUENCE: 3

Ala Phe His His Val Ala Arg Glu Leu
1               5

<210> SEQ ID NO 4
<211> LENGTH: 20
<212> TYPE: PRT
<213> ORGANISM: Plasmodium falciparum

<400> SEQUENCE: 4
```

```
Glu Tyr Leu Asn Lys Ile Gln Asn Ser Leu Ser Thr Glu Trp Ser Pro
1               5                   10                  15

Cys Ser Val Thr
            20
```

EPHA2 T CELL EPITOPES AND USES THEREFOR

CROSS REFERENCE TO RELATED APPLICATIONS

This application is a divisional of United States application Ser. No. 11/977,179, filed Oct. 22, 2007, now U.S. Pat. No. 8,114,407, which is a continuation of U.S. application Ser. No. 11/233,796, filed Sep. 23, 2005, now U.S. Pat. No. 7,297,337, which is a continuation of U.S. application Ser. No. 10/897,711, filed on Jul. 22, 2004 now abandoned and published on Mar. 3, 2005 as U.S. Patent Application Publication No. 2005/0048550 A1, which claims priority to U.S. Provisional Patent Application No. 60/491,046, filed Jul. 30, 2003, to each of which priority is claimed and all of which are incorporated herein by reference in their entireties.

This work was supported by National Institutes of Health (NIH) grant Nos. CA57840 and CA56937.

BACKGROUND

1. Field of the Invention

Eph2A T-cell epitopes are provided. The Eph2A T-cell epitopes are useful in methods for diagnosing cancer, for quantifying EphA2-reactive T-cells in a patient and in eliciting an immune response to EphA2 and modulating the immune system to recognize cancerous cells.

2. Description of the Related Art

The molecular identification of tumor antigens recognized by the immune system has paved the way for the development of new immunotherapeutic strategies for the treatment of cancer. While many cytotoxic T lymphocyte (CTL)-defined tumor-associated epitopes have been applied clinically in cancer vaccinations (Coolie P G, et al. Proc Natl Acad Sci USA 98: 10290-1295, 2001; Yu J S, et al. Cancer Res 61: 842-847, 2001; Jager E, et al. Proc Natl Acad Sci USA 97: 12198-12203, 2000; and Nestle F O, et al. Nat Med 4:328-332, 1998.), comparatively few class II-restricted epitopes recognized by $CD4^+$ T cells have been identified and clinically-integrated to date (Topalian S L, et al. Proc Natl Acad Sci USA 91; 9461-9465, 1994; Chaux P, et al. J Exp Med 189; 767-777, 1999; Pieper R, et al. J Exp Med 189; 757-765, 1999; Wang R F, et al. Science 284; 1351-1354, 1999; Topalian S L, et al. J Exp Med 183; 1965-1971, 1996; Jager E, et al. J Exp Med 191; 625-630, 2000; Zarour H M, et al. Cancer Res 60; 4946-4952, 2000; and Zarour H M, et al. Proc Natl Acad Sci USA 97; 400-405, 2000). Current paradigms suggest that $CD4^+$ T cells (at least Th1-type) play critical roles in the optimal induction and maintenance of clinically beneficial tumor immunity (Pardon D M, et al. Curr Opin Immunol 10; 588-594, 1998 and Toes R E, et al. J Exp Med 189; 753-756, 1999). Hence, $CD4^+$ and $CD8^+$ T cell epitopes derived from antigens that are unique to, or that are overexpressed on tumor cells may provide effective vaccine components.

The Eph family of molecules constitutes the largest family of receptor tyrosine kinases in the human genome. Eph kinases include two major classes (EphA and EphB), which are distinguished by their specificities for the ligands ephrin-A and ephrin-B, respectively (Eph Nomenclature Committee. Unified nomenclature for Eph family receptors and their ligands. The ephrins, Cell 90; 403-404, 1997). Largely known for their role in neuronal development, recent reports suggest that Eph receptors play a role in carcinogenesis. For example, EphA2 is overexpressed and functionally altered in a large number of different cancers, where it appears to promote the development of disseminated disease. In normal cells, EphA2 localizes to sites of cell-to-cell contact, where it may play a role as a negative regulator of cell growth. In contrast, EphA2 is frequently overexpressed and often functionally dysregulated in advanced cancers, where it contributes to many different aspects of malignant character. These changes in EphA2 have been observed in a wide array of solid tumors, including melanoma, prostate, breast and lung tumors. The highest degree of EphA2 expression among tumors is most commonly observed in metastatic lesions.

In the clinical setting, several findings suggest that T cell-mediated immunity provides a safeguard against the development and progression of renal cell carcinoma (RCC) and may effectively mediate the regression of established lesions. RCC lesions are typically infiltrated with large numbers of lymphocytes, though the benefits of leukocytic infiltration upon beneficial clinical outcome remain unknown. While this may reflect variance in the functional subsets of $CD4^+$ and $CD8^+$ T cells in these infiltrates, data addressing the prognostic benefit of Th1/Tc1-biased immunity versus Th2/Tc2-biased immunity in RCC patients has been equivocal. A better understanding of the constitutive nature and specificity of $CD8^+$ and $CD4^+$ T cell responses in RCC patients will likely provide insights necessary to design, implement and monitor more effective treatment options.

SUMMARY

Provided herein are novel EphA2 T-cell epitopes and uses therefor, including diagnostic and prognostic methods, methods for eliciting an immune response to EphA2 and treatments for cancer. The epitopes are useful in the detection and staging of RCC. It is demonstrated herein that high levels of EphA2 expression are observed in the setting of renal cell carcinoma (method of staging RCC) and that patients with RCC exhibit both $CD8^+$ and $CD4^+$ T cell responses to novel EphA2-derived epitopes. Moreover, the reactivity of T cells against EphA2 is useful in distinguishing disease status and outcome and the EphA2 T-cell epitopes described herein are useful in eliciting an immune response to EphA2, as a cancer therapy.

In one embodiment, an EphA2 epitope is provided comprising an EphA2 T-cell epitope. The EphA2 T-cell epitope may be a peptide comprising an EphA2 T-cell epitope. In certain embodiments, the peptide consists of from about 9 to about 35 amino acids, from about 9 to about 25 amino acids or less than about 20 amino acids. The peptide can be a portion or fragment of native human EphA2 (SEQ ID NO: 2) and typically comprises at least about 9 contiguous amino acids of SEQ ID NO: 2 or a conservative derivative of a portion of SEQ ID NO: 2 in which one or more amino acid residues are inserted into the peptide or one or more amino acids of SEQ ID NO: 2 are deleted from the peptide or substituted with one or more different amino acid residues, so long as the binding of the conservative derivative to an MHC molecule is substantially equal to or enhanced as compared to binding of EphA2 or a fragment thereof to the MHC molecule.

The EphA2 T-cell epitope can be a modified peptide comprising one or more of N-terminal modifications, C-terminal modifications, internal modifications or non-standard residues, for example and without limitation, a solubilizing group; a hydrophobic group; a lipid group; a hydrophilic group; a tag; a fluorescent tag; a polypeptide tag; a transmembrane signal sequence or a portion thereof; an amino acid enantiomer and one of an acetyl, benzyloxycarbonyl, biotin, cinnamoyl, dabcyl, dabsyl, dansyl, dinitrophenyl, cyanine, fluorescein, fmoc, formyl, lissamine rhodamine, myristoyl, n-methyl, palmitoyl, steroyl, 7-methoxycoumarin acetic acid, biotin, dabcyl, dabsyl, dansyl, disulphide, acetamidomethyl, aminohexanoic acid, aminoisobutyric acid, beta alanine, cyclohexylalanine, d-cyclohexylalanine, e-acetyl lysine, gamma aminobutyric acid, hydroxyproline, nitro-arginine, nitro-phenylalanine, nitro-tyrosine, norleucine, norvaline, octahydroindole carboxylate, ornithine, penicillamine, phenylglycine, phosphoserine, phosphothreonine, phosphotyrosine, L-malonyltyrosine, pyroglutamate, tetrahydroisoquinoline, amide, N-substituted glycine; non-amino acyl and N-acetylglycine group. In certain embodiments, the EphA2 T-cell epitope is a peptoid or a peptidomimetic comprising an EphA2 T-cell epitope.

In certain embodiments, the EphA2 T-cell epitope comprises a T-cell epitope contained in one or more of the following EphA2 epitope sequences: TLADFDPRV (SEQ ID NO: 2, residues 883-891); VLLLVLAGV (SEQ ID NO.: 2, residues 546-554); VLAGVGFFI (SEQ ID NO: 2, residues 550-558); IMNDMPIYM (SEQ ID NO: 2, residues 58-66); SLLGLKDQV (SEQ ID NO: 2, residues 961-969); WLVPIGQCL (SEQ ID NO: 2, residues 253-261); LLWGCALAA (SEQ ID NO: 2, residues 12-20); GLTRTSVTV (SEQ ID NO: 2, residues 391-399); NLYYAESDL (SEQ ID NO: 2, residues 120-128); KLNVEERSV (SEQ ID NO: 2, residues 162-170); IMGQFSHHN (SEQ ID NO: 2, residues 666-674); YSVCNVMSG (SEQ ID NO: 2, residues 67-75); MQNIMNDMP (SEQ ID NO: 2, residues 55-63) and a sequence presented in one or more of FIGS. 5-17.

As a non-limiting example, the EphA2 T-cell epitope can comprise a peptide, or a modified version thereof, comprising one or more of the following amino acid sequences: TLADFDPRV (SEQ ID NO: 2, residues 883-891); VLLLVLAGV (SEQ ID NO: 2, residues 546-554); VLAGVGFFI (SEQ ID NO: 2, residues 550-558); IMNDMPIYM (SEQ ID NO: 2, residues 58-66); SLLGLKDQV (SEQ ID NO: 2, residues 961-969); WLVPIGQCL (SEQ ID NO: 2, residues 253-261); LLWGCALAA (SEQ ID NO: 2, residues 12-20); GLTRTSVTV (SEQ ID NO: 2, residues 391-399); NLYYAESDL (SEQ ID NO: 2, residues 120-128); KLNVEERSV (SEQ ID NO: 2, residues 162-170); IMGQFSHHN (SEQ ID NO: 2, residues 666-674); YSVCNVMSG (SEQ ID NO: 2, residues 67-75); MQNIMNDMP (SEQ ID NO: 2, residues 55-63) and a sequence presented in one or more of FIGS. 5-17, or a conservative derivative thereof. In one embodiment, the EphA2 T-cell epitope comprises two or more EphA2 T-cell epitopes separated by a spacer.

A composition is provided that comprises one or more EphA2 T-cell epitope as described above and a pharmaceutically acceptable carrier.

In another embodiment, a method of monitoring the number and/or status of EphA2-reactive T-cells in a patient is provided, the method comprises determining the patient's immune reactivity to a compound or composition containing an EphA2 T-cell epitope containing one or more EphA2 T-cell epitopes, as described above. In one embodiment, the method comprises determining the patient's immune reactivity to a compound or composition containing one or more EphA2 T-cell epitopes using an ELISPOT assay. The ELISPOT assay may detect a CD8$^+$ response to an MHC class I protein-presented EphA2 epitope or a conservative derivative thereof. The MHC class I protein can be an HLA-A2 protein. The ELISPOT assay also may detect a CD4$^+$ response to an MHC class II protein-presented EphA2 epitope or a conservative derivative thereof. The MHC class II protein can be an HLA-DR4 protein.

In a further embodiment, a method is provided for inhibiting growth in a patient of a cancer in which EphA2 is over-expressed, comprising administering to the patient an amount of an EphA2 T-cell epitope as described above, effective to elicit an immune response to EphA2 in the patient. In one embodiment, the method comprises contacting an antigen-presenting cell of a patient with the EphA2 T-cell epitope. In another embodiment, the method is an ex vivo method comprising: isolating cells comprising an antigen-presenting cell from the patient; contacting the antigen-presenting cell with the EphA2 T-cell epitope; and reintroducing the EphA2 T-cell epitope-contacted antigen-presenting cell into the patient. The method may further comprise administering to the patient an EphA2 Ligand or agonist thereof, such as, without limitation, a binding reagent capable of binding to EphA2; and ephrinA1 or an agonist thereof.

Also provided is an isolated nucleic acid comprising from 5' to 3' and operably linked, a promoter, a coding sequence, other than a full length EphA2 coding sequence, encoding a peptide comprising one or more EphA2 T-cell epitopes and a polyadenylation signal. The nucleic acid is useful in preparing the EphA2 T-cell epitope by recombinant methods and/or by transfer of the nucleic acid into a patient's cells, either ex vivo or in vivo, to produce the EphA2 T-cell epitope in vivo.

In another embodiment, a method is provided comprising contacting a tumor cell that expresses EphA2 on its surface with an EphA2 ligand or agonist thereof comprising one of: a binding reagent capable of binding to EphA2; and ephrinA1 or an agonist thereof.

BRIEF DESCRIPTION OF THE DRAWINGS

FIGS. 1 and 2A-B provide the amino acid (SEQ ID NO: 2) and nucleic acid (SEQ ID NO: 1) sequences of human EphA2 (GenBank Accession Nos. AAH37166 and BC037166 (also NM_004431), respectively).

FIGS. 3A-B and 4A-C provide non limiting lists of human MHC Class II and Class I alleles, respectively.

FIGS. 5-8 provide in silica predicted MHC Class I binding peptides within the EphA2 amino acid sequence for the Class I alleles HLA-A1, HLA-A3, HLA-B7 and HLA-B44, respectively (portions of SEQ ID NO: 2, as indicated). In FIGS. 5-8, the "Score" refers to an estimate of the half time of dissociation ($T_{1/2}$) of a molecule containing the listed sequence.

FIGS. 9-17 provide in silica predicted MHC Class II binding peptides within the EphA2 amino acid sequence for the Class II alleles HLA-DRβ1*0101, HLA-DRβ1*0301, HLA-DRβ1*0701, HLA-DRβ1*0801, HLA-DRβ1*1101, HLA-DRβ1*1301, HLA-DRβ1*1501 and HLA-DRβ5*0101, respectively (portions of SEQ ID NO: 2, as indicated). In FIGS. 9-17, the "Score" refers to a comparison of binding to a theoretical positive control generated by the software used to identify the peptides.

SEQUENCE LISTING

Figure 18:
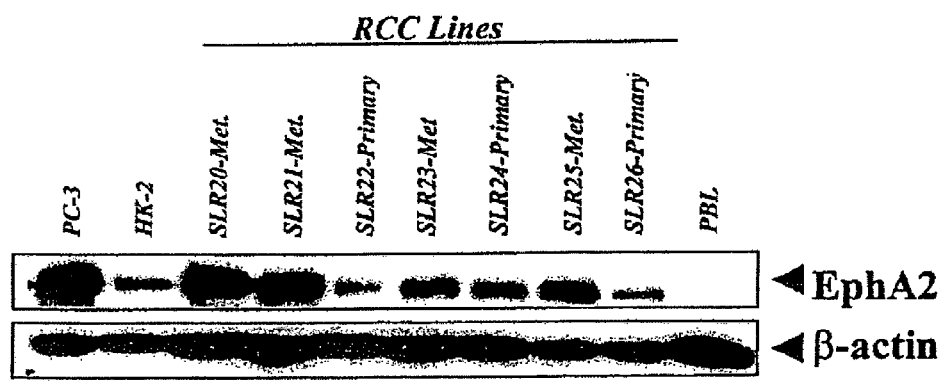
FIG. 18 is a Western blot showing analysis of lysates generated from the indicated RCC cell lines.

The specification further incorporates by reference the Sequence Listing submitted herewith via EFS on Apr. 17, 2012. Pursuant to 37 C.F.R. §1.52(e)(5), the Sequence Listing text file, identified as 0723960474seqlist.txt, is 24,695 bytes and was created on April 11, 2012. The Sequence Listing, electronically filed herewith, does not extend beyond the scope of the specification and thus does not contain new matter.

DETAILED DESCRIPTION

Provided herein are EphA2 T-cell epitopes. The epitopes are compounds containing one or more T-cell epitopes of EphA2 and typically are peptides corresponding to portions of the EphA2 amino acid sequence (FIG. 1, SEQ ID NO: 2). Also provided are methods for making the epitopes and recombinant systems for production of the epitopes. The EphA2 T-cell epitopes are useful in methods for determining a patient's immune status, or immune reactivity to EphA2 by quantifying the number of EphA2-reactive T-cells in the patient. The epitopes also are useful in modulating a patient's immune responsiveness to EphA2 as a cancer treatment.

As used herein, the term "agonist" is a ligand that is capable of combining with (binding) a receptor on a cell and initiating a reaction or activity that mimics the activity of a natural ligand, which, in the context of the present disclosure is native EphA2 as shown in FIG. 1. The term "epitope" refers to a physical structure that contains and/or defines an antigenic determinant. "Peptide agonists" are peptides, peptide derivatives or peptide analogs that mimic a naturally-occurring ligand, which, in the context of the present disclosure, is an EphA2 ligand.

The term "binding reagent" and like terms, refers to any compound, composition or molecule capable of specifically or substantially specifically (that is with limited cross-reactivity) binding another compound or molecule, which, in the case of immune-recognition contains an epitope. Typically, the binding reagents are antibodies, preferably monoclonal antibodies, or derivatives or analogs thereof, including without limitation: Fv fragments; single chain Fv (scFv) fragments; Fab' fragments; F(ab')2 fragments; humanized antibodies and antibody fragments; camelized antibodies and antibody fragments; and multivalent versions of the foregoing. Multivalent binding reagents also may be used, as appropriate, including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments. "Binding reagents" also include aptamers, as are described in the art.

Methods of making antigen-specific binding reagents, including antibodies and their derivatives and analogs and aptamers, are well-known in the art. Polyclonal antibodies can be generated by immunization of an animal. Monoclonal antibodies can be prepared according to standard (hybridoma) methodology. Antibody derivatives and analogs, including humanized antibodies can be prepared recombinantly by isolating a DNA fragment from DNA encoding a monoclonal antibody and subcloning the appropriate V regions into an appropriate expression vector according to standard methods. Phage display and aptamer technology is described in the literature and permit in vitro clonal amplification of antigen-specific binding reagents with very affinity low cross-reactivity. Phage display reagents and systems are available commercially, and include the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Aptamer technology is described for example and without limitation in U.S. Pat. Nos. 5,270,163, 5,475096, 5,840,867 and 6,544,776.

A "gene" is an operative genetic determinant in its broadest sense. A gene includes an "expressed sequence" that encodes a protein or is transcribed into a functional RNA product, for example an open reading frame (ORF). A typical gene includes an expressed sequence, along with operably linked regulatory sequences, including, but not limited to, promoters, enhancers, transcription factor binding sequences, operators and terminators (for example poly(A) sequences). Promoters can be, for example and without limitation, constitutive or semi-constitutive (for example, CMV and RSV promoters), tissue-specific promoters (for example, a muscle creatinine kinase (MCK) promoter) or induceable (for example and without limitation tetracycline-regulatable systems, such as the BD Tet-On™ and BD Tet-Off™. Gene Expression Systems, commercially available form BD Biosciences Clontech of Palo Alto, Calif.). Two sequences are considered to be "operably linked" if they are arranged in cis to act in an expected manner in relationship to each other. In a gene, regulatory sequences are operably linked in a manner sufficient to cause correct and/or desired transcription of the expressed sequence in a cell. The terms "expression" or "gene expression," and like words and phrases, mean the overall process by which the information encoded in a nucleic acid, typically a gene, is converted into a ribonucleic acid and/or a protein, or a post-translationally modified version thereof, and/or an observable phenotype.

As used herein, a "nucleic acid" may be, without limitation, any polynucleotide or polydeoxynucleotide. Without limitation, a nucleic acid may be single-stranded or double stranded. In context of the human EphA2 peptide and nucleotide sequences disclosed herein (FIG. 1, SEQ ID NO: 2 and FIG. 2, SEQ ID NO: 1, respectively), reference is made to conservative derivatives. A "conservative derivative" is a nucleic acid or a peptide containing conservative substitutions, which include, in the case of a nucleic acid, substitutions with nucleotide bases that account for codon degeneracy, for example and without limitation in reference to the Ala codon, the substitution of GCC or GCG for GCA, or, in the case of both nucleic acids and peptides, that represent conservative amino acid substitutions, including but not limited to the conservative substitution groups: Ser and Thr; Leu, Ile and Val; Glu and Asp; and Gln and Asn. Conservative substitutions also may be determined by other methods, such as, without limitation, those used by the BLAST (Basic Local Alignment Search Tool) algorithm, such as a BLOSUM Substitution Scoring Matrix, such as the BLOSUM 62 matrix. Importantly, a conservative derivative substantially retains the function of the native nucleic acid or peptide to which the conservative derivative corresponds. In the context of an EphA2 T-cell epitope, a conservative derivative, as with all "derivatives," substantially retains the ability to stimulate an appropriate immune response to EphA2 in the assays described herein.

The similarity between two nucleic acid or protein sequences may be determined by a variety of methods. For example, the similarities may be determined in silico by an algorithm, for example a BLAST algorithm, which is the reference standard used herein. The similarity between two nucleic acid sequences also may be determined by specific hybridization, which means that a nucleic acid will hybridize specifically in a genome to a reference nucleic acid (namely, the EphA2 sequence provided herein or portions thereof). The hybridization conditions for achieving specificity naturally will differ, depending on such factors including, without limitation, the length of sequence overlap of the respective nucleic acids, its (melting temperature) Tm, the specific genome and the assay conditions.

"Derivatives" also include chemically modified nucleic acids or peptides corresponding to portions of the EphA nucleotide or amino acid sequence and conservative derivatives thereof. The nucleic acids or peptides, or conservative derivatives thereof may be derivatized to contain chemical groups that, for example: modify the solubility of the nucleic acid or peptide, for example by the addition of a PEG group; permit affinity purification of the peptide or nucleic acid, for example by the addition of a biotin or poly(his) tag;) or permit detection of the compound, for example by conjugation with a fluorochrome, such as fluorescein isothiocyanate, Cy3 or Cy5 or a radionuclide-containing or caging group for in vitro or in vivo detection and location of the nucleic acid, peptide or derivative thereof. These examples of modified nucleic acids and peptides, and used therefor, are only limited examples of the large variety of useful modifications of nucleic acids and peptides that are known in the art. A more complete, but non exhaustive list of such modifications include one or more of N-terminal modifications, C-terminal modifications, internal modifications or non-standard residues for example, and without limitation the following groups and/or residues: a solubilizing group (such as, without limitation a polyethylene glycol (PEG) group), a hydrophobic group, a lipid group, a hydrophilic group, a tag (such as, without limitation: a fluorescent tag (such as fluorescein (e.g., FITC) or a cyanine dye (e.g., Cy3 or Cy5)) or a polypeptide tag (e.g., poly-histidine, for affinity purification, for example)), a transmembrane signal sequence or a portion thereof, an amino acid enantiomer, acetyl, benzyloxycarbonyl, biotin, cinnamoyl, dabcyl, dabsyl, dansyl, dinitrophenyl, cyanine, fluorescein, fmoc, formyl, lissamine, rhodamine, myristoyl, n-methyl, palmitoyl, steroyl, 7-methoxycoumarin acetic acid, biotin, dabcyl, dabsyl, dansyl, disulphide, acetamidomethyl, aminohexanoic acid, aminoisobutyric acid, beta alanine, cyclohexylalanine, d-cyclohexylalanine, e-acetyl lysine, gamma aminobutyric acid, hydroxyproline, nitro-arginine, nitro-phenyl alanine, nitro-tyrosine, norleucine, norvaline, octahydroindole carboxylate, ornithine, penicillamine, phenylglycine, phosphoserine, phosphothreonine, phosphotyrosine, L-malonyltyrosine, pyroglutamate, tetrahydroisoquinoline, amide, N-substituted glycines and/or non-amino acyl groups (peptoids), N-acetylglycine.

"Derivatives" also include peptide analogs, which are peptides containing one or more modified bases and/or a modified peptide backbone (a typical or normal peptide backbone having the structure: ... —NH—CR—CO—NH—CR—CO—NH—CR—CO— ... ). Peptide analogs include "peptidomimetics", which are compounds containing one or more non-peptidic structural elements that are capable of mimicking or antagonizing the biological action(s) of a natural parent peptide. A peptidomimetic does not have classical peptide characteristics such as enzymatically scissile peptide bonds. A common peptidomimetic is a "peptoid", which is a polymer that that includes one or more N-substituted amino acid residues, such as N-substituted glycine. Non-limiting examples of peptoids, peptoid synthesis methods, uses for peptoids and methods of using peptoids are provided in Simon, R. et al. (1992), Proc. Natl. Acad. Sci. USA, 89:9367-9371; Murphy, J. E. et al., (1998) Proc. Natl. Acad. Sci. USA, 95:1517-1522 and in U.S. Pat. Nos. 5,811,387, 5,877,278, 5,965,695 and 6,075,121, which are incorporated herein by reference for their teachings of peptoid structures, peptoid synthesis methods, uses for peptoids and methods of using peptoids.

In the examples, certain T-cell epitopes of EphA2 are described and analyzed for their ability to elicit an EphA2-specific immune response. Those epitopes were identified in silico in the context of the MHC Class II allele HLA-DRβ1*0401 (DR4) or the Class I allele HLA-A0201 (HLA-A2). HLA-DRβ1*0401 and HLA-A0201 are two alleles among many Non-limiting examples of other Class II HLA-DR alleles are shown in FIG. 3, including HLA-DR1, HLA-DR3, HLA-DR4, HLA-DR7, HLA-DR8, HLA-DR9, HLA-DR11, HLA-DR12, HLA-DR13, HLA-DR14 and HLA-DR15 alleles. More common Class II alleles include, without limitation: HLA-DR2, HLA-DR3, HLA-DR4 and HLA-DR5. Southwood et al., 1998, Honeyman et al., 1998 and De Groot et al., Vaccine (2001) 19:4385-4395 describe algorithms, consensus sequences and other methods for identifying MHC-binding sequences in connection with a variety of HLA-DR.BETA.1 alleles. By applying the algorithms described in those references, or other algorithms that search for consensus MHC-II binding sequences (such as the Pro-Pred software/algorithms referenced herein), other EphA2 MHC-II-containing fragments can be identified that are specific to alleles other than HLA-DRβ1*0401 or HLA-A0201. Once the consensus MHC II binding sequences are identified, the algorithm described below for use in identifying proteasomal cleavage products, or any like algorithms, can be used to select candidate testing for screening in ELISPOT assays and ELISA assays as described herein, or like assays, for immunostimulatory activity in EphA2-reactive PBLs from a patient with the same MHC haplotype.

As with the Class II alleles described above, a large number of MHC class I alleles other than HLA-A0201 also have been identified and EphA2 T-cell epitopes specific to those alleles can be determined in a like manner. Non-limiting examples of MHC class I HLA-A or HLA-B alleles are provided in FIG. 4. More common alleles include, without limitation: HLA-A1, HLA-A2, HLA-A3, HLA-B7 and HLA-B44.

As indicated above, the consensus binding sequences have been resolved for many of the MHC Class I and II alleles provided in FIGS. 3 and 4. FIGS. 5-8 provide in silica predicted MHC Class I binding peptides within the EphA2 amino acid sequence for the Class I alleles HLA-A1, HLA-A3, HLA-B7 and HLA-B44, respectively. FIGS. 9-17 provide in silica predicted MHC Class II binding peptides within the EphA2 amino acid sequence for the Class II alleles HLA-DRβ1*0101, HLA-DRβ1*0301, HLA-DRβ1*0401, HLA-DRβ1*0701, HLA-DRβ1*0801, HLA-DRβ1*1101, HLA-DRβ1*1301, HLA-DRβ1*1501 and HLA-DRβ5*0101, respectively.

Although the available software useful in identifying MHC-consensus binding regions contains consensus sequences for many MHC Class I and Class II alleles (including, without limitation, 39 Class I alleles, including HLA-A1, HLA-A24 and HLA-B7 alleles, available for searching in the NIH BIMAS "HLA Peptide Binding Predictions" software (for example, at http://bimas.dcrt.nih.gov/molbio/hla_bind/) and 51 Class II alleles, including 49 HLA-DRβ1 alleles and 2 HLA-DR155 alleles, Singh et al., ProPred: prediction of HLA-DR binding sites Bioinformatics (2001) December; 17(12):1236-7; both of which were utilized to identify the putative EphA2 Class I and Class II T-cell epitopes identified in one or more of FIGS. 5-17), methods for identifying consensus binding sequences are well-described in the literature. For example, Luckey et al., 2001 describes methods for identifying Class I binding sequences—briefly by the steps of acid-treating cells to elute Class I molecules, affinity purifying the various alleles, eluting bound peptides form the affinity-purified HLA molecules and sequencing the eluted peptides. Methods for identifying consensus binding sequences for each allele, and the recognition that many alleles can bind the same or very similar peptide sequence repertoirs (HLA supertypes) is discussed in Southwood et al., 1998. Nevertheless, the overall goal is to identify specific EphA2 T-cell epitopes, which can be accomplished by eluting processed EphA2 peptide fragments from any MHC molecule purified from a cell, such as an APC (antigen presenting cell), for any MHC allele, and sequencing the eluted peptides, all according to well-established methods. This completely avoids the in silico step.

The EphA2 T-cell epitopes described herein, can be used in ELISPOT, or like assays, to screen patients for their immune reactivity to EphA2, and can be used to stimulate a patient's immune response to EphA2. In this manner an immunogenic composition or cocktail can be prepared for a given patient, depending on that patient's HLA-DR haplotype. As also mentioned herein, an immune response to sub-dominant EphA2 T-cell epitopes can be elicited in a patient, which could overwhelm the patient's tolerance to one or more dominant epitopes.

The EphA2 T-cell epitope compounds are useful in an assay to establish a patient's existing immunity to EphA2. As described herein, a population of a patient's PBLs may be stimulated with a compound containing one or more EphA2 T-cell epitopes, as described herein. The one or more EphA2 T-cell epitopes are selected to match the patient's MHC haplotype. Hence, if the patient has the HLA-DRβ1*0701 allele, a compound containing one or more EphA2 HLA-DRβ1*0701-binding peptides is selected. Once stimulated with the compound for a sufficient period of time (typically 6 hours to 48 hours), the PBL population is tested for stimulation by the antigen. This testing can be performed by a variety of methods, such as by ELISPOT to determine IFN-γ or IL-5 production, or ELISA to determine TGF-β or IL-10 production, purportedly indicative of antigen-specific suppression.

A number of assays are used to detect antigen-specific immune responses (see, Keilholz, U. et al., "Immunologic Monitoring of Cancer Vaccine Therapy: Results of a Workshop Sponsored by the Society for Biological Therapy," J. Immunother., (2002) 25(2):97-138). The ELISPOT assay described herein is quite sensitive and accurate. Other assays that are promising substitutes include, but are not limited to: 1) Cytokine Flow Cytometry (CFC), in which cytokine production is detected intracellularly in a cell population and which only requires about a six hour stimulation period; 2) MHC-peptide tetramer analysis in which isolated MHC-peptide tetramers are used to stimulate an antigen-specific response in PBL and bound cells can be counted by flow cytometry; and 3) Quantitative Reverse Transcription Polymerase Chain Reaction (QRT-PCR) assays in which the expression of one or more gene target, such as cytokines, can be monitored, permitting rapid quantitation of expression levels from a small sample of cells. Each of these assays are described in further detail in Keilholz et al., 2002 and in the literature. Any of the described assays may be used alone, or in combination with others to determine if a patient's PBL are capable of producing a suitable antigen-specific response. Of note, the compounds containing the EphA2 T-cell epitopes described herein are useful in the ELISPOT, CFC and tetramers assays described above, but not in the QRT-PCR assay, which requires design of suitable PCR primer and probe sets according to established methods.

Image analysis-assisted cytokine ELISPOT assay is a sensitive method for direct ex vivo monitoring of antigen-specific $CD4^+$ or $CD8^+$ T cells. The procedure measures both the frequency and cytokine signatures of antigen-specific T cells in freshly isolated cellular material. The assay determines various parameters of T cell immunity such as the clonal size (magnitude) and the Th1/Th2 effector class of the T cell pool. ELISPOT is a superior method through which the actual secretory processes of individual pharmacologically unmanipulated cells can be studied. The technology is non destructive and the lymphocytes can be preserved for further analysis. Under the ELISPOT technique, cytokine release can be detected at the single cell level, allowing for the determination of cytokine-producing cell frequencies. The ELISPOT assay uses plates coated with an antibody, typically an anti-cytokine antibody. In the Examples below, the plates are coated with IL-5 (Th2 cytokine profile) and IFN-γ (Th1 cytokine profile). The ELISPOT assay includes the steps of incubating cytokine producing cells, such as PBLs, in the antibody-coated plates in the presence of an antigen. The cells are washed away, leaving just the antibodies, some of which will be bound to its cytokine ligand. A standard "sandwich assay" is then performed in which tagged or labeled anti-cytokine antibody is bound to the previously bound cytokine and is detected by standard methods, such as by a standard biotin-avidin-HRP (horseradish peroxidase) method. Bound cytokine is therefore represented on the plate as a spot at the site of the complex. The colored spots are then counted and their size analyzed either visually or more commonly by computer analysis, providing data that is then used to calculate the cytokine secretion frequency.

Both ELISPOT assays and ELISAs are examples of sandwich assays. The term "sandwich assay" refers to an immunoassay where the antigen is sandwiched between two binding reagents, which are typically antibodies. The first binding reagent/antibody being attached to a surface and the second binding reagent/antibody comprising a detectable group. Examples of detectable groups include, for example and without limitation: fluorochromes, enzymes, epitopes for binding a second binding reagent (for example, when the second binding reagent/antibody is a mouse antibody, which is detected by a fluorescently-labeled anti-mouse antibody), for example an antigen or a member of a binding pair, such as biotin. The surface may be a planar surface, such as in the case of an ELISPOT assay or a typical grid-type array, as described herein, or a non-planar surface, as with coated bead array technologies, where each "species" of bead is labeled with, for example, a fluorochrome (such as Luminex technology, as described in U.S. Pat. Nos. 6,599,331, 6,592,822 and 6,268,222), or a quantum dot (for example, as described in U.S. Pat. No. 6,306,610).

The epitopes described herein are compounds that contain one or more EphA2 T-cell epitopes. The epitope can be, for example, with respect to T-cell epitopes defined by their binding to HLA-A2 and DR4, 1) peptides having one of the amino acid sequences: TLADFDPRV (SEQ ID NO: 2, residues 883-891); VLLLVLAGV (SEQ ID NO: 2, residues 546-554); VLAGVGFFI (SEQ ID NO: 2, residues 550-558); IMNDMPIYM (SEQ ID NO: 2, residues 58-66); SLLGLKDQV (SEQ ID NO: 2, residues 961-969); WLVPIGQCL (SEQ ID NO: 2, residues 253-261); LLWGCALAA (SEQ ID NO: 2, residues 12-20); GLTRTSVTV (SEQ ID NO: 2, residues 391-399); NLYYAESDL (SEQ ID NO: 2, residues 120-128); KLNVEERSV (SEQ ID NO: 2, residues 162-170); IMGQFSHHN (SEQ ID NO: 2, residues 666-674); YSVCNVMSG (SEQ ID NO: 2, residues 67-75); MQNIMNDMP (SEQ ID NO: 2, residues 55-63); or a sequence listed in one or more of FIGS. 5-17 or longer peptides containing those sequences; 2) peptides containing derivatives or conservative derivatives of those peptide sequences, in which one or more amino acids are deleted or are substituted with one or more different amino acids, the derivatives or conservative derivatives containing the T-cell epitopes defined by the peptide sequences listed above, 3) peptides, including fragments of EphA2, containing 2 or more of those peptide sequences or derivatives thereof, peptides containing the T-cell epitope defined by those peptide sequences, or peptide analogs or other compounds containing one or more of the T-cell epitopes defined by those peptide sequences.

In one embodiment, the epitope is a single peptide containing two or more of the amino acid sequences containing the T-cell epitope of: TLADFDPRV (SEQ ID NO: 2, residues 883-891); VLLLVLAGV (SEQ ID NO: 2, residues 546-554); VLAGVGFFI (SEQ ID NO: 2, residues 550-558); IMNDMPIYM (SEQ ID NO: 2, residues 58-66); SLLGLKDQV (SEQ ID NO: 2, residues 961-969); WLVPIGQCL (SEQ ID NO: 2, residues 253-261); LLWGCALAA (SEQ ID NO: 2, residues 12-20); GLTRTSVTV (SEQ ID NO: 2, residues 391-399); NLYYAESDL (SEQ ID NO: 2, residues 120-128); KLNVEERSV (SEQ ID NO: 2, residues 162-170); IMGQFSHHN (SEQ ID NO: 2, residues 666-674); YSVCNVMSG (SEQ ID NO: 2, residues 67-75); MQNIMNDMP (SEQ ID NO: 2, residues 55-63) or a sequence listed in one or more of FIGS. 5-17. Each sequence is separated from the other by a peptide spacer that may be of any length, but typically ranges from 0 to 10 amino acids in length. In Velders et al. J. Immunol. (2001) 166:5366-5373, an AAY trimer spacer greatly improved the efficacy of an a Human Papilloma Virus (HPV16) multivalent epitope string vaccine. The peptide can be engineered to ensure that protease cleavage sites are located between the epitope sequences to ensure proper processing of the peptide. This "string of beads" configuration can contain any number and combination of epitopes. De Groot et al. 2001, Velders et al. 2001 and Ling-Ling et al. J. Viral. (1997) 71:2292-2302 describe peptides having this configuration, methods for making and optimizing such constructs, methods for identifying candidate epitopes and recombinant systems useful in making such vaccines. The benefit of using a "string of beads" approach is that subdominant epitopes, or multiple copies of the same epitope may be included in a single peptide, thereby eliciting an immune response to an epitope or epitopes to which immunity is not normally elicited in a response to the native (i.e. EphA2) peptide. The concept of eliciting immune responses to such cryptic or subdominant epitopes is called "epitope spreading" and can lead to a more robust immune response than a typical immune response to native peptides.

One or more epitopes also may be combined in a chimeric peptide with a second amino acid sequence that has a desired functionality. The functionality can be immunogenic in nature, permitting affinity purification of the peptide. A protease cleavage site can be included between the EphA2 T-cell epitope peptide and the immunogenic portion. The functionality also can facilitate the delivery of the EphA2 T-cell epitope peptide, by including amino acid sequences that facilitate delivery of the peptide. One example of this is to include a portion of lactadherin or other protein to facilitate presentation of the peptide to dendritic cells in membrane vesicles or nanoparticles, such as exosomes. Methods for modifying and expressing chimeric peptides for incorporation into membrane vesicles are described in International Patent Publication No. WO 03/016522.

The epitope, in any form described above, can be administered by any useful route to vaccinate or otherwise elicit an immune response in a patient. In one embodiment, the epitope is injected into the patient, optionally with an adjuvant, such as Freund's Incomplete Adjuvant, Freund's Complete Adjuvant, or as an exosome, as described above. The epitope can be delivered in a variety of compositions which include the epitope and any desirable, pharmaceutically acceptable carrier. "Carrier" includes as a class, without limitation, any compound or composition useful in facilitating storage, stability, administration and/or delivery of the active ingredients described herein, including, without limitation, suitable vehicles, solvents, diluents, excipients, pH modifiers, buffers, salts, colorants, flavorings, rheology odifiers, lubricants, coatings, fillers, antifoaming agents, erodeable polymers, hydrogels, surfactants, emulsifiers, adjuvants, preservatives, phospholipids, fatty acids, mono-, di- and triglycerides and derivatives thereof, waxes, oil and water, as are broadly known in the pharmaceutical arts. So long as the epitope is delivered to lymphoid cells, the route is immaterial. Atypical route of administration is intramuscular injection. The epitope can be administered once or multiple times over a desired time period to elicit a desired immune response. Suitable intervals for administering multiple doses typically range from once a week to once a year, but typically ranges from once every seven to 90 days, and more typically, once every seven to 30 days. Optimal administration intervals may be gauged by a patient's immune response, and the severity of the patient's condition. The amount of the epitope administered also may vary greatly, depending, among other parameters, upon the structure of the epitope, the route of delivery and the patient's health status. In any case, the amount of epitope administered at any given time to elicit an immune response to the epitope is an amount effective to do so. Similarly, the number of times the epitope is administered and the interval for administering multiple doses is a number and interval effective to elicit an immune response to the epitope.

The epitope also may be delivered to a patient by liposomes. Liposomes can be directed to the site of lymphoid cells, where the liposomes then deliver the selected epitope composition. Liposomes for use are formed from typical vesicle—forming lipids, which include neutral and negatively charged phospholipids and a 5-sterol, such as cholesterol. The selection of lipids is generally guided by consideration of, for example, liposome size, acid lability and stability of the liposomes in the bloodstream. A variety of methods are available for preparing liposomes, as described in Szoka et al., Ann. Rev. Biophys. Bioeng. 9:467 (1980) and U.S. Pat. Nos. 4,235,871, 4,501,728, 4,837,028 and 5,019,369.

The epitopes also may be delivered in the presence of heat shock proteins. Heat shock proteins act as molecular chaperones in the cells, ensuring proper folding of nascent peptides into proteins and shuttling new and old proteins inside the cell. Heat shock proteins are believed to play a role in the presentation of peptides on the cell surface to help the immune system recognize diseased cells. U.S. Pat. Nos. 5,935,576, 6,007,821 and 6,017,540 describe such uses for heat shock proteins, methods of making heat shock protein complexes and treatment methods.

An effective immune response also can be elicited by ex vivo methods. in such methods, antigen is presented to PBL populations of antigen presenting cells (often referred to as pulsing APCs), such as dendritic cells, obtained from a patient in vitro, and the immune-stimulated cells are delivered back to the patient. This method ensures that the epitopes are delivered to the APCs and avoids both any potential toxicity to the patient of the peptide and typically requires lesser amounts of epitope. Methods for isolating PBLs, APCs and DCs are well known, and the epitope may be delivered to the APCs in vitro in any form, including by directly depositing the epitope on the cells, or by liposome or exosome delivery, as described herein, alone or in the presence of additional factors, such as heat shock proteins or appropriate cytokines.

Recent reports suggest that cross-linking of EphA2 on the cell surface of tumor cells by a ligand agonist provokes EphA2 phosphorylation, internalization and degradation (Walker-Daniels et al., Mol. Cancer. Res. 1: 79-87, 2002). This triggered degradation of EphA2 protein is believed to result in the acute generation of EphA2 epitope presented by MHC class I and/or class II proteins, making the tumor more easily recognized by EphA2-specific T cells, and potentially resulting in improved clinical eradication of cancer cells in vivo. This supports the concerted use of EphA2-based vaccines to expand and activate effector anti-EphA2 T cells in cancer patients with EphA2-ligand agonists to increase the likelihood for productive recognition of tumor cells by vaccine-induced lymphocytes in combinational immunotherapy approaches. EphA2 ligand agonists could take the form of, but would not be restricted to, anti-EphA2 antibodies, EphrinA1-Ig constructs or synthetic peptides that induce degradation of EphA2 protein in treated tumor cells.

In one embodiment, a patient is administered an EphA2 ligand or an agonist thereof. The EphA2 ligand or agonist thereof can be a binding reagent, such as an antibody (for example a monoclonal antibody, or a derivative or an analog of an antibody, including without limitation: Fv fragments; single chain Fv (scFv) fragments; Fab' fragments; F(ab')2 fragments; camelized antibodies and antibody fragments; multivalent versions of the foregoing; monospecific or bispecific antibodies, such as disulfide stabilized Fv fragments, scFv tandems ((scFv)$_2$ fragments), antibody multimers, which typically are covalently linked or otherwise stabilized (for example and without limitation, leucine zipper or helix stabilized); scFv fragments; recombinant antibodies or antibody fragments), or in vitro-generated EphA2-specific compounds, such as aptamers and compounds generated by phage display selection and propagation methods. The EphA2 ligand or agonist thereof can be ephrinA1 or an agonist thereof.

The EphA2 ligand or agonist thereof can be delivered to a patient by any effective route, in any effective amount and by any effective interval, as described above in reference to the EphA2 T-cell receptor epitope. Delivery of the EphA2 ligand or agonist thereof is in combination with the delivery of the EphA2 T-cell receptor epitope-containing compounds, and a therapeutic regimen typically, but not necessarily alternates delivery of the EphA2 T-cell receptor epitopes and the EphA2 ligand or agonist thereof. In one embodiment, the EphA2 T-cell receptor epitopes are delivered to a patient either directly by the direct or ex vivo methods described above, and one week later, the EphA2 ligand or agonist thereof is administered. This is repeated any desired and effective number of times, with one treatment per week, alternating between the EphA2 T-cell receptor epitopes and the EphA2 ligand or agonist thereof.

Any peptide described herein can be manufactured by any of the myriad of known recombinant methods for producing a peptide, or can be synthesized by common protein synthesis methods, such as by solid phase chemistries as are broadly known. In a recombinant method, a gene is prepared that contains an appropriate promoter, terminator and a coding region that encodes the desired peptide. The coding region also can encode signal sequences enabling secretion of the peptide by cells and/or suitable tags, preferably cleavable, that permit affinity purification of the peptide.

A nucleic acid containing a gene for expressing an EphA2 T-Cell receptor epitope in a human cell also may be delivered directly to a patient, or ex vivo to a patient's cells (for delivery back into the patient) such that the cells of the patient express the epitope, thereby eliciting an immune response. Delivery of a gene, rather than just the epitope can result in a more robust immune response resulting from the extended expression of the gene in the patient's cells. The nucleic acid can be delivered by viral-mediated (such as by a recombinant adenovirus, adeno-associated virus or vaccinia virus) or non-viral-mediated delivery methods (such as by liposome or by direct injection of naked nucleic acid, for instance into muscle).

EXAMPLES

Example 1

Reactivity of PBLs Against EphA2 T-Cell Peptide Epitopes

Peripheral Blood and Tumor Specimens. Peripheral blood samples were obtained by venipuncture from 40 patients diagnosed with RCC and 14 normal individuals and were collected into heparinized tubes. Peripheral blood lymphocytes (PBLs) were isolated by centrifugation on a Ficoll-Hypaque gradient (LSM, Organon-Teknika, Durham, N.C.). RCC tumor lesions and matched normal kidney tissue were surgically-resected and paraffin-embedded. Informed consent under an IRB-approved protocol was obtained from all patients prior to sample acquisition. Patient and normal donor information is provided in Table 1. All individuals included were HLA-A2 positive or/and HLA-DR4 positive, as determined by fluorescence-activated cell sorter analysis using the HLA-A2-specific antibodies (BB7.2 and MA2.1) and HLA-DR4-specific antibody (anti-HLA-DR4 monoclonal antibody clone 359-13F10, IgG, kindly provided by Dr. Janice Blum, Indiana University School of Medicine, Indianapolis, Ind.). Among the RCC patients and normal individuals, 9 patients and 6 normal individuals expressed both the HLA-A2 and HLA-DR4 major histocompatibility antigens.

TABLE 1

HLA-A2 and/or DR4 positive RCC patients evaluated

| Patient | Age | Sex | Stage | Treatment | Disease status at time of evaluation (Months) | A2(+/−) | DR4(+/−) |
|---|---|---|---|---|---|---|---|
| SLR30-pre | 63 | F | I | none | Local Dis. | + | − |
| SLR31 | 66 | M | I | none | Local Dis. | + | − |
| SLR32 | 62 | F | I | none | Local Dis. | + | − |
| SLR33 | 54 | F | I | none | Local Dis. | + | − |
| SLR34 | 71 | M | I | none | Local Dis. | + | + |
| SLR35 | 75 | F | I | none | Local Dis. | + | + |
| SLR36-pre | 60 | M | I | none | Local Dis. | + | + |
| SLR37 | 52 | M | I | none | Local Dis. | + | − |
| SLR38-pre | 69 | M | I | none | Local Dis. | + | − |
| SLR39 | 65 | M | I | S | NED (3) | + | − |
| SLR30-post | 63 | F | I | S | NED (1.5) | + | − |
| SLR40 | 53 | M | I | S | NED (3) | + | − |
| SLR36-post | 60 | M | I | S | NED (2) | + | + |
| SLR41 | 64 | F | I | S | NED (2) | + | − |
| SLR38-post | 69 | M | I | S | NED (2) | + | − |
| SLR42 | 58 | F | I | S | Local Dis. (3) | + | − |
| SLR43 | 53 | F | I | S | Local Dis. (1.5) | + | − |
| SLR44-pre | 69 | M | IV | none | Mets | + | − |
| SLR45 | 65 | M | IV | none | Mets | + | − |
| SLR46 | 45 | F | IV | none | Mets | + | − |
| SLR47 | 53 | F | IV | S | NED (1.5) | + | − |
| SLR48 | 54 | M | IV | S | Mets (61) | + | − |
| SLR49 | 52 | F | IV | S, R, IFN-α, IL-2 | Mets (41) | + | − |
| SLR44-post | 69 | M | IV | S | Mets (2) | + | − |
| SLR50 | 54 | M | IV | S, R, C | Mets (21) | + | − |
| SLR51 | 41 | M | IV | S, R, IL-2 | Mets | + | + |
| SLR52 | 58 | M | IV | S, R, IFN-α | Mets | + | + |
| SLR53 | 52 | M | IV | S | Mets | + | − |
| SLR54 | 49 | F | IV | IL-2, C | Mets | + | + |
| SLR55 | 79 | M | IV | IFN-α, C | Mets | + | + |
| SLR56 | 56 | M | IV | R, IL-2, IFN-α, C | Mets | + | − |
| SLR57 | 68 | F | IV | none | Mets | + | − |
| SLR58 | 55 | F | IV | none | Mets | + | + |
| SLR59 | 52 | F | I | none | Local Dis. | − | + |
| SLR60-pre | 58 | M | I | none | Local Dis. | − | + |
| SLR61 | 60 | M | I | none | Local Dis. | − | + |
| SLR62 | 64 | M | I | S | NED (3) | − | + |
| SLR63 | 53 | F | I | S | NED (1.5) | − | + |
| SLR60-post | 58 | M | I | S | NED (2) | − | + |
| SLR64 | 65 | M | I | S | NED (10) | − | + |
| SLR65 | 53 | M | II | S | Local Dis. | − | + |
| SLR66 | 45 | M | IV | none | Mets | − | + |
| SLR67 | 57 | M | IV | C, R | Mets | − | + |
| SLR68 | 69 | M | IV | S, R, C | Mets | − | + |
| SLR69 | 49 | M | IV | S, C, R, IL-2, IFN-α | Mets | − | + |

In Table 1, individual CCF designations reflect specimen number based on date harvested. In 5 cases, both pre- and (6 weeks) post-therapy blood specimens were available for analysis, as indicated. Where indicated, the time of peripheral blood isolation (in months) post-therapy is provided. Abbreviations used: C, Chemotherapy; IFN-γ, recombinant Interferon-alpha therapy; IL-2, recombinant Interleukin-2 therapy; Mets, Metastatic Disease; NED, No evidence of disease; R, Radiotherapy; S, Surgery. HLA-A2 and -DR4 status was determined using allele-specific monoclonal antibodies and flow cytometry gating on peripheral blood monocytes, as described in Materials and Methods.

Cell Lines and Media. The T2.DR4 (HLA-A2$^{+/−}$DRβ1*0401$^+$; Pratt, R. L. et al. Oncogene 21:7690-7699 (2002)) cell line (kindly provided from Dr. Janice Blum, Indiana University School of Medicine, Indianapolis, Ind.) was used as the peptide-presenting cell in ELISPOT assay. The following SLR20-SLR26 clear cell RCC lines were evaluated in Western Blotting analyses. The normal human proximal tubular epithelial kidney cell line HK-2 (American Type Tissue Collection, ATCC, Rockville, Md.) was also evaluated in these analyses. Hypothetically, HK-2 represents a normal control cell line, although it has been transformed by transfection with the HPV-16 E6/E7 genes (Ryan M J, et al. Kidney Int. 45:48-57 (1994)). The EphA2+ PC-3 prostate carcinoma cell line was included as a positive control for Western blotting (Walker-Daniels J, et al. Prostate 41:275-280 (1999)). All cell lines were maintained in RPMI-1640 culture medium supplemented with 10% heat-inactivated fetal bovine serum, 100 U/ml penicillin, 100 μg/ml streptomycin and 10 mM L-glutamine (all reagents from GIBCO/Life Technologies, Grand Island, N.Y.) in a humidified atmosphere of 5% $CO_2$ at 37° C.

Peptides selection and synthesis. The protein sequence of EphA2 protein was obtained from GENBANK (accession number AAH37166; FIG. 1) and analyzed for HLA-A0201 and HLA-DRβ1*0401 binding peptides using neural network algorithms (Honeyman M C, Brusic V, Stone N L, Harrison L C., "Neural network-based prediction of candidate T-cell epitope," Nat. Biotechnol. (1998) 16:966-969 and Southwood S, Sidney J, Kondo A, del guercio M-F, Appella E, Hoffman S, Kubo R T, Chesnut R W, Grey H M, Sette A., "Several common HLA-DR types share largely overlapping peptide binding repertoires," J. Immunol. (1998) 160:3363-3383). The top ten candidate HLA-A2 binding peptides were then analyzed for their ability to be generated by proteasomal cleavage using the PAProC prediction algorithm (C. Kuttler, A. K. Nussbaum, T. P. Dick, H.-G. Rammensee, H. Sehild, K. P. Hadeler, "An algorithm for the prediction of proteasomal cleavages," J. Mol. Biol. (2000) 298:417-429; A. K. Nussbaum, C. Kuttler, K. P. Hadeler, Rammensee, H. Schild, PAProC: A Prediction Algorithm for Proteasomal Cleavages available on the WWW, Immunogenetics 53 (2001), 87-94; and A. K. Nussbaum, "From the test tube to the World Wide Web—The cleavage specificity of the proteasome," dissertation, University of Tuebingen, Germany, 2001, with only those peptides capable of being processed by the proteasome selected for synthesis. All peptides were synthesized by Fmoc chemistry. Peptides were >90% pure based on HPLC profile and MS/MS mass spectrometric analysis. In total, five HLA-0201 and three HLA-DR0401 predicted binding peptides that received high binding scores in this study (Table 2), were evaluated.

TABLE 2

Selection of EphA2 Peptides for Analysis

Selected HLA-A2 Presented EphA2 Peptides:

| Selected Start Amino Acid | AA Sequence of Nonamer | Binding Score* | Proteasome Generated? | Synthesized For Analysis |
|---|---|---|---|---|
| 883 | TLADFDPRV[1] | 1084 | YES | YES |
| 546 | VLLLVLAGV[2] | 1006 | YES | YES |
| 550 | VLAGVGFFI[3] | 556 | NO | NO |
| 58 | IMNDMPIYM[4] | 138 | NO | NO |
| 961 | SLLGLKDQV[5] | 127 | YES | YES |
| 253 | WLVPIGQCL[6] | 98 | NO | NO |
| 12 | LLWGCALAA[7] | 71 | NO | NO |
| 391 | GLTRTSVTV[8] | 70 | YES | YES |
| 120 | NLYYAESDL[9] | 68 | NO | NO |
| 162 | KLNVEERSV[10] | 49 | YES | YES |

*The higher the binding score, the greater the stability of the predicted peptide-MHC complex. Binding scores and qualitative determination of proteasomal processing were predicted using on-line algorithms as described in Materials and Methods.
[1]SEQ ID NO: 2, residues 883-891.
[2]SEQ ID NO: 2, residues 546-554.
[3]SEQ ID NO: 2, residues 550-558.
[4]SEQ ID NO: 2, residues 58-66.
[5]SEQ ID NO: 2, residues 961-969.
[6]SEQ ID NO: 2, residues 253-261.
[7]SEQ ID NO: 2, residues 12-20.
[8]SEQ ID NO: 2, residues 391-399.
[9]SEQ ID NO: 2, residues 120-128.
[10]SEQ ID NO: 2, residues 162-170.

Selected HLA-DR4 Presented EphA2 Peptides:

| Sequence Start Core AA # | AA Sequence of Nonamer | Binding Score | Synthesized For Analysis |
|---|---|---|---|
| 666 | IMGQFSHHN[1] | 577 | $_{663}$EAGIMGQFSHHNIIR[2] |
| 67 | YSVCNVMSG[3] | 95 | $_{63}$PIYMYSVCNVMSG[4] |
| 55 | MQNIMNDMP[5] | 39 | $_{53}$DLMQNIMNDMPIYMYS[6] |

[1]SEQ ID NO: 2, residues 666-674.
[2]SEQ ID NO: 2, residues 663-677.
[3]SEQ ID NO: 2, residues 67-75.
[4]SEQ ID NO: 2, residues 63-75.
[5]SEQ ID NO: 2, residues 55-63.
[6]SEQ ID NO: 2, residues 53-68.

Antigen Stimulation of PBLs. PBLs were resuspended at $10^7$/ml in AIM-V medium (GIBCO/Life Technologies) and were incubated for 60 min at 37° C. in a humidified 5% $CO_2$ incubator. Nonadherent (T cell-enriched) cells were gently washed out with PBS and subsequently frozen. The plastic adherent cells were cultured in AIM-V medium supplemented with 1000 units/ml rhGM-CSF (Immunex Corporation, Seattle, Wash.) and 1000 units/ml rhIL-4 (Schering- Plough, Kenilworth, N.J.). Seven days later, dendritic cells (DCs) were harvested and used to stimulate autologous CD8+ or CD4+ T cells. Non-adherent autologous cells were used as "enriched" sources of T cell responders. CD8+ T cells (in HLA-A2-positive patients and healthy donors) or CD4 T cells (in HLA-DR4-positive patients and healthy donors) were positively isolated to >98% purity using specific magnetic beads (MACS; Miltenyi Biotec, Auburn, Calif.). Two hundred thousand DCs were cocultured with $2\times10^6$ CD8+ or CD4+ T cells with 10 µg/ml peptide for 1 week. On day 7 of in vitro stimulation, the responder CD8+ T cells or CD4+ T cells were harvested and analyzed in ELISPOT assays.

IFN-γ and IL-5 ELISPOT assays for Peptide-Reactive CD8+ T cells and CD4+ T cell Responses. To evaluate the frequencies of peripheral blood T cells recognizing peptide epitopes, ELISPOT assays for IFN-γ and IL-5 were performed, as previously described (Tatsumi T, et al. J. Exp. Med. 196; 619-628, 2002). CD8+ T cell responses were evaluated by IFN-γ ELISPOT assays only, while CD4+ T cell responses were evaluated by both IFN-γ (Th1) and IL-5 (Th2) ELISPOT assays. For ELISPOT assays, 96-well multiscreen hemagglutinin antigen plates (Millipore, Bedford, Mass.) were coated with 10 mg/ml of antihuman IFN-γ mAb (1-D1K; Mabtech, Stockholm, Sweden) or 5 µg/ml of anti-human IL-5 (Pharmingen-BD, San Diego, Calif.) in PBS (GIBCO/Life Technologies) overnight at 4° C. Unbound antibody was removed by four successive washing with PBS. After blocking the plates with RPMI-1640/10% human serum (1 hr at 37° C.), $10^5$ CD8+ T cells or CD4+ T cells and T2DR4 cells ($2\times10^4$ cells) pulsed with 10 µg/ml synthetic peptides were seeded in triplicates in multi-screen hemagglutinin antigen plates. Control wells contained CD8+ or CD4+ T cells with T2.DR4 cells pulsed with HIV-nef$_{190-198}$ peptide (AFHHVAREL, SEQ ID NO: 3) or Malaria-CS$_{326-345}$ peptide (EYLNKIQNSLSTEWSPCSVT; SEQ ID NO: 4), respectively, or T2.DR4 cells alone. Culture medium was AIM-V (GIBCO/Life Technologies) at a final volume of 200 µl/well. The plates were incubated at 37° C. in 5% $CO_2$ for 24 hr for IFN-γ assessments, and 40 hr for IL-5 assessments. After incubation, the supernatants of the culture wells were harvested for ELISA analyses, and cells were removed by washing with PBS/0.05% Tween 20 (PBS/T). Captured cytokines were detected at sites of their secretion by incubation for 2 hr with biotinylated mAb anti-human IFN-γ (7-B6-1; Mabtec) at 2 µg/ml in PBS/0.5% BSA or biotinylated mAb anti-human IL-5 (Pharmingen) at 2 µg/ml in PBS/0.5% BSA. Plates were washed six times with PBS/T, and avidin-peroxidase complex (diluted 1:100; Vectastain Elite Kit; Vector Laboratories, Burlingame, Calif.) was added for 1 hr. Unbound complex was removed by three successive washes with PBS/T, then with three rinses with PBS alone. AEC substrate (Sigma, St. Louis, Mo.) was added and incubated for 5 min for the IFN-γ ELISPOT assay and the TMB substrate for peroxidase (Vector Laboratories) was added and incubated for 10 min for the IL-5 ELISPOT assay. Spots were imaged using the Zeiss AutoImager (and statistical comparison determined using a Student two-tailed T-test analysis). The data are represented as mean IFN-γ or IL-5 spots per 100,000 CD4+ T cells analyzed.

ELISAs. The supernatants harvested from CD4+ T cell ELISPOT plates were analyzed in TGF-β and IL-10 ELISAs. Supernatants were isolated from ELISPOT plates at the end-point of the culture period and frozen at −20° C. until analysis in specific cytokine ELISAs. Cytokine capture and detection antibodies and recombinant cytokine were purchased from BD-Pharmingen (San Diego, Calif.) and used in ELISA assays per the manufacturer's instructions. The limit of detection for the TGF-β and IL-10 assays was 60 pg/ml and 7 pg/ml, respectively.

Western blot analysis. Tumor cells ($5-10\times10^6$) were analyzed for EphA2 expression via Western blots using the anti-human EphA2 polyclonal antibody (clone: H-77) (Santa Cruz Biotechnology, Inc., Santa Cruz, Calif.). Cell pellets were lysed using 200 of 1% NP-40 in PBS containing protease inhibitors (Complete, Boehringer Mannheim, Indianapolis, Ind.) for 1 hour on ice. After centrifugation at 13,500×g for 30 minutes, the supernatant was mixed 1:1 with SDS-PAGE running buffer and proteins separated on 10% PAGE gels, prior to electro-blotting onto nitrocellulose membranes (Millipore, Bedford, Mass.). Blots were imaged on Kodak X-Omat Blue XB-1 film (NEN Life Science Products, Boston, Mass.) using horseradish peroxidase (HRP)-conjugated goat anti-rabbit Ig (Biorad, Hercules, Calif.) and the ECL chemiluminescence detection kit (NEN Life Science Products).

Immunohistochemistry for EphA2 in RCC tissue. RCC tumor specimens were obtained surgically under an IRB-approved protocol and paraffin-embedded. Five µm sections were de-paraffinized and rehydrated in dd$H_2O$ and then PBS. Anti-EphA2 mAb (Ab 208; mIgG1) or isotype-matched control mAb was incubated on sections for 1 h at RT. After PBS washing, sections were incubated with biotinylated goat anti-rabbit IgG (Vector Laboratories) for 20 min at room temperature, and after washing, were then incubated with avidin-biotin-complex peroxidase (Vectastain ABC kits, Vector Laboratories). After a subsequent wash, reaction products were developed by Nova Red substrate kit (Vector Laboratories), and nuclei were counterstained with hematoxylin. The expression of EphA2 was evaluated independently by two investigators with a microscope under 40× magnification.

Statistical Analysis. Statistical significance of differences between the two groups was determined by applying Student's t test or two sample t test with Welch correction after each group had been tested for equal variance. Statistical significance was defined as a p value of less than 0.05.

Results

Expression of EphA2 in tumor cell lines and in RCC tissues. EphA2 was overexpressed in malignant renal epithelial cells. Western blot analyses were used to evaluate EphA2 protein levels in RCC cell lines (FIG. 18). Metastatic RCC lines tended to express EphA2 more strongly than primary RCC lines, approaching the strong staining previously noted for the prostate carcinoma PC-3 (Walker-Daniels J, et al. Prostate 41; 275-280, 1999). While used as a model for normal proximal kidney endothelial cells, the HK-2 cell line is HPV-16 E6/E7-transformed and expresses levels of EphA2 consistent with that observed for primary RCC lines. Normal PBLs failed to express detectable levels of EphA2 protein. Consistent with these findings, immunohistochemical analyses performed on paraffin-embedded RCC specimens (FIG. 19) verified strong expression of EphA2.

Figure 19A:
FIG. 19 are photomicrographs showing expression of EphA2 in RCC cell lines.
Figure 19B:
Figure 19C:
Figure 19D:
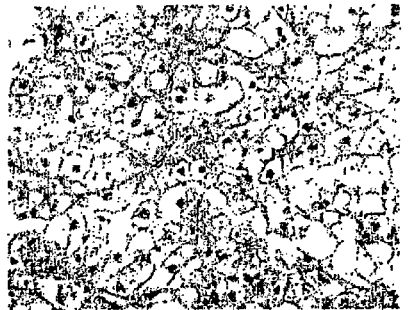

In FIG. 18, anti-EphA2 and control anti-β-actin antibodies were used in performing Western Blot analyses of lysates generated from the indicated RCC cell lines, the normal kidney tubular epithelial cell line HK2 and normal peripheral blood lymphocytes (PBLs) (negative control). Primary and metastatic clear cell RCC lines were assessed, as indicated. The PC3 prostate cell line and normal donor PBLs served as positive and negative controls. In FIGS. 19A-D, primary (FIGS. 19A and 19B) and metastatic (FIGS. 19C and 19D) RCC paraffin tissue sections were stained using anti-EphA2 antibody (Ab 208; FIGS. 19A and 19C) or isotype control antibody (FIGS. 19B and 19D) in immunohistochemical analyses (40× magnification).

Identification of EphA2 epitopes recognized by T cells. To identify potential T cell epitopes, the EphA2 protein sequence was subjected to algorithms designed to identify putative HLA-A2 binding motifs and sites of proteasomal cleavage. Similarly, a neural network algorithm was used to identify EphA2 peptide sequences that would be predicted to bind HLA-DR4 and have the potential to represent CD4+ T cell epitopes (Honeyman M et al., 1998). In aggregate, 8 peptides were synthesized for subsequent analyses: 5 peptides were predicted to serve as CTL epitopes and 3 peptides were predicted to serve as Th epitopes (Table 2).

Peripheral blood T cells were isolated from normal HLA-A2+ and/or -DR4+ donors and stimulated with autologous DCs that had be previously loaded with relevant synthetic peptides. Responder T cells were subsequently evaluated for specific reactivity against peptide-pulsed T2.DR4 (HLA-A2+/DR4+) antigen-presenting cells and renal cell carcinoma cell lines that expressed both the EphA2 antigen and HLA-A2 and/or HLA-DR4. The IFN-γ ELISPOT assay was used to evaluate 8 HLA-A2+ donor CD8+ T cell responses to the 5 putative CTL epitopes and 7 HLA-DR4+ donor CD4+ T cell reactivities against the 3 potential Th epitopes.

Each peptide was recognized by at least one normal donor (Table 3), and only one (HLA-DR4) donor failed to respond to any of the EphA2 (Th) epitopes. Among the HLA-A2 donors, the EphA2$_{546-554}$ and EphA2$_{883-891}$ peptides were most commonly reacted against (each in 6/8 donors evaluated), with the responses to EphA2$_{883-891}$ typically being of a higher frequency. Among the HLA-DR4+ donors evaluated, 6/7 donors responded against at least one predicted EphA2-derived Th epitope, with responses against the EphA$_{63-75}$ and EphA2$_{663-677}$ most prevalent. When cloned T cells were derived from these bulk populations of responder T cells, they were capable of recognizing EphA2+ RCC lines in the appropriate HLA class I- or class II-(HLA-A2 or -DR4) restricted manner (data not shown).

TABLE 3

Normal donor T cell responses to putative EphA2-derived peptide epitopes

HLA-A2-Presented EphA2 Peptides:
CD8+ T Cell Response to Peptide on T2.DR4[a]:

| | Normal Donor # | | | | |
|---|---|---|---|---|---|
| | 162 | 391 | 546 | 883 | 961 |
| A2-1 | 9 | 0[b] | 31 | 0 | 2 |
| A2-2 | 40 | 81 | 14 | 85 | 21 |
| A2-3 | 3 | 14 | 10 | 0 | 21 |
| A2-4 | 2 | 0 | 11 | 58 | 0 |
| A2-5 | 11 | 0 | 14 | 172 | 4 |
| A2-6 | 0 | 91 | 76 | 145 | 13 |
| A2-7 | 132 | 0 | 0 | 37 | 0 |
| A2-8 | 15 | 0 | 0 | 165 | 0 |
| Total Responses: | 5/8 | 3/8 | 6/8 | 6/8 | 3/8 |

HLA-DR4-Presented EphA2 Peptides:
CD4+ T Cell Response to Peptide on T2.DR4[a]:

| | Normal Donor # | | |
|---|---|---|---|
| | 53 | 63 | 663 |
| DR4-1 | 43 | 11 | 21 |
| DR4-2 | 38 | 36 | 57 |
| DR4-3 | 4 | 7 | 14 |
| DR4-4 | 0 | 0 | 0 |
| DR4-5 | 0 | 156 | 41 |
| DR4-6 | 0 | 121 | 67 |
| DR4-7 | 54 | 48 | 72 |
| Total Responses: | 3/7 | 6/7 | 6/7 |

[a]T cell responses over T2.DR4 pulsed with control peptides/100,000 T cells.
[b]A value of "0" reflects a frequency <1/100,000 T cells. T cell reactivity against T2.DR4 cells pulsed with the HLA-A2-presented HIV-nef$_{190-198}$ epitope served as the CD8+ T cell negative control, while HLA-DR4-presented Malarial circumsporozooite (CS)$_{326-345}$ epitope served as the CD4+ T cell negative control. These control values were subtracted from experimental determinations in order to determine EphA2-specific T cell # responder spot numbers.
Values significantly (p < 0.05) elevated over T2.DR4+ control peptide values are underlined.

Analysis of peptide-specific IFN-γ release by peripheral blood CD8+ T cells in ELISPOT assays. Peripheral blood CD8+ T cells responses was assessed against these sequences in 29 HLA-A2+ RCC patients (Table 1) and 10 HLA-A2+ normal donors. CD8+ T cells were enriched to 98% purity for all experiments. Responses were evaluated using IFN-γ ELISPOT assays after 7 day "primary" in vitro stimulations.

Figure 20:
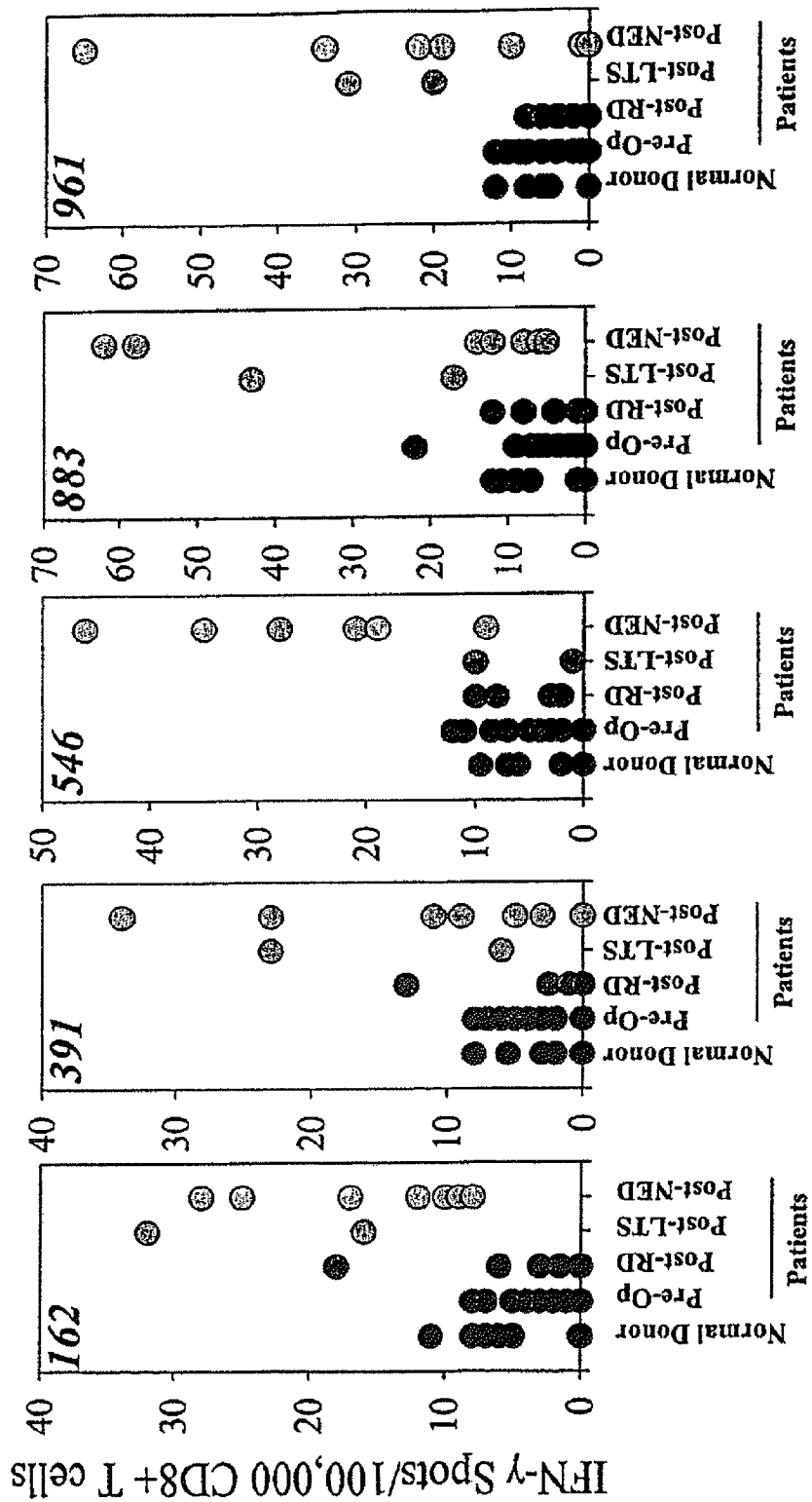
FIG. 20 provides graphs showing IFN-γ ELISPOT (enzyme-linked immunospot) analysis of RCC patient CD8$^+$ T cell responses to EphA2-derived epitopes versus disease status.

In FIG. 20, peripheral blood CD8+ T cells were isolated from HLA-A2+ normal donors or patients with RCC and stimulated with immature, autologous dendritic cells pre-pulsed with the individual EphA2-derived epitopes, as outlined in Materials and Methods. After one week, responder T cells were analyzed in IFN-γ ELISPOT assays for reactivity against T2.DR4 (HLA-A2+) cells pulsed with the indicated EphA2 epitope. Data are reported as IFN-γ spots/100,000 CD8+ T cells and represent the mean of triplicate determinations. T cell reactivity against T2.DR4 cells pulsed with the HLA-A2-presented HIV-nef$_{190-198}$ epitope served as the negative control in all cases, and this value was subtracted from all experimental determinations in order to determine EphA2-specific spot numbers. Each symbol within a panel represents an individual donor's response.

Figure 21:
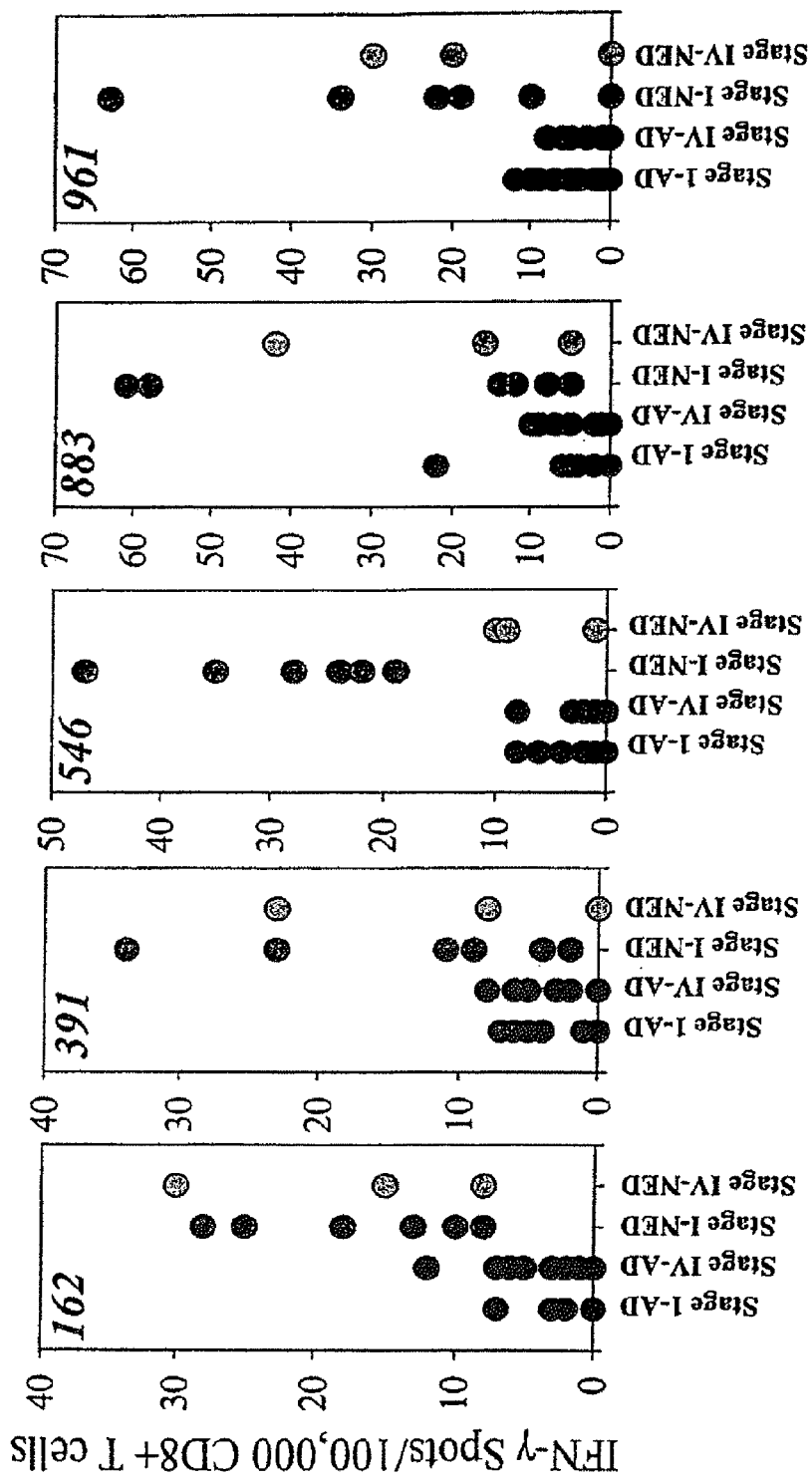
FIG. 21 provides graphs showing IFN-γ ELISPOT analysis of RCC patient CD8$^+$ T cell responses to EphA2-derived epitopes versus disease stage.

As shown in FIG. 20, the frequencies of CD8+ T cell responses against EphA2 peptides in HLA-A2+ patients prior to surgery (Pre-Op) or patients with residual disease after surgery (Post-RD) were as low as those observed in normal HLA-A2+ donors. In contrast, elevated ELISPOT reactivity to EphA2 epitopes was observed in RCC patients who were categorized as disease-free (no-evidence of disease: NED) after surgery (Post-NED). Interestingly, CD8+ T cells from RCC patients exhibiting long-term survival (Post-LTS; >2 year survival post-surgery) despite having some degree of active disease, also showed elevated ELISPOT reactivity to EphA2 CTL epitopes. There were no significant differences in anti-EphA2 CD8+ T cell responses when comparing patients with Stage I vs. Stage IV, if the patient had active disease (FIG. 21, showing data reported in FIG. 20 re-plotted as a function of disease-stage). Only patients that were analyzed at a time when they were disease-free (i.e. no evidence of disease, NED) or if they were long-term survivors, exhibited CD8+ T cells with elevated reactivity to EphA2 epitopes (FIG. 21).

Figure 22:
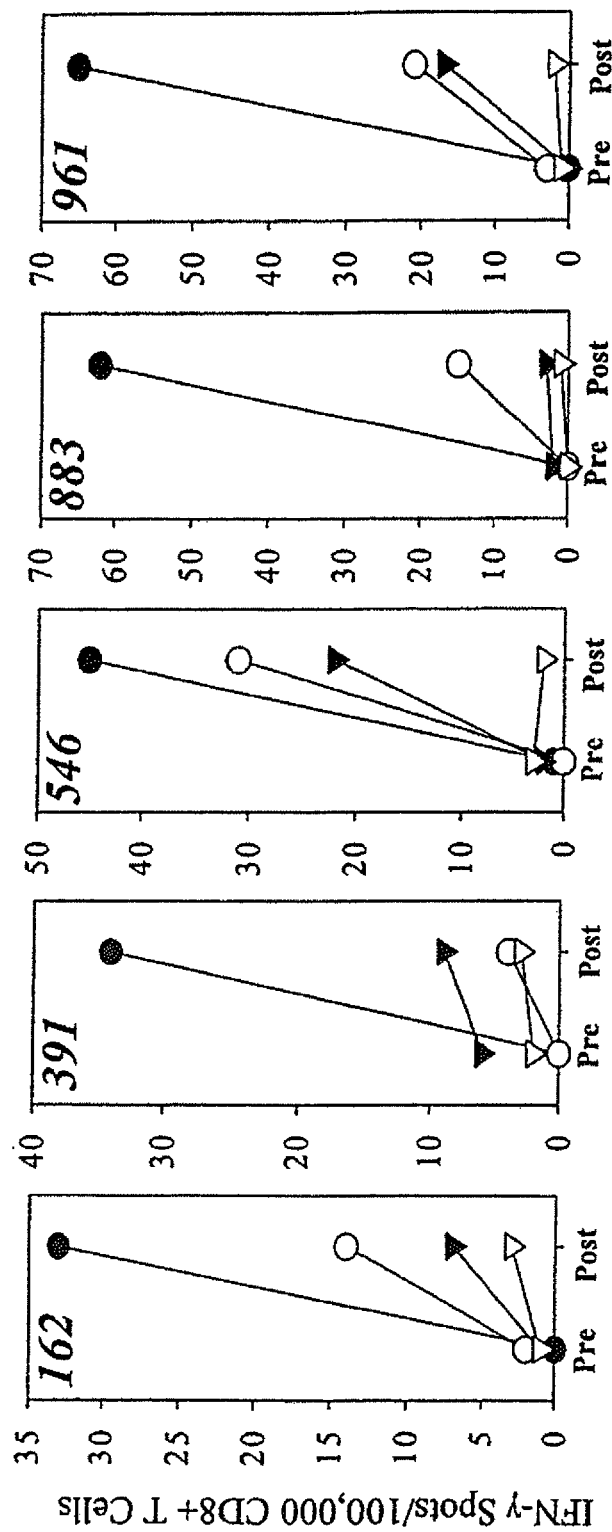
FIG. 22 provides graphs showing observed changes in peripheral blood CD8+ T cell responses to EphA2 epitopes pre-versus post-surgery in 4 HLA-A2$^+$ patients with RCC.

The change of CD8+ T cell reactivity against EphA2 peptides pre- and post-therapy in 4 HLA-A2+ patients was evaluated. In FIG. 22, Peripheral blood CD8+ T cells were isolated pre- and (6 week) post-surgery from patients with RCC, and evaluated for reactivity to EphA2 epitopes in IFN-γ ELISPOT assays, as outlined in the FIG. 20 description, above. The three Stage I RCC patients (●, ○, ▼) were rendered free of disease as a result of surgical intervention, while the single Stage IV RCC patient (▽) had residual disease after surgery. Each symbol within a panel represents an individual patient's response. Three of these individuals were Stage I patients who had local disease prior to surgical intervention, while the remaining patient had Stage IV disease. Notably, CD8+ T cell reactivity against EphA2 peptides was very low prior to surgery in all four RCC patients. After being rendered free of disease, CD8+ T cell reactivity against EphA2-derived CTL epitopes was significantly increased in each of the three Stage patients. In marked contrast, the single evaluable Stage IV RCC patient, who had residual tumor burden after surgery, remained poorly responsive to EphA2 peptides (FIG. 22).

Peptide-specific IFN-γ and IL-5 release by CD4+ T cells in ELISPOT assay. IFN-γ (Th1-type) and IL-5 (Th2-type) ELISPOT assays were used to discern altered frequency and functional bias of patient-derived Th cells against EphA2 peptides. Peripheral blood T cells were stimulated for one week with peptide-pulsed immature autologous DC (which do not appear to skew the Th1/Th2 balance, ref. 47) prior to CD4+ T cell isolation and ELISPOT analyses. The frequencies of CD4+ T cell responders against EphA2 peptides were evaluated in 19 HLA-DR4+ RCC patients (Table 1).

Figure 23:
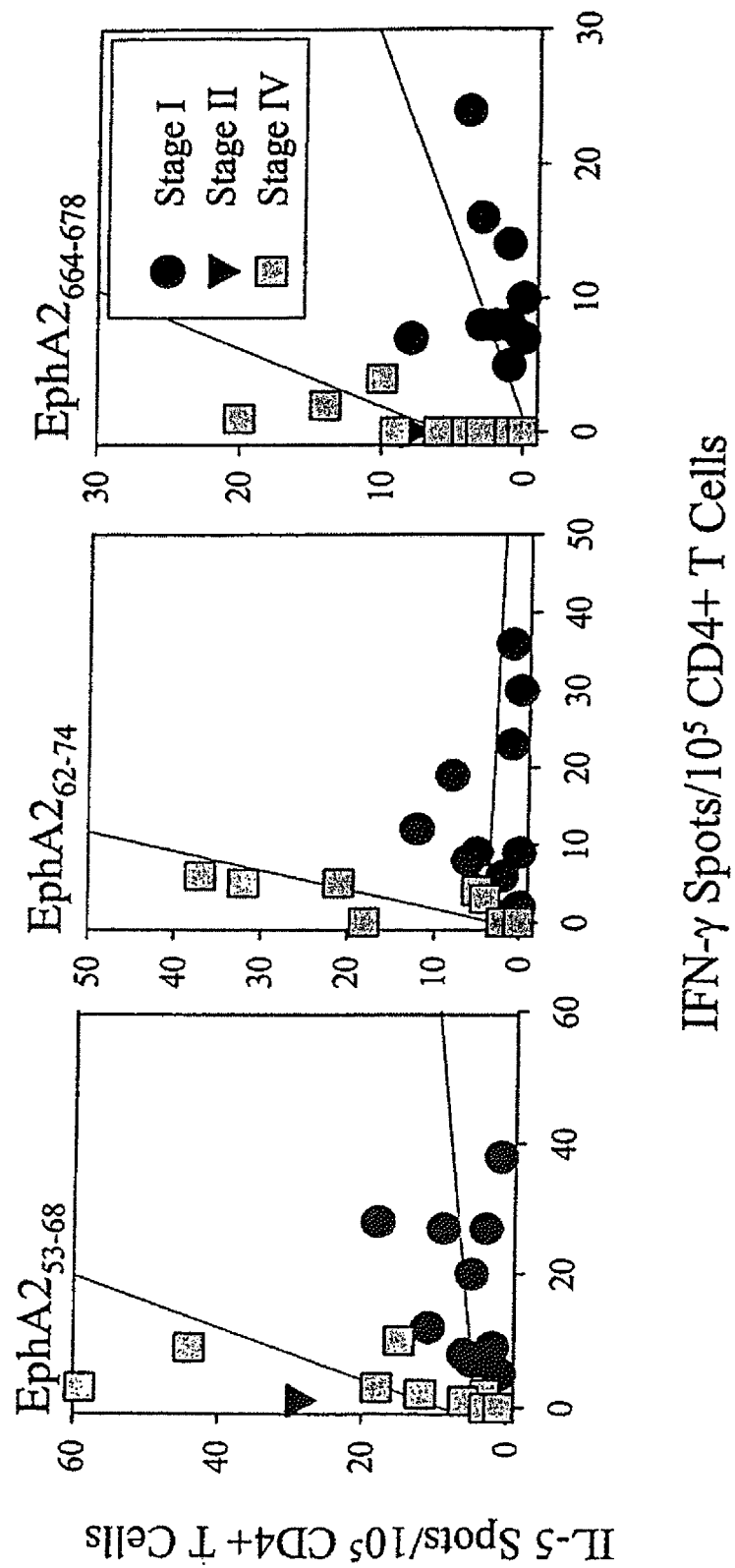
FIG. 23 provides graphs showing disease-stage skewing of functional CD4+ T cell responses to EphA2 Th epitopes in HLA-DR4+ RCC patients with active disease.

The functional nature of T cell reactivity towards EphA2 related to disease progression. Patients with Stage I disease patients displayed strongly Th1-polarized reactivity against EphA2 peptides whereas patients with more advanced stages of the disease polarized towards strong Th2 reactivity. In FIG. 23, peripheral blood was obtained from 19 HLA-DR4+ patients (Table 1) and CD4+ T cells isolated by positive MACS™-bead selection as described in Materials and Methods, below. After a one-week in vitro stimulation with EphA2 Th peptide-pulsed, autologous DCs, responder CD4+ T cells were evaluated against T2.DR4 cells pulsed with the indicated EphA2 epitopes in IFN-γ and IL-5 ELISPOT assays. Data are reported as IFN-γ spots/100,000 CD4+ T cells and represent the mean of triplicate determinations. T cell reactivity against T2.DR4 cells pulsed with the HLA-DR4-presented Malarial circumsporozooite $(CS)_{326-345}$ epitope served as the negative control in all cases, and this value was subtracted from all experimental determinations in order to determine EphA2-specific spot numbers. Each symbol within a panel represents an individual patient's response. Not every patient reacted against each peptide, but their responses were consistently polarized in accordance with the patient's disease stage.

Figure 24:
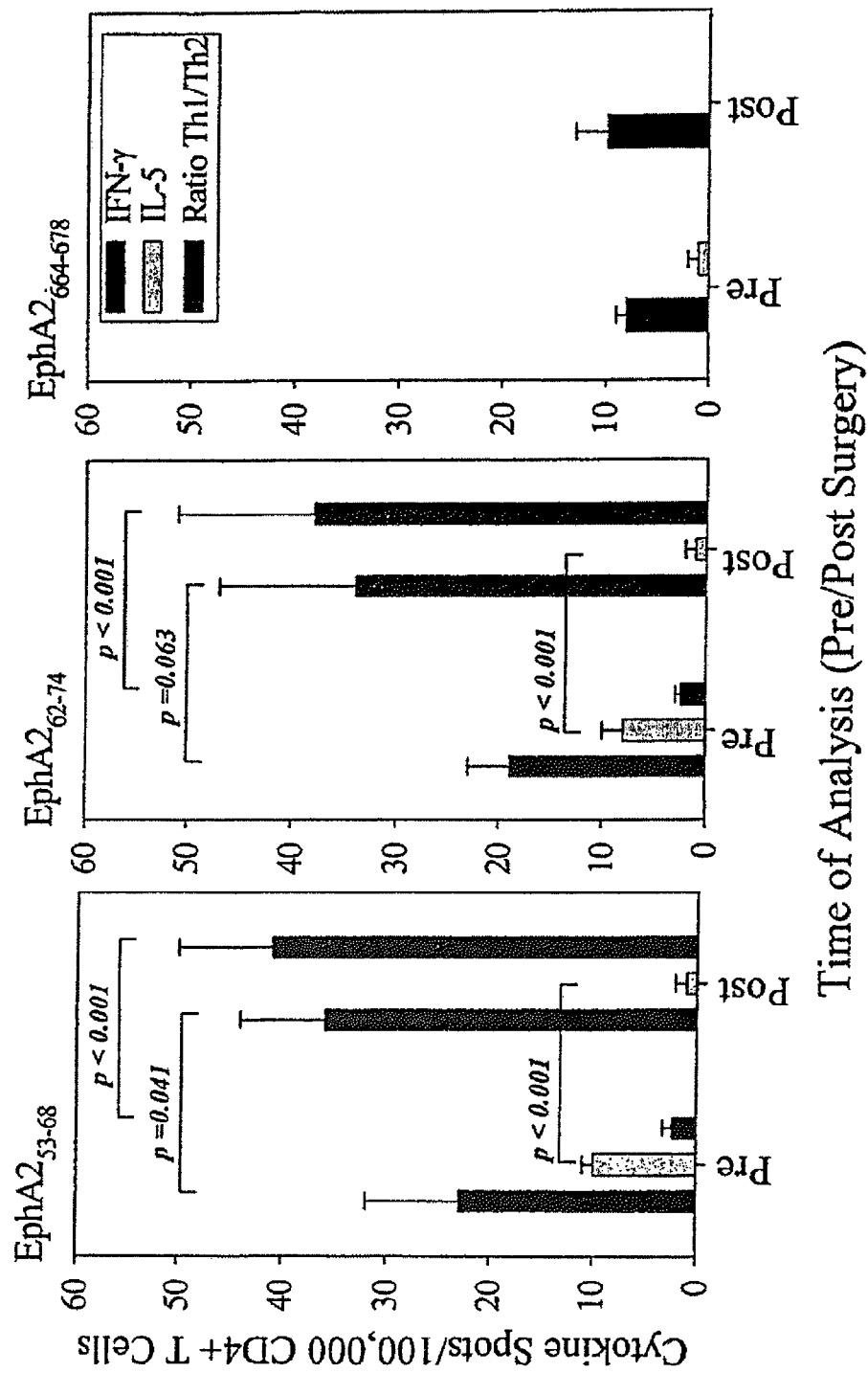
FIG. 24 provides graphs showing therapy-associated enhancement of Th1-type, and reduction in Th2-type, CD4+ T cell responses to EphA2 Th epitopes in an HLA-A2+/DR4+ patient with Stage I RCC.

One set of matched blood samples from an HLA-DR4+ patient pre- and post-therapy fortunately was available. This individual had been rendered free of disease after surgery. While the CD4+ T cells from this donor were Th1-biased before and after surgery, the frequency of IFN-γ spots associated with T cell responses against the $EphA2_{53-68}$ and $EphA2_{63-75}$ (but not the $EphA2_{863-677}$) epitopes increased post-treatment. In FIG. 24, pre- and post-surgery peripheral blood was available for a single RCC patient with Stage I disease. CD4+ T cells were isolated and analyzed for reactivity to EphA2 Th epitopes, as outlined in the FIG. 23 description, above. A statistically-significant increase in Th1-type (IFN-γ) and decrease in Th2-type (IL-5) CD4+ T cell response post-surgery was noted for the $EphA2_{53-68}$ epitope. Therapy-induced changes in CD4+ T cell response to the $EphA2_{63-75}$ epitope were similar, with the IFN-γ results approaching a p value of 0.05 and the significant reductions in IL-5 responses noted (p<0.001). T cell responses to the $EphA2_{663-677}$ epitope pre-/post-sugery were not significantly different. The ratio of Th1/Th2-type responses pre- and post-therapy is also indicated for peptides $EphA2_{53-68}$ and $EphA2_{63-75}$. p values for significant differences are indicated.

This donor was also HLA-A2 and it was observed that increased Th1-type CD4+ T cell-mediated immunity to EphA2 occurred in concert with increased frequencies of circulating IFN-γ-secreting anti-EphA2 CD8+ T cells in this patient (FIG. 22; filled circles).

Figure 25:
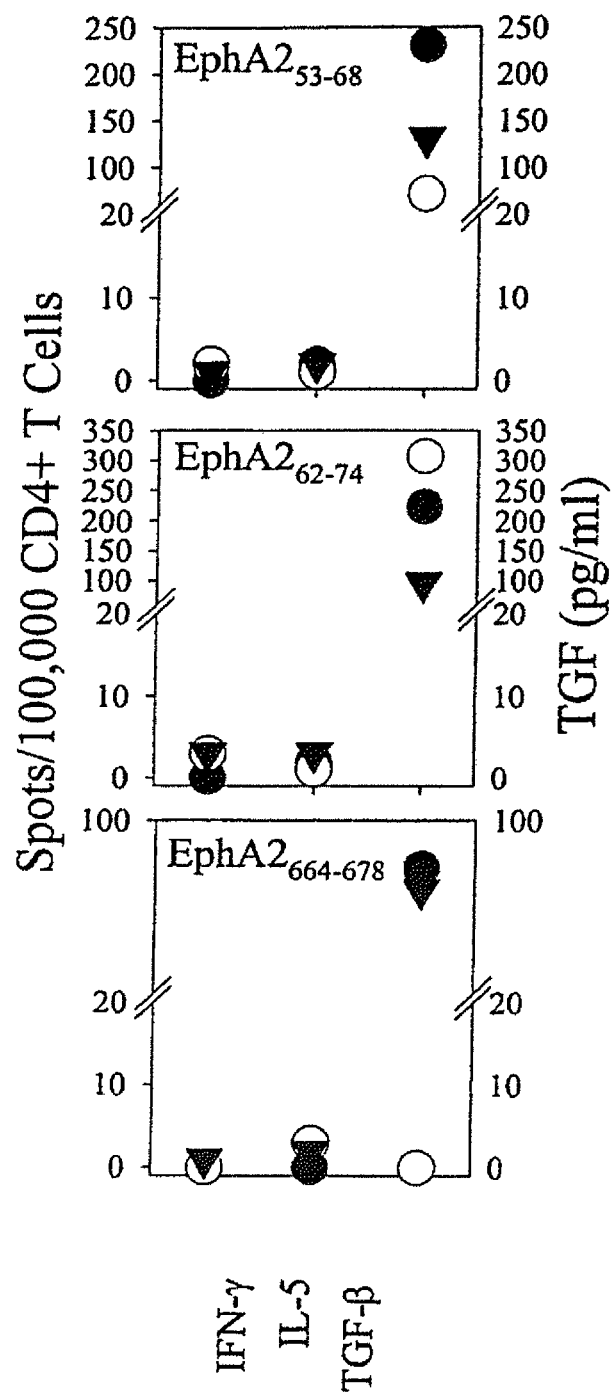
FIG. 25 provides graphs showing suppressor CD4+ T cell responses to EphA2 Th epitopes in HLA-DR4+ patients with advanced Stage IV RCC.

TGF-β and IL-10 production from RCC patient CD4+ T cells against EphA2 peptides. To evaluate whether Th3/Tr1 CD4+ T cells were present in the peripheral blood of RCC patients, TGF-β and IL-10 production following in vitro peptide-stimulation was measured. In FIG. 25, supernatants were harvested from the culture wells of IFN-γ ELISPOT assays and analyzed for levels of TGF-β1 using a commercial ELISA procedure. Of 19 HLA-DR4 patients evaluated, only the supernatants of 3 (of 8 evaluated) patients with Stage IV RCC contained detectable quantities of TGF-β1. The corresponding IFN-γ and IL-5 ELISPOT data for these patients' CD4+ T cells is also provided. Each symbol within a panel represents an individual patient's response. TGF-β production by responder CD4+ T cells was only observed in a subset (i.e. 3 of 8) of Stage IV patients and notably, these same patients displayed coordinately weak Th1 or Th2-type (IFN-γ and IL-5 ELISPOT) CD4+ T cell reactivity against EphA2 peptides. IL-10 production (above the detection limit of the ELISA) was not observed for any specimen tested.

The molecular definition of tumor-associated antigens has facilitated the development of immunotherapies designed to prime and boost tumor-specific T cell responses in cancer patients. In concert with these advances, cytokine release assays provide a powerful means to monitor the specificity and magnitude of evolving anti-tumor CD8+ and CD4+ T cell responses in the peripheral blood of patients before, during and after treatment (Keilholz U, et al. J Immunother 25; 97-138, 2002). In the present example, how, and to what extent, T cells in patients with RCC recognize novel EphA2-derived epitopes was evaluated using cytokine-specific ELISPOT assays and ELISAs.

The major finding of this example is a demonstration that renal cell carcinoma patients exhibit detectable CD4+ and CD8+ T cell reactivity towards the receptor tyrosine kinase EphA2 that is aberrantly expressed at a high frequency in RCC tumors. EphA2-specific CD8+ T cell activity is inversely proportional to the presence of active disease in these patients and is increased within 6 weeks following therapeutic intervention that results in disease-free status. Interestingly, two HLA-A2+ patients with Stage IV disease were identified who were long-term survivors (>40 months) post-surgery. Both of these individuals displayed elevated peripheral blood frequencies of IFN-γ-secreting CD8+ T cells reactive against EphA2-derived epitopes (FIG. 20). Continued maintenance of high anti-EphA2 CD8+ T cell activity in these patients may relate to their continued survival with active disease.

Somewhat in contrast with the CD8+ T cell results, it is also shown herein that a fine balance of patient Th1-type versus Th2-type CD4+ T cell responses to EphA2 peptides distinguishes between disease-grades. In particular, the most advanced forms of RCC tend to polarize towards Th2- or Tr-type anti-EphA2 responses. This polarization in functional CD4+ T cell responsiveness, combined with the potential suppressive activity mediated by T regulatory cells in patients with Stage IV disease, may play facilitating roles in disease progression.

These findings are unique in part because they indicate that that EphA2 may provide a much-needed target antigen for the design of immunotherapies for renal cell carcinoma. First, EphA2 is over-expressed in a large number of RCC specimens, including 22 of 24 (92%) RCC cell lines and 29 of 30 (97%) RCC biopsy samples, respectively (FIG. 18 and data not shown). These findings are consistent with evidence emerging from studies of other tumor types, which indicates that high levels of EphA2 apply to many cancers, including breast, colon, head and neck (Tatsumi et al., unpublished data), prostate and lung carcinoma, as well as, melanoma. If the present studies can be extended to these other clinical indications, EphA2-specific T cell activity could provide an opportunity for therapeutic intervention for these tumor types as well.

Interestingly, CD8+ T cell reactivity against EphA2 peptides (as determined in IFN-γ ELISPOT assays) differed greatly between RCC patients with active disease and those patients rendered free of disease. Yet, anti-EphA2 CD8+ T cell reactivity did not distinguish RCC disease stage. One potential explanation for this finding is that RCC tumors may suppress the generation, functionality and durability of CD8+ T cell responses against EphA2 in situ. This hypothesis is consistent with general tumor-associated immune suppression of peripheral CTL and NK cell activity, as has been previously reported (Kiessling R, et al. Cancer Immunol Immunother 48; 353-362, 1999). Notably, CD8+ T cell reactivity against EphA2-derived CTL epitopes significantly increased in the peripheral blood of three HLA-A2+ patients with Stage I RCC after surgery that rendered these individuals free of disease. In contrast, in a Stage IV patient, surgical intervention without "cure" did not change the low frequency of CD8+ T cell reactivity towards EphA2 peptides. These results are consistent with the requirement for RCC tumor clearance in situ (That is, termination of chronic (tumor) antigenic stimulation) to allow for elevation in functional Tc1-like anti-tumor CD8+ T cell responses (Liu H, et al. J. Immunol 168:3477-3483, 2002 and Moser J M, et al. Viral Immunol 14:199-216, 2001). An alternative explanation is that expansion or maintenance of EphA2-specific CD8+ T cell activity may require the concerted support of specific Th1-type responses or a shift of existing patient Th2-type or T suppressor-type to Th1-type immunity, particularly in the advanced cancer setting (Tatsumi et al., J. Exp. Med. 2002).

Th1-type biased CD4+ T cell response could only be observed in a subset of Stage I RCC patients, and Th2- or Tr-type biased CD4+ T cell responses were almost always observed in Stage IV RCC patients. It is important to stress that polarization away from Th1-type immunity in patients with advanced stage disease was tumor-specific, since individuals with Stage IV disease responded to influenza- and EBV-derived T helper epitopes in a "normal" Th1-biased manner (Tatsumi et al., J. Exp. Med. 2002 and data not shown).

While longitudinal data was available for only one HLA-DR4+ patient with Stage I disease (FIG. 24), Th1-type immunity against at least some EphA2 epitopes was strengthened and EphA2-specific, Th2-type responses lessened after surgical resection of the patient's tumor. These results are consistent with previous reports that in most cancers, the immune response is believed to be suppressed (or deviated) in advanced stage cancer patients. These results also suggest that the nature of CD4+ T cell responses against "late-stage" EphA2 peptides correlates with RCC disease stage. This finding contrasts with these previous observations for CD4+ T cell responses against the "early-stage" MAGE-6 epitopes where disease-state, but not disease-stage correlations were noted.

Th3/Tr CD4+ T cell subsets may play dominant roles as antigen-specific T "suppressor" cells, in part due to secretion of immunosuppressive cytokines such as TGF-β and/or IL-10 (Krause 1, et al. Crit Rev Immunol 20; 1-16, 2000). Based on detection of TGF-β (but not IL-10) production in 3 of 8 (38%) patients with Stage IV disease, it is possible that the population of human CD4+CD25+ T suppressor cells may hinder the patient's ability to productively eliminate EphA2-overexpressing tumors (Levings M K, et al. J Exp Med. 196; 1335-1346, 2002). These same patients failed to exhibit discernable Th1-type or Th2-type reactivity to EphA2 peptides, supporting the overall suppressive dominance of EphA2-specific T suppressor-type immunity over Th1- or Th2-type responses. These results suggest that Th2- or T suppressor-type responses are prevalent against EphA2 epitopes in advanced Stage RCC patients and likely contribute to the hyporeactivity of tumor-specific cellular immunity noted in these individuals. Future studies could test this hypothesis using flow cytometry analyses to detect HLA-DR4/EphA2 peptide tetramer binding and co-expression of CD25, CTLA-4 or the glucocorticoid-induced tumor necrosis factor receptor (as markers of T suppressor cells, Levings et al, J Exp Med. 2002).

Immunotherapies

A broad array of therapeutic vaccines are currently active or being contemplated for diverse forms of cancer. Constructive immunologic information must be gained from all ongoing trials to provide a basis for an improved design. Hence, there is a great need for the development of innovative methods for the immunological monitoring of clinically-important T cell responses, which could ultimately serve as "surrogate" endpoints. While no single assay is likely to prove sufficiently comprehensive, it is shown herein that the combination of IFN-γ and IL-5 ELISPOT assays and TGF-β ELISAs provides a sensitive means of evaluating functional T cell responses from patients with RCC or melanoma (Tatsumi et al., J. Exp. Med. 2002). These assays are amenable to in vitro detection and frequency determination of both CD8+ and CD4+ T cells specific for tumor-associated antigens. Using such techniques, our novel EphA2-derived T cell epitopes may prove useful in evaluating tumor-specific immunity in the many different cancer types in which EphA2 overexpression has been documented.

These same epitopes clearly also have potential to serve as components of a cancer vaccine. Unlike MAGE-6 reactive T cells, which are skewed toward Th2-type responses in early-stage disease (Tatsumi et al., J. Exp. Med. 2002), the imbalance in Th reactivity associated with EphA2 does not appear to occur until later-stage disease. Hence, EphA2-based adjuvant vaccination of Stage I patients could have utility for eliciting protective immunity in patients at high risk for disease recurrence or to prevent prospective metastases. Vaccination with both EphA2-derived CD4+ and CD8+ T cell epitopes may prompt high frequency anti-EphA2 CTL induction that is stabilized by the concurrent activation of specific Th1-type CD4+ T cells. Alternatively under appropriate re-polarizing or activating conditions (Vieira P L, et al. J Immunol 164; 4507-4512, 2000), dendritic cell (DC)-based vaccines incorporating EphA2 peptides may allow for previously muted Th1-type immunity to be functionally resurrected in patients with advanced stage disease, yielding potential therapeutic benefit.

Given its broad range of EphA2 overexpression among advanced-stage tumors of diverse histologies, vaccines based on antigens such as EphA2 have tremendous potential in high-incidence tumor types such as breast, prostate, colon and lung cancer, and in extremely aggressive cancers, such as pancreatic carcinoma (where we have recently observed a 100% incidence of EphA2 overexpression, data not shown). Autologous DC-EphA2 vaccines are currently under development for the treatment of patients with RCC, melanoma, prostate, head and neck or pancreatic cancer.

Example 2

Conditional Triggering of Specific CD8+ T-Cell Recognition of EphA2 Tumors In Vitro and In Vivo after Treatment with Ligand Agonists Cell Lines and Media. The T2.DR4 (HLA-A2+/−DRB1*0401+ cell line was used as the peptide-presenting cell in ELISPOT assays. The EphA2+ HLA-A2-PC-3 prostate carcinoma cell line was used as positive control for Western Blot analysis of EphA2 protein expression and was also used as a negative control target in ELISPOT assays. SLR24, an EphA2+ HLA-A2+ cell line (Tatsumi, T., et al. Cancer Res, 63: 4481-4489, 2003) was tested in Western Blot and ELISPOT assays and was also applied in the Hu-SCID treatment model. All cell lines were maintained in RPMI-1640 culture medium supplemented with 10% heat-inactivated fetal bovine serum (FBS), 100 U/ml 100 μg/ml streptomycin and 10 mM L-glutamine (all reagents from GIBCO/Life Technologies, Grand Island, N.Y.) in a humidified atmosphere under 5% $CO_2$ tension at 37° C.

Mice. Six-to-eight week old female C.B-17 scid/scid mice were purchased from Taconic Labs (Germantown, N.Y.), and maintained in micro-isolator cages. Animals were handled under aseptic conditions per an Institutional Animal Care and Use Committee (IACUC)-approved protocol and in accordance with recommendations for the proper care and use of laboratory animals.

Western Blot Analyses. Tumor cells were grown to 80-90% confluency, serum starved overnight, then treated with agonists where indicated. In addition, resected SLR24 lesions were obtained pre- and 24 h post-intratumoral injection with B61-Ig, as outlined below. Tumor samples were analyzed for EphA2 expression via Western blots using the rabbit anti-human EphA2 polyclonal antibody (clone: C-20), Santa Cruz Biotechnology, Inc., Santa Cruz, Calif.). In some experiments, samples were also analyzed for Axl (clone C-20, Santa Cruz Biotechnology, Santa Cruz, Calif.) protein content. Single tumor cell suspensions isolated from confluent tissue culture flasks or from the enzymatic digestion of resected lesions were lysed using 500 μl lysis buffer (1% Triton-X, 150 nM NaCl, 10 mM Tris pH 7.4, 1 mM EDTA, 0.2 mM SOV, 0.5% NP-40) in PBS containing protease inhibitors (Complete, Roche Diagnostic, Mannheim, Germany) for 30 min at 4° C. After centrifugation at 13,500×g for 20 minutes, the supernatant was mixed 1:1 with SDS-PAGE running buffer and proteins separated on 7.5% PAGE gels, prior to electroblotting onto nitrocellulose membranes (Millipore, Bedford, Mass.). Blots were imaged on Kodak X-Omat Blue XB-1 film (NEN Life Science Products, Boston, Mass.) after using horseradish peroxidase (HRP)-conjugated goat anti-rabbit Ig (Biorad, Hercules, Calif.) and the Western Lighting™ chemiluminescence detection kit (Perkin Elmer, Boston, Mass.). Immunoprecipitation for EphA2 were performed using the anti-EphA2 antibody D7 (Upstate Biotech, Inc.). Anti-phosphotyrosine antibodies (Clone py99, Santa Cruz Biotechnology, San Diego, Calif.) were used to assess pEphA2 content. Mouse anti-β-actin antibody (clone AC-15, Abeam, Cambridge, Mass.) was used as a loading control.

EphA2 Agonists. B61.Ig and mAb208 were kindly provided by MedImmune (Gaithersburg, Md.), B61.Ig is a chimeric protein consisting of the ligand binding domain of ephrin-A1 fused with the Fc portion of a mouse IgG antibody and was used in in vitro assays at 30 μg/ml, where indicated. mAb208 is a mouse monoclonal antibody specific for EphA2 and was used in in vitro assays at 8 μg/ml, where indicated.

Anti-EphA2 CD8+ T Cell Clones. The CL-142 and E883, HLA-A2-restricted CD8+ human T cell clones specific for $EphA2_{883-891}$, were generated as previously described (Tatsumi, T., et al. Cancer Res. 2003).

ELISPOT Assays. In vitro T cell responses were evaluated by IFN-γ ELISPOT assays as previously described (Tatsumi, T., et al. Cancer Res. 2003). Briefly, 96-well multiscreen hemagglutinin antigen plates (Millipore, Bedford, Mass.) were coated with 10 μg/ml of anti-human IFN-γ mAb (1-D1K; Mabtech, Stockholm, Sweden) in PBS (GIBCO/Life Technologies) overnight at 4° C. Unbound antibody was removed by four successive washing with PBS. After blocking the plates with RPMI-1640/10% human serum (1 hr at 37° C.), $10^5$ CD8+ T cells and T2.DR4 cells ($2 \times 10^4$ cells) pulsed with 10 μg/ml $EphA2_{883-891}$ peptide (TLADFDPRV, SEQ ID NO: 2, residues 883-891) or SLR24+/− treatment overnight with B61.Ig were seeded in triplicate in multi-screen hemagglutinin antigen plates. Control wells contained CD8+ with T2.DR4 cells pulsed with $HIV-nef_{190-198}$ peptide (AFHHVAREL, SEQ ID NO: 3) or PC3, an HLA-A2-EphA2+ tumor cell line, or T2.DR4 cells alone. Culture medium (AIM-V; GIBCO/Life Technologies) was added to yield a final volume of 200 μl/well. The plates were incubated at 37° C. in 5% $CO_2$ for 24 hr for IFN-γ assessments. Cells were removed from the ELISPOT wells by washing with PBS/0.05% Tween 20 (PBS/T). Captured cytokines were detected at sites of their secretion by incubation for 2 hr with biotinylated mAb anti-human IFN-γ (7-B6-1; Mabtec) at 2 μg/ml in PBS/0.5%. Plates were washed six times using PBS/T, and avidin-peroxidase complex (diluted 1:100; Vectastain Elite Kit; Vector Laboratories, Burlingame, Calif.) was added for 1 hr. Unbound complex was removed by three successive washes using PBS/T, then with three rinses with PBS alone. AEC substrate (3-Amino-9-ethylcarbazol; Sigma, St. Louis, Mo.) was added and incubated for 5 min for the IFN-γ ELISPOT. Spots were imaged using the Zeiss AutoImager.

Flow Cytometry. For phenotypic analysis of control or ligand agonist-treated tumor cells, PE- or FITC-conjugated monoclonal antibodies against HLA class I (W6/32; pan-class I specific; Serotec Inc., Raleigh, N.C.) or human CD40 (Ancell Corp., Bayport, Minn.) and appropriate isotype controls (purchased from BD Biosciences, San Jose, Calif.) were used, and flow cytometric analysis was performed using a FACscan (Becton Dickinson, San Jose, Calif.) flow cytometer. The results of the flow cytometric analysis are reported in arbitrary mean fluorescence intensity (MFI) units.

Hu-SCID Tumor Model. C.B17-scid/scid mice were injected s.c. in the right flank with $1 \times 10^6$ SLR24 RCC cells and tumors allowed to establish to a size of approximately 30 mm2 (i.e. day 18 post-injection). The tumor-bearing mice were then randomized into 4 groups (5 animals each with comparable tumor sizes) that received either no treatment, a single intratumoral injection of 50 μg of B61-Ig (in 50 μl saline) on day 18, a single tail-vein injection with $5 \times 10^6$ cloned E883 (anti-$EphA2_{883-891}$ specific) CD8+ T cells in 100 μl saline on day 19, or the combined d18 (B61-Ig) plus d19 (E883 adoptive transfer) regimen. Animals were evaluated every 3-4 days for tumor size, with tumor-free status noted on day 40 post-tumor inoculation. For the analyses of EphA2 content in SLR24 tumor lesions pre- and post-administration of B61-Ig, tumors were surgically resected from euthanized mice, digested into single-cell suspensions using a DNAse, hyaluronidase, DNAse cocktail as previously described (Itoh, T., et al. J Immunol. 153: 1202-1215, 1994) and filtered through Nitex mesh (Tetko, Kansas City, Mo.), prior to tumor cell solubilization and Western Blotting, as outlined above.

Statistical Analyses. Statistical differences between groups were evaluated using a two-tailed Student's T test, with p values <0.05 considered significant.

Results

B61.Ig and mAb208 Induce EphA2 Phosphorylation and Degradation.

Figure 26:
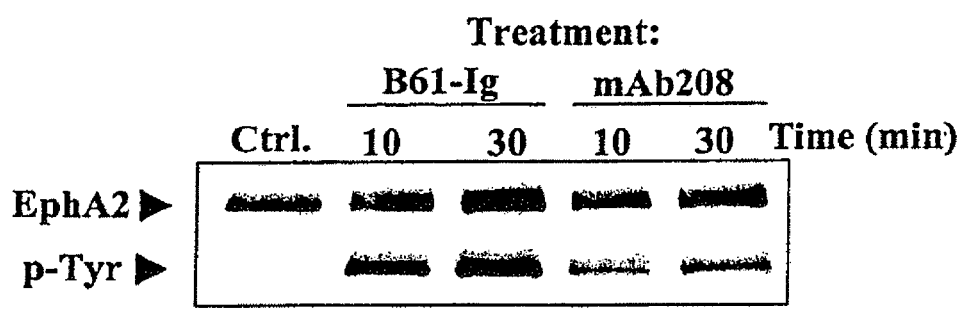
FIG. 26 is a Western blot showing that EphA2 agonists induce the phosphorylation of EphA2.
Figure 27:
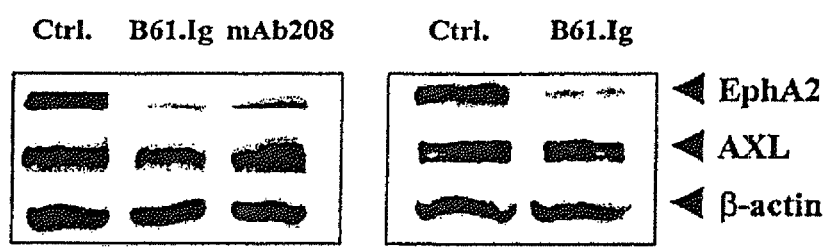
FIG. 27 shows that EphA2 agonists induce the degradation of EphA2.

Previous studies have demonstrated that tumor cells have unstable cell-cell contacts and that this impairs the ability of EphA2 to interact with its ligands on apposing cells. Consequently, the EphA2 in malignant cells generally is not itself tyrosine phosphorylated. Consistent with this, Western Blot analyses verified that the EphA2 in malignant cells (e.g., PC3) is weakly phosphorylated. In FIG. 26, PC3 ($2-4\times10^6$) cells were treated at the indicated time points (in min) with either B61.Ig (30 μg/ml) or mAb208 (8 μg/ml). B61.Ig is a fusion protein consisting of the EphA2 binding domain of ephrin-A1 (a major ligand of EphA2) fused to a human Fc domain. Cellular lysates were resolved by SDS-PAGE and EphA2 protein was immunoprecipitated using the anti-EphA2 antibodies D7 in pull-down assays. Western blot analyses were then performed using anti-EphA2 and anti-phosphotyrosine antibodies, respectively. Data are representative of 3 independent experiments performed. However, treatment of these cells with reagents that can bind EphA2, even in the absence of stable intercellular contacts (agonistic monoclonal antibodies and artificial ligands), is sufficient to increase EphA2 phosphotyrosine content. Immunoblotting of cell lysates verified that this treatment subsequently induces EphA2 protein degradation. To verify equal loading, the membranes were probed with antibodies specific for β-actin, which did not change in response to EphA2 agonist treatment. The specificity for EphA2 was further verified by showing that the levels of the Axl receptor tyrosine kinase were not altered in response to EphA2-specific reagents. In FIG. 27, PC3 (left panel) and SLR24 (right panel) cells were treated for 6 hours with either B61.Ig (30 μg/ml) or mAb208 (8 μg/ml) at 37° C. Cell lysates were resolved by 12.5% SDS-PAGE and Western blot analyses were performed using polyclonal anti-EphA2 and control anti-β-actin antibodies. Anti-AXL antibodies were used to image identically-prepared lysates as a specificity control in these experiments. Data are representative of 3 independent experiments performed on each tumor cell line. Comparable findings were obtained in multiple and different EphA2-overexpressing cell systems, including cell models of breast, lung, pancreatic and renal cell carcinoma (FIG. 27 and data not shown).

Figure 28A:
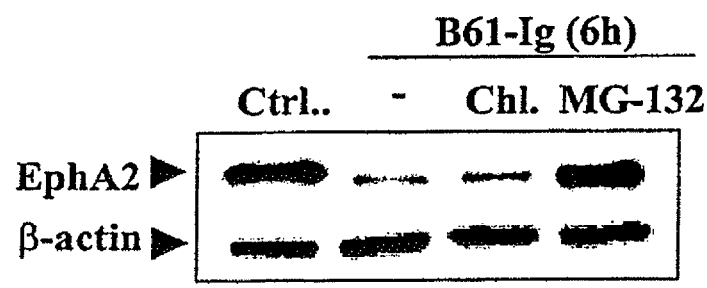
FIGS. 28A and 28B show that EphA2 agonists-induced degradation is inhibited by MG132, but not by chloroquine.
Figure 28B:
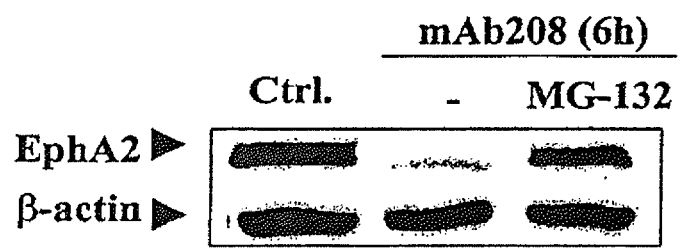

Based on evidence that ligand-mediated stimulation of EphA2 induces receptor internalization and degradation within proteasomes, these findings were verified and extended to show that antibody stimulation similarly induces proteasomal cleavage of EphA2. In FIGS. 28A and 28B PC3 cells were either not treated or treated with B61.Ig (FIG. 28A) or mAb208 (FIG. 28B), as described previously with respect to FIG. 26. MG-132 (50 μM) and chloroquine (Chl.; 100 μM) were also added to cultures, where indicated, 30 min. prior to the addition of EphA2 agonists and remained in the cultures for the duration of the 24 h experiment. Cell lysates were generated and resolved using SDS-PAGE. Western blot analyses were then performed using anti-EphA2 antibodies and negative control anti-β-actin antibodies. Data are representative of 3 independent experiments performed. EphA2 degradation was blocked by the treatment with the 26S proteasome inhibitor, MG-132. In contrast, the addition of the endosomal/lysosomal inhibitor chloroquine did not prevent EphA2 degradation, thus indicating that proteasomal and not lysosomal degradation of EphA2 is the major mechanism responsible for EphA2 degradation.

Figure 29:
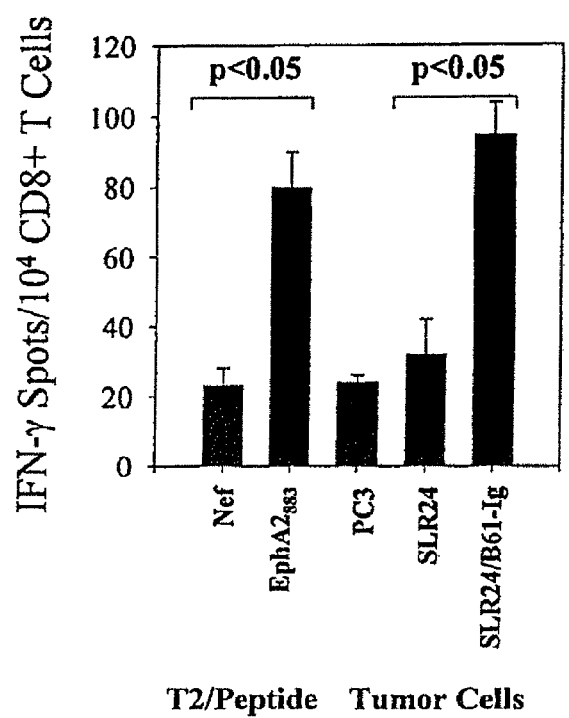
FIG. 29 is a graph showing that EphA2 agonists sensitize the RCC cell line SLR24 to recognition by anti-EphA2 CD8+ T cell clone CL.142.

EphA2 Agonist Treatment Enhances CD8$^+$ T Cell Recognition of EphA2$^+$ Tumors in Vitro. Since agonistic antibodies triggered proteasomal degradation of EphA2, it was hypothesized that this could increase presentation of EphA2 peptides on HLA class I complexes. If correct, then it logically would follow that agonism of EphA2 could enhance recognition by EphA2-specific CD8$^+$ T cells. To address this question, EphA2$^+$ SLR24 RCC cells were incubated with B61-Ig prior to evaluating their ability to be recognized by the EphA2$_{883-891}$ specific CTL clone 142 (CL.142). As a readout of T cell activation, the samples were subjected to IFN-γ-based ELISPOT assays. In FIG. 29, the anti-EphA2 CTL clone CL142 (Dobrzanski, P., et al. Cancer Res. 64: 910-919, 2004) was analyzed for reactivity against T2.DR4 (A2$^+$) cells pulsed with the EphA2$_{883-891}$ peptide epitope, or against untreated or agonist-triggered HLA-A2$^+$/EphA2$^+$ SLR24 cells as targets in IFN-γ ELISPOT assays. Control target cells include: T2.DR4 cells pulsed with the HLA-A2-presented HIV-nef$_{190-198}$ (negative control for peptide specificity) and PC3 (HLA-A27EphA2$^+$) prostate carcinoma cells. B61.Ig treatment (30 μg/ml) was applied overnight to ensure EphA2 degradation and HLA antigen processing and presentation of EphA2 epitopes). Data are reported at IFN-γ specific spots/ 10,000 CL.142 cells and are derived from one representative experiment of 3 performed.

Pretreatment of SLR24 with B61.Ig significantly enhanced CL.142 recognition of SLR24 relative to untreated control cells. It was then considered that the increased tumor cell recognition could have been due to changes in tumor cell expression of HLA class I or costimulatory molecules. To address this, SLR24 cells were treated with agonistic antibodies and surface levels of HLA class I and CD40 evaluated by flow cytometry. Notably, the staining intensity of both HLA class I and CD40 was not significantly altered following agonism of EphA2 (Table 4). As a further control for the selectivity of this effect, it was observed that recognition of SLR24 tumor cells by HLA-A2 alloreactive CTLs was not altered pre- vs. post-treatment with EphA2 agonists (data not shown).

TABLE 4

EphA2 Agonists Affect HLA Class I or CD40 Expression on SLR24 tumor cells
Mean Fluorescence Intensity

| Treatment | MG-132 (+/−) | Control | W6/32 | CD40 |
|---|---|---|---|---|
| Untreated | — | 0.5 | 124.7 | 14.8 |
| MAb208 | — | 5.5 | 116.5 | 19.8 |

The SLR24 RCC cell line was either not treated or treated with mAb208 (10 μg/ml) as outlined in the description of FIGS. 28A and 28B, above. Treated cells were then analyzed for expression of HLA class I and CD40 molecules by flow cytometry as described in Materials and Methods. Data presented is the mean fluorescence intensity of expression for the indicated markers.

Figure 30A:
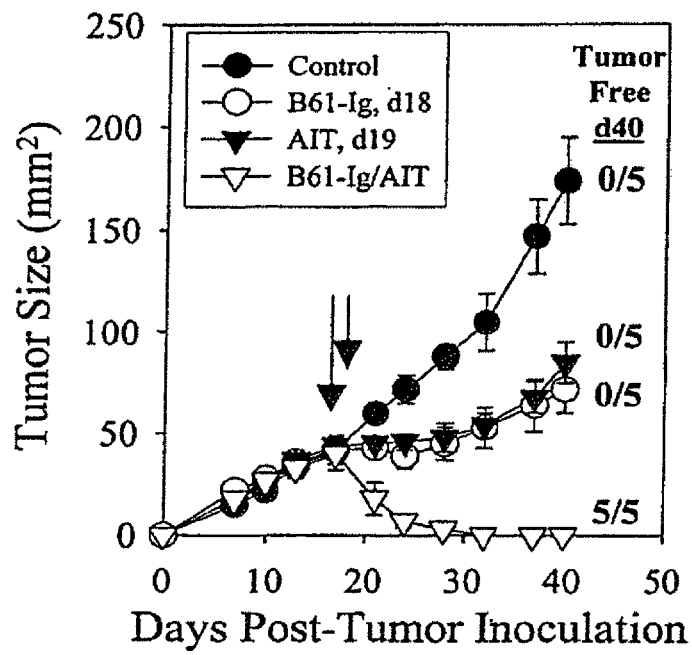
FIGS. 30A and 30B demonstrate "agonistic" triggering of tumor cell EphA2 in situ enhances the therapeutic efficacy of adoptively transferred anti-EphA2 specific CD8+ T cells.
Figure 30B:
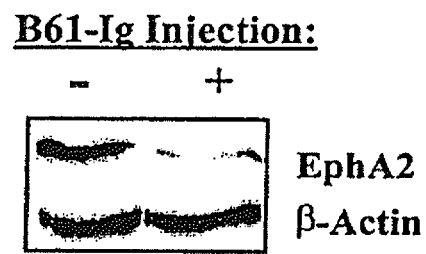

EphA2 Agonist Treatment Enhances the efficacy of adoptively transferred anti-EphA2 CD8$^+$ T Cells in a Hu-SCID Tumor Model. To determine whether the conditional (agonist-induced) increase in anti-EphA2 CD8$^+$ T cell reactivity against EphA2$^+$ tumors could be of potential clinical significance, a Hu-SCID tumor model system was established. SLR24 tumors were injected into C.B-17 scid/scid mice and allowed to progress to a size of approximately 30 mm$^2$, at which time, animals were either left untreated, or treated with intratumoral injection of B61-Ig (day 18 post-tumor inoculation) and/or intravenous delivery of a HLA-A2-restricted, anti-EphA2883-891 CD8+ T cell clone (E883). In FIG. 30A; Female CB17-scid/scid mice were injected with 1×10$^6$ human SLR24 (HLA-A2+/EphA2+) RCC cells s.c. in the right flank and allowed to establish to a size of approximately 30 mm$^2$ (i.e. d18). Animals were then randomized into 4 cohorts (5 animals each) receiving no treatment (control), intratumoral injection of B61-Ig (50 μg) on d±8 to trigger EphA2 degradation and proteasomal processing, intravenous (tail-vein) injection of 5×10$^6$ cloned E883 anti-EphA2883-891 CD8+ T cells on di 9, or both the B61-Ig (dl 8) and CD8+ T cell (d19) injections. Animals were evaluated every 3-4 days for tumor size, with tumor-free status noted on day 40 post-tumor inoculation. Arrows indicate treatment days. In FIG. 30B, in repeat experiments, tumors were resected from animals on day 19 (i.e. 24 hours after B61-Ig administration and Western Blots performed to validate EphA2 degradation in situ.

As depicted in FIG. 30A, while the administration of either B61-Ig or E883 T cells promoted the delayed growth of SLR24 tumors, no animals were cured by these therapies. In marked contrast, the combinational therapy including 1361-Ig delivery (which promoted EphA2 processing in situ, FIG. 30B) and the adoptive transfer of anti-EphA2 CD8+ T cells, promoted the rapid resolution of disease in 5/5 treated mice. In control cohorts, B61-Ig treatment combined with the adoptive transfer of cloned CD8+ T cells specific for the HLA-A2-presented influenza matrix$_{58-66}$ epitope, provided no enhanced benefit vs. B61-Ig treatment alone (data not shown).

The major finding of the present study is that the treatment of tumor cells with agonists that promote EphA2 autophosphorylation and proteasomal processing also result in improved recognition by EphA2-specific CD8+ T-cells both in vitro and in vivo. As a consequence, EphA2-reactive CD8+ T cells are rendered more effective in mediating the regression of tumor lesions in situ.

In normal epithelia, EphA2 localizes to cell-cell boundaries, where it constitutively binds its ligands. Consequently, the EphA2 in non-transformed cells is tyrosine phosphorylated and mediates signals that serve to limit epithelial cell growth. In particular, phosphorylated EphA2 molecules form signaling complexes with adapter proteins that contain SH2 domains (e.g., c-Cbl, SHC, SLAP, and GRB2) alters enzymatic activity of selected downstream effectors (e.g., FAK, SHP-2, PI 3-kinase, LMW-PTP). These signals, in turn, decrease the ability of EphA2$^+$ epithelial cells to establish or maintain stable contacts with the surrounding extracellular matrix (ECM).

The interaction with c-Cbl is particularly relevant to the present findings. c-Cbl contains an ubiquitin-E3 ligase and targets proteins for degradation via the proteasome. The results herein indicate that proteasomal degradation increases T cell recognition of EphA2, presumably by cleaving EphA2 into peptides that are loaded into HLA complexes for subsequent antigen presentation to effector T cells.

Tumor cells generally have unstable cell-cell contacts, which appears to preclude access of EphA2 to its membrane-anchored ligands. This is consistent with experimental evidence that the EphA2 in tumor cells is overexpressed, but unphosphorylated. Compounding decreased ligand binding, EphA2 molecules expressed by tumor cells serve as substrates for certain oncogenic tyrosine phosphatases, which provide an additional means of decreasing EphA2 phosphotyrosine content. Regardless of the cause, decreased phosphotyrosine content causes the EphA2 in tumor cells to increase their malignant character. In part, the increased invasiveness relates to increased tumor cell interactions with the ECM. These changes are frequently observed in clinical specimens of cancer. Under such conditions, EphA2 ligand agonists can restore a normalized pattern of contact inhibited growth and reduce the invasiveness of EphA2+ tumor cells.

The ability of agonistic reagents to conditionally and specifically trigger EphA2 degradation provide opportunities for the development of new therapeutic strategies for the treatment patients with EphA2$^+$ cancers. In particular, these results suggest that clinical impact of endogenous, anti-EphA2 T cell-mediate immunity could be enhanced by combining passive and active EphA2-specific immunotherapies. Previous studies have shown that a subset of T cells isolated from cancer patients can be stimulated following presentation of EphA2 peptides on HLA molecules (Tatsumi, T., Cancer Res. 2003 and Alves, P. M. et al. Cancer Res. 63:8476-8480, 2003). These studies were conducted using ex vivo stimulation of T cells using DC-based vaccination approaches, which could certainly be employed in the clinic.

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference into the specification to the same extent as if each individual publication, patent or patent application was specifically and individually indicated to be incorporated herein by reference.

We claim:

1. An isolated peptide that consists of 9-35 amino acid residues and wherein said isolated peptide comprises the peptide TLADFDPRV (SEQ ID NO:2, residues 883-891), where said TLADFDPRV (SEQ ID NO:2, residues 883-891) peptide (i) has up to one conservative amino acid substitution within the conservative substitution groups (a) S and T, (b) L, I and V, and (c) E and D; and (ii) retains the ability to stimulate a T-cell immune response to EphA2 as determined by ELISPOT assay.

2. The isolated peptide of claim 1 that comprises the peptide TLADFDPRV (SEQ ID NO:2, residues 883-891).

3. A vaccine formulation comprising an isolated peptide that consists of 9-35 amino acid residues and wherein said isolated peptide comprises the peptide TLADFDPRV (SEQ ID NO:2, residues 883-891), where said TLADFDPRV (SEQ ID NO:2, residues 883-891) peptide (i) has up to one conservative amino acid substitution within the conservative substitution groups (a) S and T, (b) L, I and V, and (c) E and D; and (ii) retains the ability to stimulate a T-cell immune response to EphA2 as determined by ELISPOT assay, and a pharmaceutically acceptable carrier.

4. The vaccine formulation of claim 3 where the isolated peptide comprises the peptide TLADFDPRV (SEQ ID NO:2, residues 883-891).

5. The vaccine formulation of claim 3 that further comprises an adjuvant.

6. The vaccine formulation of claim 4 that further comprises an adjuvant.

7. The vaccine formulation of claim 3 wherein the isolated peptide comprises a second peptide where said second peptide is not an EphA2 peptide and is immunogenic.

8. The vaccine formulation of claim 4 wherein the isolated peptide comprises a second peptide where said second peptide is not an EphA2 peptide and is immunogenic.

9. The vaccine formulation of claim 5 wherein the isolated peptide comprises a second peptide where said second peptide is not an EphA2 peptide and is immunogenic.

10. The vaccine formulation of claim 6 wherein the isolated peptide comprises a second peptide where said second peptide is not an EphA2 peptide and is immunogenic.

* * * * *

UNITED STATES PATENT AND TRADEMARK OFFICE
CERTIFICATE OF CORRECTION

PATENT NO. : 8,574,584 B2
APPLICATION NO. : 13/355343
DATED : November 5, 2013
INVENTOR(S) : Storkus et al.

Page 1 of 1

It is certified that error appears in the above-identified patent and that said Letters Patent is hereby corrected as shown below:

On the title page, item [54] and in the Specification, Col. 1, line 1 Title: EPHA2 T CELL EPITOPES AND USES THEREFOR should read -- EPHA2 T-CELL EPITOPES AND USES THEREFOR --

On the title page, item (75) Inventor: Michael S. Klnch, Laytonsville, MD should read -- Michael S. Kinch, Laytonsville, MD --

Signed and Sealed this
Twenty-fourth Day of December, 2013

Margaret A. Focarino
*Commissioner for Patents of the United States Patent and Trademark Office*